United States Patent
Belhe et al.

(10) Patent No.: US 9,962,278 B2
(45) Date of Patent: May 8, 2018

(54) MODULAR GASTROINTESTINAL PROSTHESES

(75) Inventors: Kedar R. Belhe, Minnetonka, MN (US); Paul J. Thompson, Minnetonka, MN (US)

(73) Assignee: METAMODIX, INC., Plymouth, MN (US)

( * ) Notice: Subject to any disclaimer, the term of this patent is extended or adjusted under 35 U.S.C. 154(b) by 271 days.

(21) Appl. No.: 13/493,144

(22) Filed: Jun. 11, 2012

(65) Prior Publication Data

US 2012/0253259 A1    Oct. 4, 2012

Related U.S. Application Data

(62) Division of application No. 12/752,697, filed on Apr. 1, 2010, now Pat. No. 8,211,186.

(60) Provisional application No. 61/211,853, filed on Apr. 3, 2009.

(51) Int. Cl.
*A61F 2/04* (2013.01)
*A61F 5/00* (2006.01)

(52) U.S. Cl.
CPC .......... *A61F 5/0076* (2013.01); *A61F 5/0079* (2013.01); *A61F 2002/044* (2013.01); *A61F 2002/045* (2013.01)

(58) Field of Classification Search
CPC .............................. A61F 5/0076; A61F 5/0079
See application file for complete search history.

(56) References Cited

U.S. PATENT DOCUMENTS

| | | | |
|---|---|---|---|
| 4,134,405 | A | 1/1979 | Smit |
| 4,204,530 | A | 5/1980 | Finney |
| 4,246,893 | A | 1/1981 | Berson |
| 4,314,405 | A | 2/1982 | Park |
| 4,315,509 | A | 2/1982 | Smit |
| 4,416,267 | A | 11/1983 | Garren et al. |
| 4,501,264 | A | 2/1985 | Rockey |
| 4,641,653 | A | 2/1987 | Rockey |
| 4,716,900 | A | 1/1988 | Ravo et al. |

(Continued)

FOREIGN PATENT DOCUMENTS

| | | |
|---|---|---|
| AU | 2006227471 B2 | 9/2006 |
| AU | 2014200766 B2 | 6/2015 |

(Continued)

OTHER PUBLICATIONS

International Search Report and Written Opinion issued in PCT/US2012/023048, dated Jun. 22, 2012.

(Continued)

*Primary Examiner* — Brian Dukert
(74) *Attorney, Agent, or Firm* — Faegre Baker Daniels LLP

(57) ABSTRACT

A modular system for therapy within a gastrointestinal system. The system includes anchoring or attachment functionality embodied in a low-profile implant technology and removable therapy components, which can be reversibly attached to these low-profile implants to accomplish various therapies. This modular design allows the physician to tailor the therapy to the patient's needs. The modular system has the potential to create conduits for diversion and/or restriction of food and organ secretions and to facilitate the treatment of metabolic disorders such as obesity and T2DM.

20 Claims, 79 Drawing Sheets

(56) References Cited

U.S. PATENT DOCUMENTS

| | | |
|---|---|---|
| 4,719,916 A | 1/1988 | Ravo |
| 4,763,653 A | 8/1988 | Rockey |
| 4,899,747 A | 2/1990 | Garren et al. |
| 4,905,693 A | 3/1990 | Ravo |
| 5,234,454 A | 8/1993 | Bangs |
| 5,246,456 A | 9/1993 | Wilkinson |
| 5,306,300 A | 4/1994 | Berry |
| 5,322,697 A | 6/1994 | Meyer |
| 5,423,872 A | 6/1995 | Cigaina |
| 5,474,563 A | 12/1995 | Myler et al. |
| 5,480,423 A | 1/1996 | Ravenscroft et al. |
| 5,749,921 A | 5/1998 | Lenker et al. |
| 5,753,253 A | 5/1998 | Meyer |
| 5,755,769 A * | 5/1998 | Richard ............. A61F 2/90 623/1.2 |
| 5,820,584 A | 10/1998 | Crabb |
| 6,017,563 A | 1/2000 | Knight et al. |
| 6,224,627 B1 | 5/2001 | Armstrong et al. |
| 6,267,988 B1 | 7/2001 | Meyer |
| 6,454,699 B1 | 9/2002 | Forsell |
| 6,540,789 B1 | 4/2003 | Silverman et al. |
| 6,558,400 B2 | 5/2003 | Deem et al. |
| 6,675,809 B2 | 1/2004 | Stack et al. |
| 6,676,674 B1 | 1/2004 | Dudai |
| 6,740,121 B2 | 5/2004 | Geitz |
| 6,755,869 B2 | 6/2004 | Geitz |
| 6,802,868 B2 | 10/2004 | Silverman et al. |
| 6,845,776 B2 | 1/2005 | Stack et al. |
| 6,946,002 B2 | 9/2005 | Geitz |
| 6,994,095 B2 | 2/2006 | Burnett |
| 7,025,791 B2 | 4/2006 | Levine et al. |
| 7,037,343 B2 | 5/2006 | Imran |
| 7,037,344 B2 | 5/2006 | Kagan et al. |
| 7,044,979 B2 | 5/2006 | Silverman et al. |
| 7,090,699 B2 | 8/2006 | Geitz |
| 7,111,627 B2 | 9/2006 | Stack et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,163,554 B2 | 1/2007 | Williams et al. |
| 7,175,638 B2 | 2/2007 | Gannoe et al. |
| 7,175,669 B2 | 2/2007 | Geitz |
| 7,211,094 B2 | 5/2007 | Gannoe et al. |
| 7,211,114 B2 | 5/2007 | Bessler et al. |
| 7,214,233 B2 | 5/2007 | Gannoe et al. |
| 7,220,237 B2 * | 5/2007 | Gannoe ............. A61B 17/072 128/898 |
| 7,220,284 B2 | 5/2007 | Kagan et al. |
| 7,223,277 B2 | 5/2007 | DeLegge |
| 7,229,428 B2 | 6/2007 | Gannoe et al. |
| 7,261,725 B2 | 8/2007 | Binmoeller |
| 7,267,694 B2 | 9/2007 | Levine et al. |
| 7,288,099 B2 | 10/2007 | Deem et al. |
| 7,288,101 B2 | 10/2007 | Deem et al. |
| 7,291,160 B2 | 11/2007 | DeLegge |
| 7,306,614 B2 | 12/2007 | Weller et al. |
| 7,314,489 B2 | 1/2008 | McKenna et al. |
| 7,316,716 B2 | 1/2008 | Egan |
| 7,329,285 B2 | 2/2008 | Levine et al. |
| 7,335,210 B2 | 2/2008 | Smit |
| 7,347,875 B2 | 3/2008 | Levine et al. |
| 7,354,454 B2 | 4/2008 | Stack et al. |
| 7,364,542 B2 | 4/2008 | Jambor et al. |
| 7,364,591 B2 | 4/2008 | Silverman et al. |
| 7,367,937 B2 | 5/2008 | Jambor et al. |
| 7,431,725 B2 | 10/2008 | Stack et al. |
| 7,476,256 B2 | 1/2009 | Meade et al. |
| 7,503,922 B2 | 3/2009 | Deem et al. |
| 7,507,218 B2 | 3/2009 | Aliski et al. |
| 7,510,559 B2 | 3/2009 | Deem et al. |
| 7,513,914 B2 | 4/2009 | Schurr |
| 7,569,056 B2 | 8/2009 | Cragg et al. |
| 7,601,178 B2 | 10/2009 | Imran |
| 7,608,114 B2 | 10/2009 | Levine et al. |
| 7,608,578 B2 | 10/2009 | Miller |
| 7,618,435 B2 | 11/2009 | Opolski |
| 7,628,821 B2 | 12/2009 | Stack et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,815,589 B2 | 10/2010 | Levine et al. |
| 7,837,643 B2 | 11/2010 | Levine et al. |
| 7,837,669 B2 | 11/2010 | Dann et al. |
| 7,935,073 B2 | 5/2011 | Levine et al. |
| 7,976,488 B2 | 7/2011 | Levine et al. |
| 7,981,163 B2 | 7/2011 | Levine et al. |
| 8,105,392 B2 | 1/2012 | Durgin |
| 8,114,045 B2 | 2/2012 | Surti |
| 8,182,441 B2 * | 5/2012 | Swain ............. A61F 5/0076 604/8 |
| 8,211,186 B2 | 7/2012 | Belhe et al. |
| 8,282,598 B2 | 10/2012 | Belhe et al. |
| 8,579,849 B2 | 11/2013 | Grau et al. |
| 8,882,698 B2 | 11/2014 | Levine et al. |
| 9,044,300 B2 | 6/2015 | Belhe et al. |
| 9,173,760 B2 | 11/2015 | Belhe et al. |
| 9,278,019 B2 | 3/2016 | Thompson et al. |
| 2002/0183768 A1 | 12/2002 | Deem et al. |
| 2002/0188354 A1 | 12/2002 | Peghini |
| 2003/0040804 A1 | 2/2003 | Stack et al. |
| 2003/0040808 A1 | 2/2003 | Stack et al. |
| 2003/0060894 A1 | 3/2003 | Dua et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0158601 A1 | 8/2003 | Silverman et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0019388 A1 | 1/2004 | Starkebaum |
| 2004/0024386 A1 | 2/2004 | Deem et al. |
| 2004/0039452 A1 | 2/2004 | Bessler |
| 2004/0088022 A1 | 5/2004 | Chen |
| 2004/0092892 A1 | 5/2004 | Kagan et al. |
| 2004/0093091 A1 | 5/2004 | Gannoe et al. |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0133147 A1 | 7/2004 | Woo |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0199262 A1 | 10/2004 | Dua et al. |
| 2004/0204768 A1 | 10/2004 | Geitz |
| 2004/0220682 A1 | 11/2004 | Levine et al. |
| 2004/0249362 A1 | 12/2004 | Levine et al. |
| 2005/0004681 A1 | 1/2005 | Stack et al. |
| 2005/0022827 A1 | 2/2005 | Woo et al. |
| 2005/0033226 A1 | 2/2005 | Kim |
| 2005/0033331 A1 | 2/2005 | Burnett et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0070934 A1 | 3/2005 | Tanaka et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080444 A1 | 4/2005 | Kraemer et al. |
| 2005/0080480 A1 | 4/2005 | Bolea et al. |
| 2005/0080491 A1 | 4/2005 | Levine et al. |

(56) References Cited

U.S. PATENT DOCUMENTS

| | | |
|---|---|---|
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149200 A1 | 7/2005 | Silverman et al. |
| 2005/0177181 A1 | 8/2005 | Kagan et al. |
| 2005/0183730 A1 | 8/2005 | Byrum |
| 2005/0192614 A1 | 9/2005 | Binmoeller |
| 2005/0197714 A1 | 9/2005 | Sayet |
| 2005/0228413 A1 | 10/2005 | Binmoeller et al. |
| 2005/0228504 A1* | 10/2005 | Demarais ......... A61B 17/12099 623/23.65 |
| 2005/0240279 A1 | 10/2005 | Kagan et al. |
| 2005/0246037 A1 | 11/2005 | Starkebaum |
| 2005/0247320 A1 | 11/2005 | Stack et al. |
| 2005/0250980 A1 | 11/2005 | Swanstrom et al. |
| 2005/0251157 A1 | 11/2005 | Saadat et al. |
| 2005/0251206 A1 | 11/2005 | Maahs et al. |
| 2005/0256587 A1 | 11/2005 | Egan |
| 2005/0267499 A1 | 12/2005 | Stack et al. |
| 2005/0273060 A1 | 12/2005 | Levy et al. |
| 2005/0277963 A1 | 12/2005 | Fields |
| 2005/0283107 A1 | 12/2005 | Kalanovic et al. |
| 2005/0288555 A1 | 12/2005 | Binmoeller |
| 2006/0009858 A1 | 1/2006 | Levine et al. |
| 2006/0020247 A1 | 1/2006 | Kagan et al. |
| 2006/0020277 A1 | 1/2006 | Gostout et al. |
| 2006/0030949 A1 | 2/2006 | Geitz |
| 2006/0036267 A1 | 2/2006 | Saadat et al. |
| 2006/0064120 A1 | 3/2006 | Levine et al. |
| 2006/0155310 A1 | 7/2006 | Binmoeller |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0178691 A1 | 8/2006 | Binmoeller |
| 2006/0206063 A1 | 9/2006 | Kagan et al. |
| 2006/0206064 A1 | 9/2006 | Kagan et al. |
| 2006/0249165 A1 | 11/2006 | Silverman et al. |
| 2006/0258906 A1 | 11/2006 | Binmoeller |
| 2006/0265082 A1 | 11/2006 | Meade et al. |
| 2006/0282087 A1 | 12/2006 | Binmoeller |
| 2006/0293742 A1 | 12/2006 | Dann et al. |
| 2007/0004963 A1 | 1/2007 | Benchetrit |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0021761 A1 | 1/2007 | Phillips |
| 2007/0027548 A1 | 2/2007 | Levine et al. |
| 2007/0032702 A1 | 2/2007 | Ortiz |
| 2007/0032879 A1 | 2/2007 | Levine et al. |
| 2007/0038308 A1 | 2/2007 | Geitz |
| 2007/0060932 A1 | 3/2007 | Stack et al. |
| 2007/0078302 A1 | 4/2007 | Ortiz et al. |
| 2007/0083271 A1 | 4/2007 | Levine et al. |
| 2007/0100367 A1 | 5/2007 | Quijano et al. |
| 2007/0118158 A1 | 5/2007 | Deem et al. |
| 2007/0118159 A1 | 5/2007 | Deem et al. |
| 2007/0135825 A1 | 6/2007 | Binmoeller |
| 2007/0167963 A1 | 7/2007 | Deem et al. |
| 2007/0198074 A1 | 8/2007 | Dann et al. |
| 2007/0203517 A1 | 8/2007 | Williams et al. |
| 2007/0213740 A1 | 9/2007 | Deem et al. |
| 2007/0213748 A1 | 9/2007 | Deem et al. |
| 2007/0213751 A1 | 9/2007 | Scirica et al. |
| 2007/0213837 A1 | 9/2007 | Ferreri et al. |
| 2007/0219570 A1 | 9/2007 | Deem et al. |
| 2007/0239284 A1 | 10/2007 | Skerven et al. |
| 2007/0250083 A1 | 10/2007 | Deem et al. |
| 2007/0250132 A1 | 10/2007 | Burnett |
| 2007/0265709 A1 | 11/2007 | Rajan et al. |
| 2007/0276432 A1 | 11/2007 | Stack et al. |
| 2007/0282349 A1 | 12/2007 | Deem et al. |
| 2007/0282418 A1 | 12/2007 | Weitzner |
| 2007/0282452 A1 | 12/2007 | Weitzner et al. |
| 2007/0282453 A1 | 12/2007 | Weitzner et al. |
| 2007/0282454 A1 | 12/2007 | Krueger et al. |
| 2007/0293885 A1 | 12/2007 | Binmoeller |
| 2008/0033574 A1* | 2/2008 | Bessler et al. ............. 623/23.68 |
| 2008/0045803 A1 | 2/2008 | Williams et al. |
| 2008/0065122 A1 | 3/2008 | Stack et al. |
| 2008/0065136 A1 | 3/2008 | Young |
| 2008/0071383 A1 | 3/2008 | Levine et al. |
| 2008/0086214 A1 | 4/2008 | Hardin et al. |
| 2008/0092910 A1 | 4/2008 | Brooks |
| 2008/0097466 A1 | 4/2008 | Levine et al. |
| 2008/0103604 A1 | 5/2008 | Levine et al. |
| 2008/0109086 A1 | 5/2008 | Voegele et al. |
| 2008/0109087 A1 | 5/2008 | Durgin |
| 2008/0140172 A1* | 6/2008 | Carpenter et al. ............. 623/1.2 |
| 2008/0161935 A1 | 7/2008 | Albrecht et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0167724 A1 | 7/2008 | Ruane et al. |
| 2008/0183238 A1 | 7/2008 | Chen |
| 2008/0195225 A1 | 8/2008 | Silverman et al. |
| 2008/0195226 A1 | 8/2008 | Williams et al. |
| 2008/0208135 A1 | 8/2008 | Annunziata |
| 2008/0208161 A1 | 8/2008 | Kaji et al. |
| 2008/0208224 A1 | 8/2008 | Surti et al. |
| 2008/0208239 A1 | 8/2008 | Annunziata |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221597 A1 | 9/2008 | Wallace et al. |
| 2008/0221702 A1 | 9/2008 | Wallace et al. |
| 2008/0234834 A1 | 9/2008 | Meade et al. |
| 2008/0243151 A1 | 10/2008 | Binmoeller et al. |
| 2008/0249533 A1 | 10/2008 | Godin |
| 2008/0249566 A1 | 10/2008 | Harris et al. |
| 2008/0249635 A1 | 10/2008 | Weitzner et al. |
| 2008/0255476 A1 | 10/2008 | Boyajian et al. |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0262529 A1 | 10/2008 | Jacques |
| 2008/0269715 A1 | 10/2008 | Faller et al. |
| 2008/0269797 A1* | 10/2008 | Stack ....................... A61F 2/04 606/198 |
| 2008/0287969 A1 | 11/2008 | Tsonton et al. |
| 2008/0312559 A1 | 12/2008 | Santilli et al. |
| 2008/0319455 A1 | 12/2008 | Harris et al. |
| 2009/0005637 A1 | 1/2009 | Chin et al. |
| 2009/0012541 A1 | 1/2009 | Dahl et al. |
| 2009/0012542 A1 | 1/2009 | N'diaye et al. |
| 2009/0012544 A1 | 1/2009 | Thompson et al. |
| 2009/0012553 A1 | 1/2009 | Swain et al. |
| 2009/0076588 A1 | 3/2009 | Weber |
| 2009/0093767 A1 | 4/2009 | Kelleher |
| 2009/0093839 A1 | 4/2009 | Kelleher |
| 2009/0118749 A1 | 5/2009 | Shalon et al. |
| 2009/0125119 A1 | 5/2009 | Obermiller et al. |
| 2009/0138094 A1 | 5/2009 | Schurr |
| 2009/0149871 A9 | 6/2009 | Kagan et al. |
| 2009/0164028 A1 | 6/2009 | Chen |
| 2009/0177215 A1 | 7/2009 | Stack et al. |
| 2009/0182355 A1 | 7/2009 | Levine et al. |
| 2009/0187206 A1 | 7/2009 | Binmoeller et al. |
| 2009/0198210 A1 | 8/2009 | Burnett et al. |
| 2009/0216262 A1 | 8/2009 | Burnett et al. |
| 2009/0240105 A1 | 9/2009 | Smit et al. |
| 2009/0240340 A1 | 9/2009 | Levine et al. |
| 2009/0248171 A1 | 10/2009 | Levine et al. |
| 2009/0276055 A1 | 11/2009 | Harris et al. |
| 2009/0281379 A1 | 11/2009 | Binmoeller et al. |
| 2009/0299486 A1 | 12/2009 | Shohat et al. |
| 2009/0299487 A1 | 12/2009 | Stack et al. |
| 2009/0326433 A1 | 12/2009 | Albrecht et al. |

(56) References Cited

U.S. PATENT DOCUMENTS

| | | |
|---|---|---|
| 2009/0326675 A1 | 12/2009 | Albrecht et al. |
| 2010/0004755 A1 | 1/2010 | Imran |
| 2010/0016988 A1 | 1/2010 | Stack et al. |
| 2010/0030017 A1 | 2/2010 | Baker et al. |
| 2010/0135971 A1 | 6/2010 | Schiffrin |
| 2010/0256775 A1 | 10/2010 | Belhe et al. |
| 2010/0305590 A1 | 12/2010 | Holmes et al. |
| 2011/0009690 A1 | 1/2011 | Belhe et al. |
| 2011/0104327 A1 | 5/2011 | Kirejevas |
| 2011/0106273 A1 | 5/2011 | Belhe et al. |
| 2012/0065571 A1 | 3/2012 | Thompson et al. |
| 2012/0109188 A1 | 5/2012 | Viola |
| 2012/0184893 A1 | 7/2012 | Thompson et al. |
| 2012/0232460 A1 | 9/2012 | Raven et al. |
| 2012/0253260 A1 | 10/2012 | Belhe et al. |
| 2012/0302936 A1 | 11/2012 | Belhe et al. |
| 2013/0030351 A1 | 1/2013 | Belhe et al. |
| 2013/0324907 A1 | 12/2013 | Huntley et al. |
| 2014/0194806 A1 | 7/2014 | Belhe et al. |
| 2014/0200502 A1 | 7/2014 | Belhe et al. |
| 2014/0309576 A1 | 10/2014 | Belhe et al. |
| 2014/0350694 A1 | 11/2014 | Behan |
| 2014/0379093 A1 | 12/2014 | Durgin |
| 2016/0089256 A1 | 3/2016 | Belhe et al. |
| 2016/0228276 A1 | 8/2016 | Thompson et al. |

FOREIGN PATENT DOCUMENTS

| | | |
|---|---|---|
| CN | 1575155 A | 2/2005 |
| CN | 1618411 A | 5/2005 |
| EP | 0137878 A1 | 4/1985 |
| EP | 1420730 A2 | 5/2004 |
| EP | 1492477 A1 | 1/2005 |
| EP | 1492478 A1 | 1/2005 |
| EP | 1555970 A1 | 7/2005 |
| EP | 1569582 A2 | 9/2005 |
| EP | 1585458 A1 | 10/2005 |
| EP | 1680054 A1 | 7/2006 |
| EP | 1708641 A1 | 10/2006 |
| EP | 1708655 A1 | 10/2006 |
| EP | 1709508 A2 | 10/2006 |
| EP | 1749482 A2 | 2/2007 |
| EP | 1750595 A2 | 2/2007 |
| EP | 1778069 A1 | 5/2007 |
| EP | 1786310 A2 | 5/2007 |
| EP | 1799145 A1 | 6/2007 |
| EP | 1817072 A2 | 8/2007 |
| EP | 1832250 A1 | 9/2007 |
| EP | 1850811 A1 | 11/2007 |
| EP | 1850812 A1 | 11/2007 |
| EP | 1881781 A2 | 1/2008 |
| EP | 1887995 A2 | 2/2008 |
| EP | 1895887 A2 | 3/2008 |
| EP | 1937164 A1 | 7/2008 |
| EP | 1992314 A1 | 11/2008 |
| EP | 1416861 B1 | 12/2008 |
| EP | 1749480 B1 | 12/2008 |
| EP | 2010270 A2 | 1/2009 |
| EP | 1610720 B1 | 2/2009 |
| EP | 2023828 A2 | 2/2009 |
| EP | 2026713 A2 | 2/2009 |
| EP | 2061397 A1 | 5/2009 |
| EP | 2066243 A1 | 6/2009 |
| EP | 2068719 A2 | 6/2009 |
| EP | 2080242 A2 | 7/2009 |
| EP | 1520528 B1 | 9/2009 |
| EP | 1610719 B1 | 1/2010 |
| EP | 1603488 B1 | 4/2010 |
| EP | 1585460 B1 | 5/2010 |
| EP | 1933721 B1 | 5/2010 |
| EP | 1768618 B1 | 4/2011 |
| EP | 1883370 B1 | 8/2011 |
| EP | 2945566 A1 | 11/2015 |
| JP | 2005500127 A | 1/2005 |
| JP | 2007513684 A | 5/2007 |
| JP | 2007513685 A1 | 5/2007 |
| WO | WO1998049943 A2 | 11/1998 |
| WO | WO2002096327 A2 | 12/2002 |
| WO | WO2003017882 A2 | 3/2003 |
| WO | WO2003086246 A1 | 10/2003 |
| WO | WO2003086247 A1 | 10/2003 |
| WO | WO2003094785 A1 | 11/2003 |
| WO | WO2004011085 A1 | 2/2004 |
| WO | WO2004017863 A2 | 3/2004 |
| WO | WO2004041133 A1 | 5/2004 |
| WO | WO2004064680 A1 | 8/2004 |
| WO | WO2004064685 A1 | 8/2004 |
| WO | WO2004087014 A2 | 10/2004 |
| WO | WO2004087233 A2 | 10/2004 |
| WO | WO2004049982 B1 | 12/2004 |
| WO | WO2005037152 A1 | 4/2005 |
| WO | WO2005058415 A2 | 6/2005 |
| WO | WO2005060869 A2 | 7/2005 |
| WO | WO2005060882 A1 | 7/2005 |
| WO | WO2005065412 A2 | 7/2005 |
| WO | WO2005097012 A2 | 10/2005 |
| WO | WO2005099591 A2 | 10/2005 |
| WO | WO2005110244 A1 | 11/2005 |
| WO | WO2005110280 A2 | 11/2005 |
| WO | WO2005112822 A1 | 12/2005 |
| WO | WO2005120363 A1 | 12/2005 |
| WO | WO2006014496 A2 | 2/2006 |
| WO | WO2006016894 A1 | 2/2006 |
| WO | WO2006020370 A2 | 2/2006 |
| WO | WO2006028898 A2 | 3/2006 |
| WO | WO2006034062 A1 | 3/2006 |
| WO | WO2006060049 A2 | 6/2006 |
| WO | WO2006062996 A2 | 6/2006 |
| WO | WO2006078781 A1 | 7/2006 |
| WO | WO2006078927 A1 | 7/2006 |
| WO | WO2006102012 A1 | 9/2006 |
| WO | WO2006102240 A2 | 9/2006 |
| WO | WO2006124880 A2 | 11/2006 |
| WO | WO2006127593 A2 | 11/2006 |
| WO | WO2006133311 A2 | 12/2006 |
| WO | WO2007019117 A1 | 2/2007 |
| WO | WO2007030829 A2 | 3/2007 |
| WO | WO2007038715 A1 | 4/2007 |
| WO | WO2007041598 A1 | 4/2007 |
| WO | WO2007075396 A2 | 7/2007 |
| WO | WO2007092390 A2 | 8/2007 |
| WO | WO2007107990 A2 | 9/2007 |
| WO | WO 2007/136468 * 11/2007 ............ A61M 31/00 |
| WO | WO2007127209 A2 | 11/2007 |
| WO | WO2007136468 A2 | 11/2007 |
| WO | WO2007139920 A2 | 12/2007 |
| WO | WO2007142829 A1 | 12/2007 |
| WO | WO2007142832 A1 | 12/2007 |
| WO | WO2007142833 A1 | 12/2007 |
| WO | WO2007142834 A1 | 12/2007 |
| WO | WO2007145684 A2 | 12/2007 |
| WO | WO2008005510 A2 | 1/2008 |
| WO | WO2008030403 A1 | 3/2008 |
| WO | WO2008033409 A1 | 3/2008 |
| WO | WO2008033474 A2 | 3/2008 |
| WO | WO2008039800 A2 | 4/2008 |
| WO | WO2008101048 A2 | 8/2008 |
| WO | WO2008106041 A1 | 9/2008 |
| WO | WO2008106279 A1 | 9/2008 |
| WO | WO2008112942 A2 | 9/2008 |
| WO | WO2008127552 A2 | 10/2008 |
| WO | WO2008141288 A1 | 11/2008 |
| WO | WO2008148047 A2 | 12/2008 |
| WO | WO2008150905 A1 | 12/2008 |
| WO | WO2008154450 A1 | 12/2008 |
| WO | WO2008154594 A2 | 12/2008 |
| WO | WO2009011881 A2 | 1/2009 |
| WO | WO2009011882 A2 | 1/2009 |
| WO | WO2009012335 A1 | 1/2009 |
| WO | WO2009036244 A1 | 3/2009 |
| WO | WO2009046126 A1 | 4/2009 |
| WO | WO2009082710 A1 | 7/2009 |
| WO | WO2009085107 A1 | 7/2009 |
| WO | WO2009086549 A1 | 7/2009 |

(56) References Cited

FOREIGN PATENT DOCUMENTS

| | | |
|---|---|---|
| WO | WO2009097582 A1 | 8/2009 |
| WO | WO2009097585 A1 | 8/2009 |
| WO | WO2010115011 A1 | 10/2010 |
| WO | WO2011062882 A1 | 5/2011 |
| WO | WO2011073970 A1 | 6/2011 |
| WO | WO2011099940 A8 | 8/2011 |
| WO | WO2012103531 A2 | 8/2012 |
| WO | 2014113483 A1 | 7/2014 |

OTHER PUBLICATIONS

Buchwald, Henry et al., "Bariatric Surgery: A Systematic Review and Meta-Analysis", JAMA, Oct. 13, 2004, 292(14), pp. 1724-1737.
Cummings, David E. et al., "Role of the bypassed proximal intestine in the anti-diabetic effects of bariatric surgery", Surgery for Obesity and Related Diseases 3 2007, pp. 109-115.
International Search Report and Written Opinion issued in PCT/US2010/029648, dated Aug. 24, 2010.
International Search Report and Written Opinion issued in PCT/US2010/041574, dated Jan. 25, 2011.
International Search Report and Written Opinion issued in PCT/US2011/020560, dated Mar. 28, 2011, 10 pages.
International Search Report and Written Opinion issued in PCT/US2011/061193.
Invitation to Pay Additional Fees issued in PCT/US2010/029648, dated Jun. 1, 2010.
Pories, Walter J. et al., "Surgical Treatment of Obesity and its Effect on Diabetes: 10-6 Follow-up", Am J Clin Nutr 1992, 55, 582S-585S.
Pories, Walter J. et al., "Who Would Have Thought It? An Operation Proves to be the Most Effective Therapy for Adult-Onset Diabetes Mellitus", Annals of Survery, Sep. 1995, 222(3), pp. 339-352.
Rodriguez-Grunert, Leonardo et al., "First Human Experience With endoscopically Delivered and retrieved duodenal-jejunal bypass sleeve", Surgery for Obesity and Related diseases 4 (2008) 55-59.
Rubino, Francesco et al,, "Effect of Duodenal-Jejunal Exclusion in a Non-Obese Animal Model of Type 2 Diabetes", Annals of Surgery, vol. 239, No. 1, Jan. 2004, pp. 1-11.
Rubino, Francesco et al., "Potential of Surgery for Curing Type 2 Diabetes Mellitus", Annals of Surgery, Nov. 2002, 236(5), 554-559.
Rubino, Francesco et al., "The Mechanism of Diabetes Control After Gastrointestinal Bypass Surgery Reveals a Role of the Proximal Small Intestine in the pathophysiology of Type 2 Diabetes", Annals of Surgery, 244(5), Nov. 2006, pp. 741-749.
Strader, April et al., "Weight Loss Through Ileal transposition is accompanied by increased ileal hormone secretion and synthesis in rats", Am J Physiol Endocrinol Metab 288: E447-E453, 2005.
Troy, Stephanie et al., "Intestinal Gluconeogenesis is a key factor for early metabolic changes after gastric bypass but not after gastric lap-band in mice", Cell metabolism 8, 201-211, Sep. 3, 2008.
Vetter, Marion et al., "Narrative Review: Effect of bariatric Surgery on Type 2 Diabetes Mellitus", Annals of Internal Medicine, Jan. 20, 2009, 150(2), pp. 94-104.
International Search Report and Written Opinion issued in PCT/US12/58202, dated Jan. 23, 2013, 14 pages.
International Search Report and Written Opinion issued in PCT/US2014/011702, dated Mar. 21, 2014, 9 pages.
Schouten, Ruben et al., "A Multicenter, Randomized Efficacy Study of the endoBarrier Gastrointestinal Liner for Presurgical Weight Loss Prior to Bariatric Surgery", Annals of Surgery, vol. 251, No. 2, Feb. 2010, pp. 236-243.
Daniels, Stephen, "Probiotics may 'counter obesity and diabetes': NIH study", Jul. 10, 2013, downloaded from http://www.nutraingredients-usa.com/research/probiotics-may-counter-obesity-and-diabetes-NIH-study, 2 pages.
International Preliminary Report on Patentability issued in PCT/US2014/011702, dated Jul. 30, 2015, 7 pages.
International Search Report and Written Opinion issued in PCT/US2015/019730, dated Mar. 10, 2015, 15 pages.
Ley, Ruth E. et al., "Microbial ecology: human gut microbes associated with obesity", Nature, vol. 44, No. 7122, pp. 1022-1023, 2006.
Partial European Search Report issued in EP14172564, dated Feb. 12, 2015 , 7pages.
Yadav, Hariom et al., Beneficial Metabolic Effects of a Probiotic via Butyrate-induced GLP-1 Hormone Secretion, Journal of Biological Chemistry, 2013, vol. 288, pp. 25088-25097.
Better Nutrition: Your guide to Natural Living, Bouncing Back (http://www.betternutrition.com/natural-surgery-recovery-antiobiotics-probiotics/), Sep. 2009, accessed Jun. 14, 2016.
Gavitt et al., Probiotics Improve Outcomes After Roux-en-Y Gastric Bypass Surgery: A Prospective Randomized Trial, J Gastrointest Surg (2009) 13:1198-1204.
Preliminary Report on Patentability issued in PCT/US2015/019730 dated Sep. 22, 2016, 7 pages.
Supplemental European Search Report issued in EP Application 14740554 dated Sep. 26, 2016, 7 pages.
U.S. Appl. No. 15/060,418 entitled Pyloric Anchors and Methods for Intestinal Bypass Sleeves filed Mar. 3, 2016.

* cited by examiner

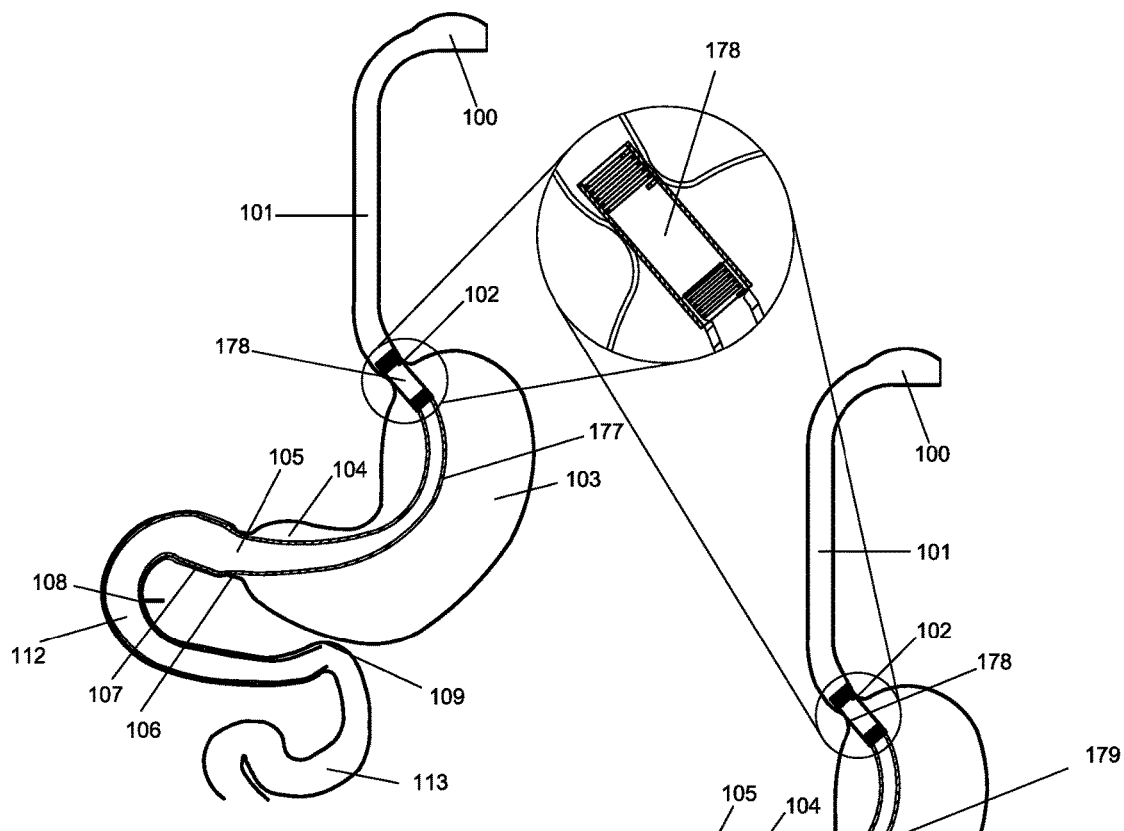
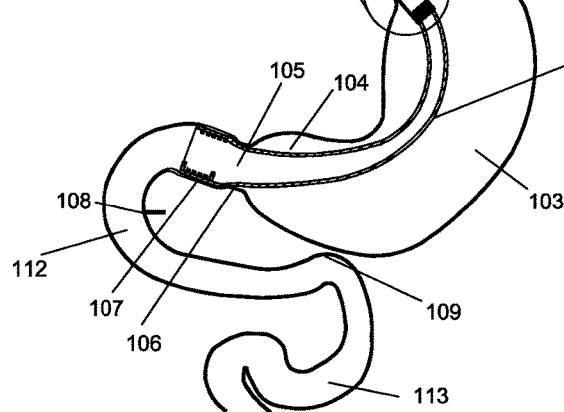
FIG. 22A
FIG. 22B

MODULAR GASTROINTESTINAL PROSTHESES

CROSS-REFERENCE TO RELATED APPLICATION

This application is a division of U.S. application Ser. No. 12/752,697, filed Apr. 1, 2010, entitled "Modular Gastrointestinal Prostheses", which claims the benefit under 35 U.S.C. § 119 of U.S. Provisional Application 61/211,853, filed on Apr. 3, 2009, entitled "Modular Systems for Intra-Luminal Therapies within Hollow Body Organs," which are incorporated herein by reference in their entirety for all purposes.

TECHNICAL FIELD

This invention relates to prosthetic implants placed within the gastrointestinal system, including the stomach, the esophagus and the intestines. In particular, it relates to implant systems having components implantable and removable using endoscopic techniques, for treatment of obesity, diabetes, reflux, and other gastrointestinal conditions.

BACKGROUND

Bariatric surgery procedures such as sleeve gastrectomy, the Rouen-Y gastric bypass (RYGB) and the bileo-pancreatic diversion (BPD) are surgical procedures to modify food intake and/or absorption within the gastrointestinal system to effect weight loss in obese patients. These procedures affect metabolic processes within the gastrointestinal system, by either short-circuiting certain natural pathways or creating different interaction between the consumed food, the digestive tract, its secretions and the neurohormonal system regulating food intake and metabolism. In the last few years there has been a growing clinical consensus, that obese diabetic patients who undergo bariatric surgery see a remarkable resolution of their Type-2 Diabetes Mellitus (T2DM) soon after the procedure. The remarkable resolution of diabetes after RYGB and BPD typically occurs too fast to be accounted for by weight loss alone, suggesting that there may be a direct impact on glucose homeostasis. The mechanism of this resolution of T2DM is not well understood, and it is quite likely that multiple mechanisms are involved.

One of the drawbacks of bariatric surgical procedures is that they require fairly invasive surgery, with potentially serious complications and long patient recovery periods. In recent years, there is an increasing amount of ongoing effort to develop minimally invasive procedures to mimic the effects of bariatric surgery using minimally invasive procedures. One such procedure involves the use of gastrointestinal implants that modify transport and absorption of food and organ secretions. For example, U.S. Pat. No. 7,476,256 describes an implant having a tubular sleeve with an anchor having barbs. While these implants may be delivered endoscopically, the implants offer the physician limited flexibility and are not readily removable or replaceable, as the entire implant is subject to tissue in-growth after implantation. Moreover, stents with active fixation means, such as barbs that penetrate in to the surrounding tissue, may potentially cause tissue necrosis and erosion of the implants through the tissue, which can lead to serious complications such as systemic infection.

SUMMARY

According to various embodiments, the present invention is a modular intra-luminal implant systems for treating metabolic disorders such as obesity and diabetes, which provides far more flexible therapy alternatives than single devices to treat these disorders. These implant systems include components that can be selectively added or removed to mimic a variety of bariatric surgical procedures with a single basic construct. The fundamental building blocks of the system include anchoring implants that are placed within the GI system or some instances around particular organs. These low-profile implants are designed for long-term performance with minimal interference with normal physiological processes. Features of these anchoring implants allow them to act as docking stations for therapy implants designed for achieving certain metabolic modification goals. By using a combination of anchoring implants with corresponding replaceable tubular elements that dock with them, it is possible to design therapies with particular metabolic modification goals or those that mimic currently practiced bariatric surgical procedures. This allows the physician to customize the therapy to the patient at the time of the initial procedure but also allows the flexibility to alter the therapy during the life-time of the patient by replacing individual components.

According to some embodiments, the modular systems of the invention includes a anchoring implant portion (docking element) including an expandable structure (e.g., a low profile stent or ring or fabric/elastomeric cuff) anchored within the esophagus, the gastro-esophageal junction, the pyloric junction, the duodenum or the jejunum and may have sleeve or graft extensions. The stents may be balloon expandable or self-expanding and anchor against the tissue with radial force. The rings could be made of self-expanding Nitinol and anchor to the tissue by entrapment of the tissue within the ring elements or by radial force. The cuffs could be either sutured or stapled or permanently or reversibly attached by other mechanical means to the tissue. The anchoring implant includes or is adapted to receive (e.g., endoscopically) features that enable docking functionality. The docking functionality of the stent, ring or cuff, for example, could take the form of magnetic elements, hooks, mating mechanical elements or structures (such as the stent braid or mesh) that are integral to the framework of the stent, ring or cuff or the sleeve or graft extension. The system also could be such that the docking functionality is not integral to the stent, ring or cuff but is introduced later by attaching other elements such as magnets, hooks, mating mechanical elements etc to the framework of the stent, ring, cuff or to the sleeve/graft extension of the above implants. Therapeutic implants, such as tubular sleeves or stent grafts are adapted to be reversibly attached to the anchoring implants. These therapeutic implants will have corresponding features (e.g., magnets, hooks, mechanical elements) to enable docking to the anchoring implants, so that the therapeutic implants can be reversibly attached to the anchoring implants. In some embodiments, the tubular implants will not be in contact with tissue to minimize or prevent tissue in-growth and facilitate easy removal with endoscopic instrumentation after long-term implantation.

According to various embodiments, the anchoring or docking implants comprise stents or covered stents (stent grafts) that promote tissue in-growth without penetrating into the tissue. Such stents may include, for example, a self-expanding laser cut stent with non-penetrating struts that engage the wall of the GI tract or a self-expanding stent braided with a Dacron type fabric covering of the right porosity would promote tissue in-growth and aid fixation.

According to various embodiments, the anchoring or docking implants comprise a double braided stent (e.g., having a spacing between the braids of 0.5 to 5.0 mm). This embodiment is optimized such that the outer braid could be securely anchored within tissue, but the tissue would not grow into the inner braid, which can then be used to anchor the replaceable implant.

According to various embodiments, the anchoring or docking implants are specifically designed to be constrained at certain anatomic locations. Such designs, for example, may include a double-flange shaped or dumbbell-shaped implants placed at the pyloric junction or barrel shaped stents placed within the duodenal bulb.

According to various embodiments, the replaceable therapeutic implants that dock to the anchoring implants take the form of long tubes that can selectively channel the flow of food and secretions from organs (e.g., the stomach, gall bladder, intestines and pancreas) to various destinations within the digestive tract. This diversion and bypass of food and organ secretions (e.g., insulin and incretin from the pancreas and bile from the gall bladder) could then be controlled by adjusting the design features of the system where the implants are placed within the GI tract. The implants could also include restrictive stoma type elements or anti-reflux valves. To divert food and secretions from the first part of the intestine, for example, an anchoring implant can be placed within the duodenal bulb or at the pyloric junction. Then, a thin tube about 1-2 feet in length with a funnel shaped proximal end and a rigid ring shaped distal end can be introduced into the proximal duodenum and docked to the permanent implant. It would be possible to later remove this by endoscopic means by simple undocking it from the anchoring implant. To restrict passage of food, a restrictive element such as one created by a tapered stepped tube or a stent or a stent graft can become the docking element and be reversibly attached to the docking station.

According to various embodiments, the docking means may include engaging/disengaging mechanical shape memory and super-elastic elements, attractive/repulsive and levitating magnetic mechanisms, loop-hoop fastener technologies etc. The systems may be deployed with functional docking components or those components would be attached to the permanent implants under endoscopic visual guidance. The docking means is designed so that the therapeutic implants can be easily deployed and securely affixed to the anchoring implants. According to various embodiment, the engaging elements of the docking system are arranged so that they do not impinge on the surrounding tissue, nor would be later covered with tissue layers. This facilitates disengaging the tubular sleeve elements from the stent with simple magnetic instruments or grasper type endoscopic instruments or funnel shaped retrieval basket catheters or using a draw-string type mechanism.

According to some embodiments, the anchoring element is integrated with a therapy component.

According to various embodiments, the present invention is a method of treating gastro-esophageal reflux disease (GERD) including placing a low-profile implant within the stomach, the esophagus, the intestine or at internal junctions of these organs or around these organs, and securely attaching to the implant other gastro-intestinal implants that permit bypass of food and organ secretions from one site within the gastro-intestinal tract to other sites within the gastro-intestinal tract.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 22A is a sectional view of a portion of the digestive tract in the body. A docking element is implanted in the esophagus at the gastro-esophageal junction. A second docking element and tubular implant is implanted from the esophageal implant to the ligament of treitz.

FIG. 22B is a sectional view of a portion of the digestive tract in the body. A docking element is implanted in the esophagus at gastro-esophageal junction. A docking element and tubular implant is implanted from the esophageal implant to the duodenal bulb.

FIG. 55 shows another docking element designed where the stomach side of docking element is more disk-like.

Figure 1:
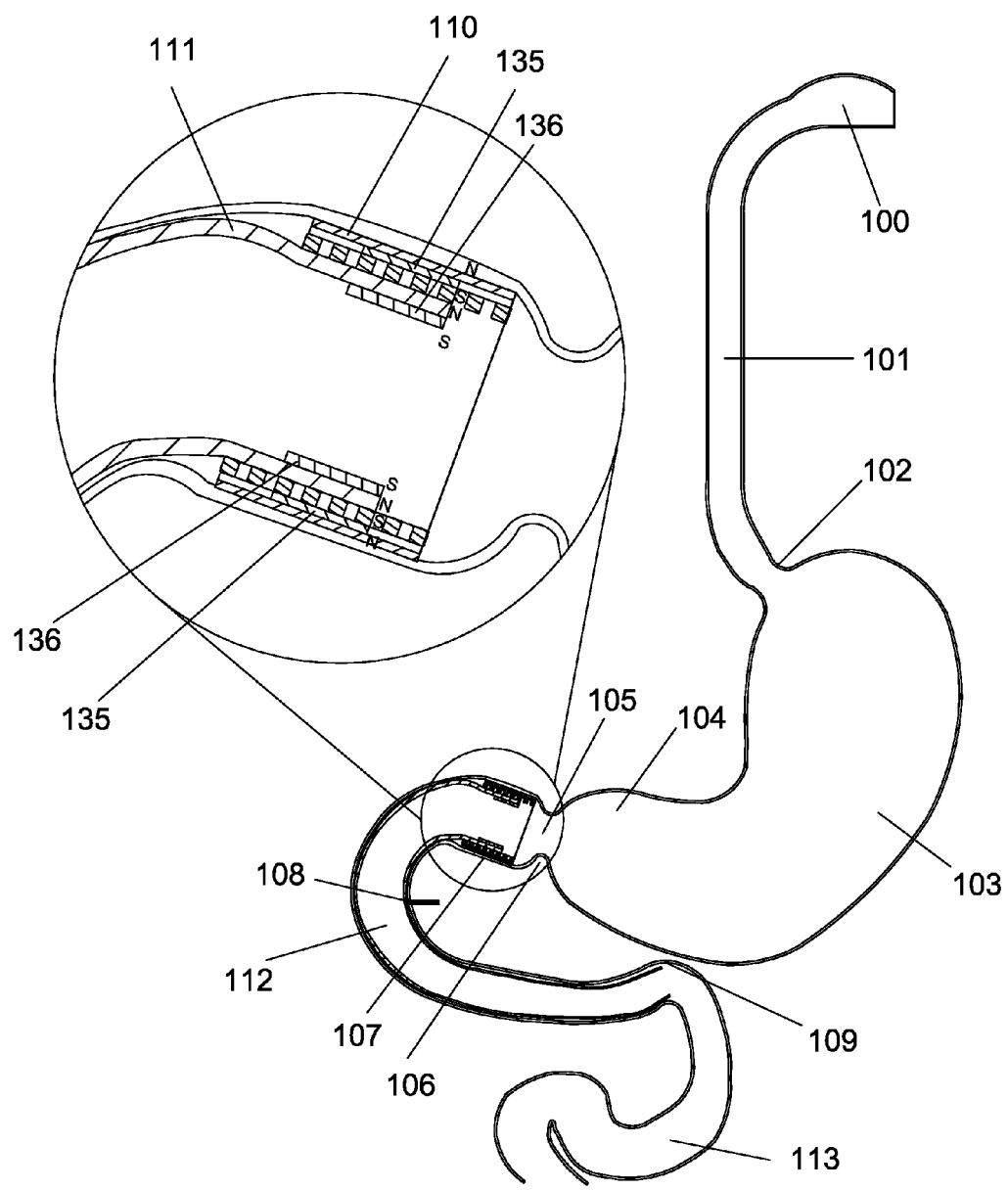
FIG. 1 is a cross sectional view of a portion of the digestive tract in the body. A docking element is implanted in the duodenal bulb and a tubular implant (sleeve) is attached to the docking element and extended into the duodenum to the ligament of treitz.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims

DETAILED DESCRIPTION

FIG. 1 is a schematic, sectional view of an embodiment of the invention implanted in a portion of a human digestive tract. As a person ingests food, the food enters the mouth 100, is chewed, and then proceeds down the esophagus 101 to the lower esophageal sphincter at the gastro-esophageal junction 102 and into the stomach 103. The food mixes with enzymes in the mouth 100 and in the stomach 103. The stomach 103 converts the food to a substance called chyme. The chyme enters the pyloric antrum 104 and exits the stomach 103 through the pylorus 106 and pyloric orifice 105. The small intestine is about 21 feet long in adults. The small intestine is comprised of three sections. The duodenum 112, jejunum 113 and ileum (not shown). The duodenum 112 is the first portion of the small intestine and is typically 10-12 inches long. The duodenum 112 is comprised of four sections: the superior, descending, horizontal and ascending. The duodenum 112 ends at the ligament of treitz 109. The papilla of vater 108 is the duct that delivers bile and pancreatic enzymes to the duodenum 112. The duodenal bulb 107 is the portion of the duodenum which is closest to the stomach 103.

As shown in FIG. 1, a docking or anchoring element 110 is implanted in the duodenal bulb 107 and a tubular or therapy implant 111 is attached to the docking element and extended into the duodenum 112 to the ligament of treitz 109. In this embodiment, magnets 135 on the docking element 110 and magnets 136 on the tubular implant 111 are magnetically attracted to each other and thereby secure the docking element 110 to the therapy implant 111. According to various exemplary embodiments, the anchoring element 110 includes an expandable structure (e.g., a stent or ring) adapted for anchoring within the duodenal bulb and has a diameter of between about 20 and about 40 mm in its unrestrained expanded configuration. In these embodiments, the magnets 135 on the docking or anchoring element 110 serve as a docking feature for releasably coupling with the magnets 136 of the tubular implant 111.

Figure 2:
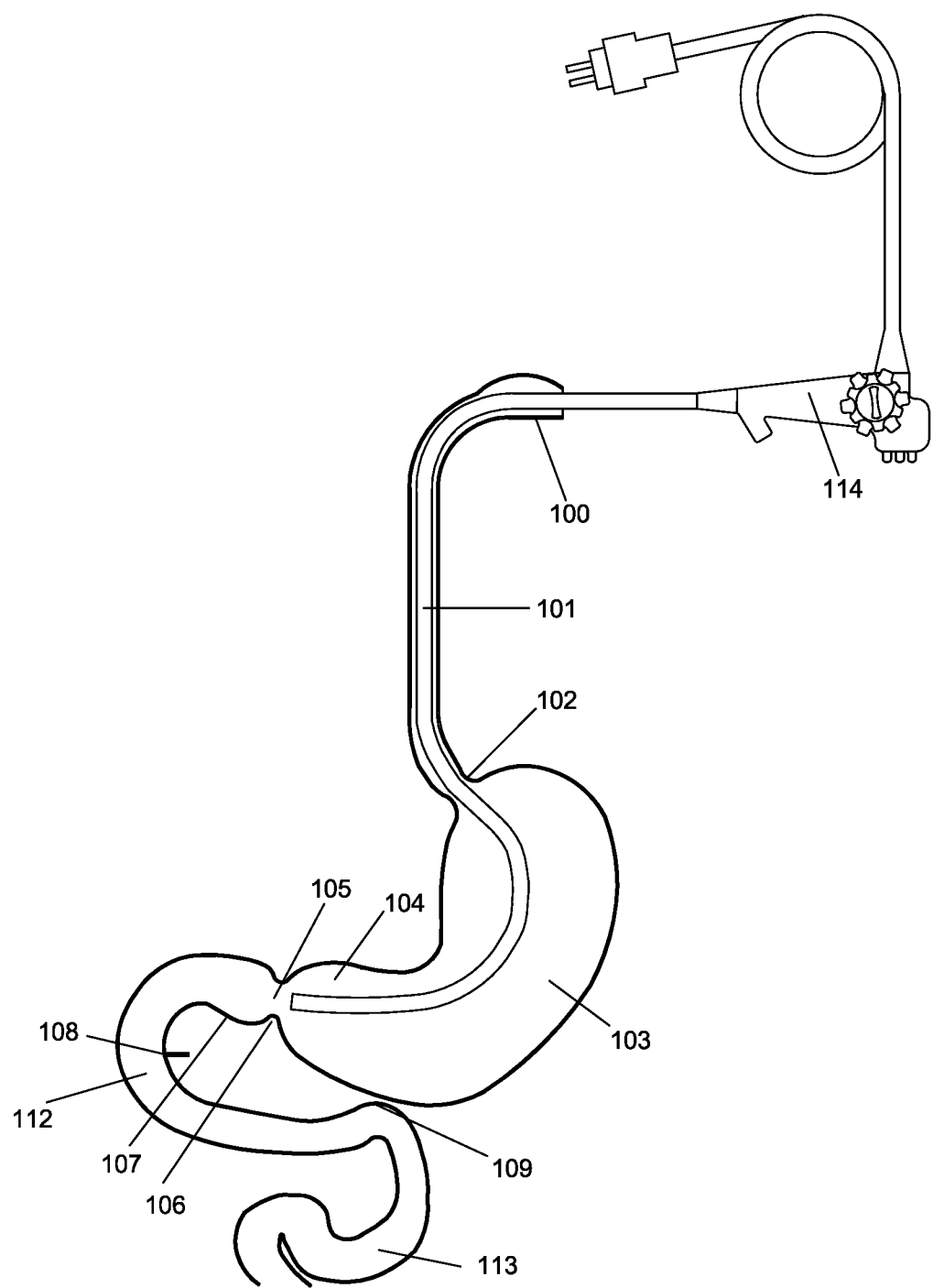
FIG. 2 is a cross sectional view of a portion of the digestive tract in the body. An endoscope is inserted into the mouth, passing through the esophagus in to the stomach and the end of the scope is pointed to allow viewing of the pylorus.

FIG. 2 is a schematic view of a portion of the digestive tract in a human body. An endoscope 114 has been inserted through the mouth 100, esophagus 101, the gastro-esophageal junction 102 and into the stomach 103. The endoscope 114 further extends into the pyloric antrum 104 to allow visualization of the pylorus 106.

Figure 3:
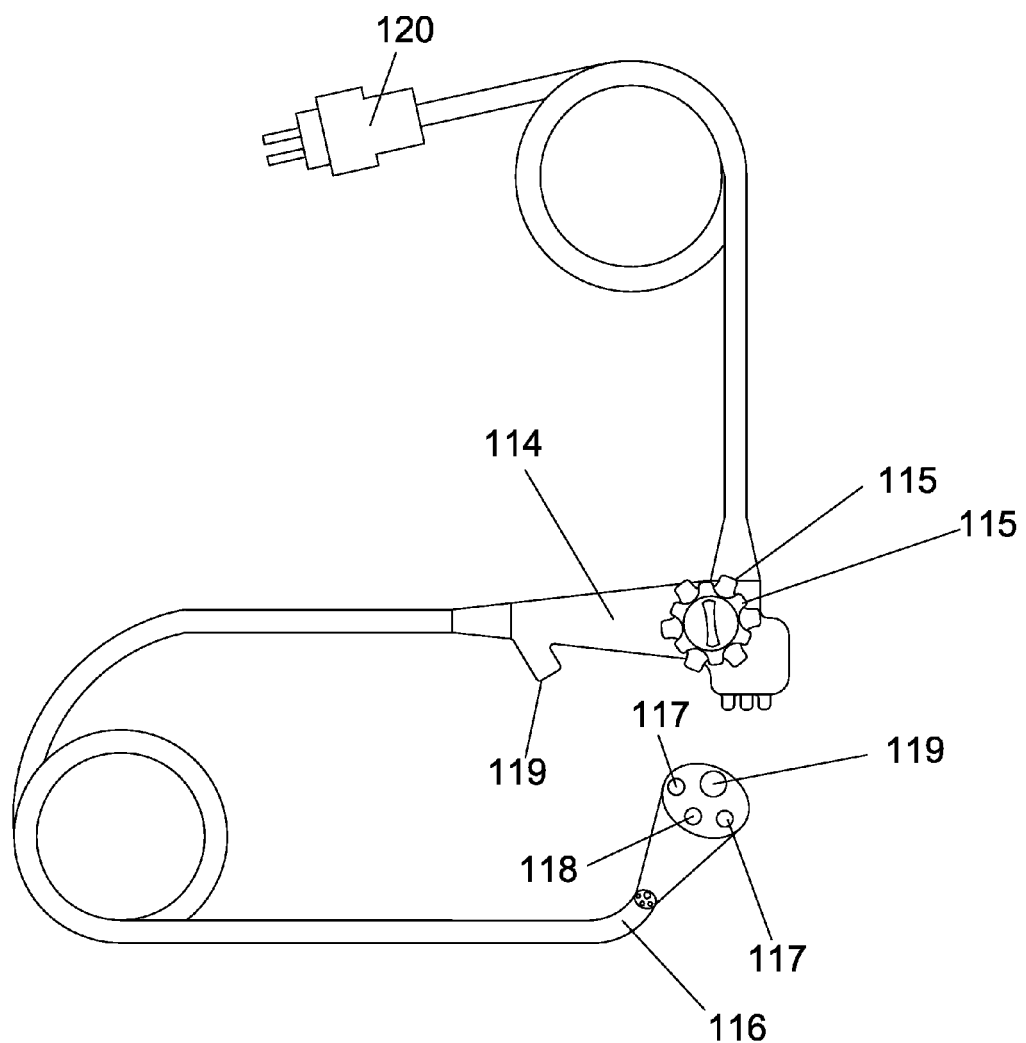
FIG. 3 is a drawing of a typical endoscope used for diagnostic and therapeutic procedures in the gastro intestinal (GI) tract.

FIG. 3 is a drawing of an endoscope 114. Endoscopes 114 are commonly used for diagnostic and therapeutic procedures in the gastrointestinal (GI) tract. The typical endoscope 114 is steerable by turning two rotary dials 115 to cause deflection of the working end 116 of the endoscope. The working end of the endoscope 116 or distal end, typically contains two fiber bundles for lighting 117, a fiber bundle for imaging 118 (viewing) and a working channel 119. The working channel 119 can also be accessed on the proximal end of the endoscope. The light fiber bundles and the image fiber bundles are plugged into a console at the plug in connector 120. The typical endoscope has a working channel, for example, having a diameter in the 2 to 4 mm diameter range. It may, for example having a working channel having a diameter in the 2.6 to 3.2 mm range. The outside diameter of the endoscopes are typically in the 8 to 12 mm diameter range depending on whether the endoscope is for diagnostic or therapeutic purposes.

Figure 4A:
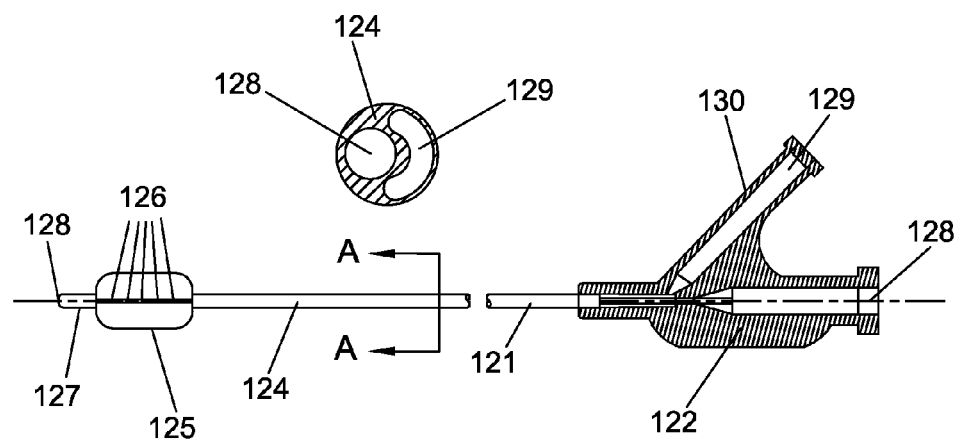
FIG. 4A is a drawing of an over the wire sizing balloon that can be used to measure the diameter of the pylorus, duodenal bulb, esophagus, pyloric antrum or other lumen in the GI tract.

FIG. 4A is a partial sectional view of an over the wire sizing balloon 121 that is used to measure the diameter of the pylorus 106, duodenal bulb 107, esophagus 102, pyloric antrum 104 or other lumen in the GI tract. The sizing balloon is composed of the following elements: a proximal hub 122, a catheter shaft 124, a distal balloon component 125, radiopaque marker bands 126, a distal tip 127, a guide wire lumen 128, and an inflation lumen 129. The distal balloon component 125 can be made, for example, from silicone, silicone polyurethane copolymers, latex, nylon 12, PET (Polyethylene terphalate) Pebax (polyether block amide), polyurethane, polyethelene, polyester elastomer or other suitable polymer. The distal balloon component 125 can be molded into any desired shape, including for example a cylindrical shape, a dog bone shape, or a conical shape. The distal balloon component 125 can be made compliant or noncompliant. The distal balloon component 125 can be bonded to the catheter shaft 124 with glue, heat bonding, solvent bonding, laser welding or any suitable means. The catheter shaft can be made from silicone, silicone polyurethane copolymers, latex, nylon 12, PET (Polyethylene terphalate) Pebax (polyether block amide), polyurethane, polyethylene, polyester elastomer or other suitable polymer. Section A-A (shown at the top portion of FIG. 4A) is a cross section of the catheter shaft 124. The catheter shaft 124 is shown as a dual lumen extrusion with a guide wire lumen 128 and an inflation lumen 129. The catheter shaft 124 can also be formed from two coaxial single lumen round tubes in place of the dual lumen tubing. The balloon is inflated by attaching a syringe (not shown) to luer fitting side port 130. The sizing balloon accommodates a guidewire through the guidewire lumen from the distal tip 127 through the proximal hub 122. The sizing balloon 121 can be filled with a radiopaque dye to allow visualization and measurement of the size of the anatomy with a fluoroscope. In the embodiment of FIG. 4A, the sizing balloon 121 has two or more radiopaque marker bands 126 located on the catheter shaft to allow visualization of the catheter shaft and balloon position. The marker bands 126 also serve as fixed known distance reference point that can be measured to provide a means to calibrate and determine the balloon diameter with the use of the fluoroscope. The marker bands can be made from tantalum, gold, platinum, platinum iridium alloys or other suitable material.

Figure 4B:
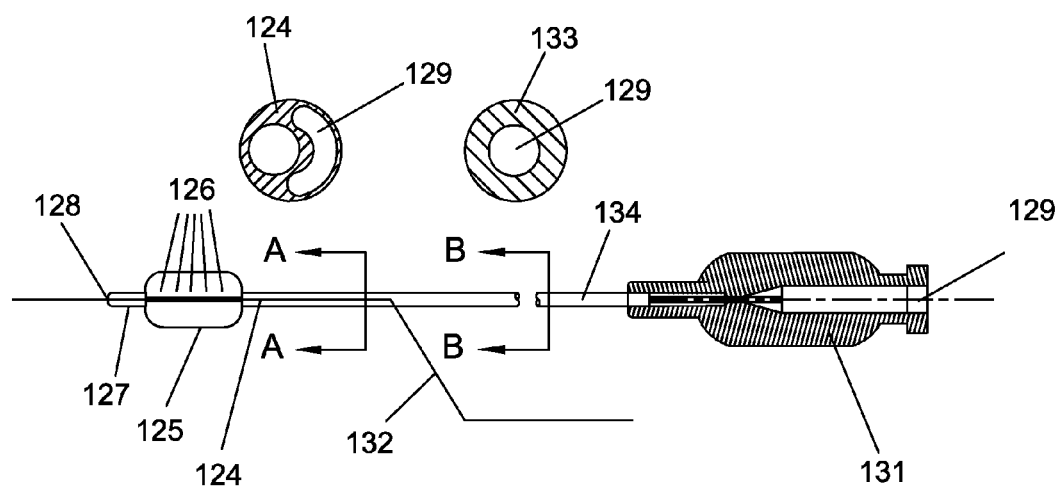
FIG. 4B is a drawing of a monorail sizing balloon that can be used to measure the diameter of the pylorus, duodenal bulb, esophagus, pyloric antrum or other lumen in the GI tract.

FIG. 4B is a partial sectional view of a rapid exchange sizing balloon 134 that is used to measure the diameter of the pylorus 106, duodenal bulb 107, esophagus 102, pyloric antrum 104 or other lumen in the GI tract. The sizing balloon is composed of the following elements: a proximal luer 131, a catheter shaft 124, a distal balloon component 125, radiopaque marker bands 126, a distal tip 127, a guide wire lumen 128, and an inflation lumen 129. The materials of construction will be similar to that of the sizing balloon 121 of FIG. 4A. The guide wire lumen 128 does not travel the full length of the catheter, it starts at the distal tip 127 and exist out the side of the catheter at distance shorter that that the shorter that the overall catheter length. A guide wire 132 is inserted into the balloon catheter to illustrate the guidewire path through the sizing balloon 134. As shown in FIG. 4B, the sizing balloon catheter shaft changes section along its length from a single lumen at section B-B 133 to a dual lumen at section A-A at 124.

Figure 5:
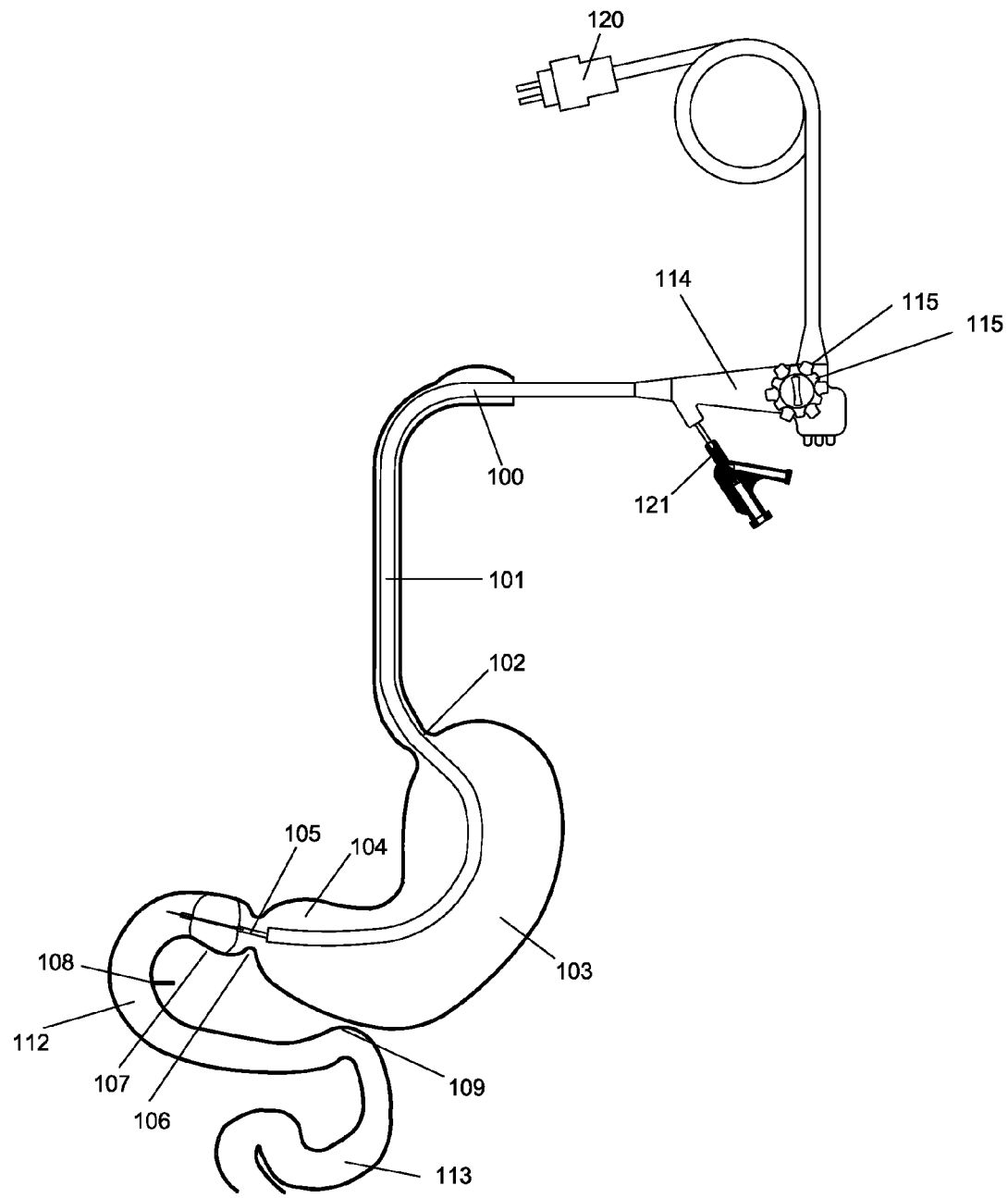
FIG. 5 is a sectional view of a portion of the digestive tract in the body. An endoscope is inserted into the GI tract up to the pylorus. A sizing balloon is inserted through the working channel and into the area of the duodenal bulb. The balloon is inflated to measure the diameter of the duodenal bulb.

FIG. 5 is a schematic view of a portion of the digestive tract in the body. An endoscope 114 is inserted into the GI tract up to the pylorus 106. A sizing balloon 121 is inserted through the working channel 119 of the endoscope and into the area of the duodenal bulb 107. The sizing balloon 121 is inflated with contrast agent. The diameter of the duodenal bulb 107 is measured with a fluoroscope.

Figure 6A:
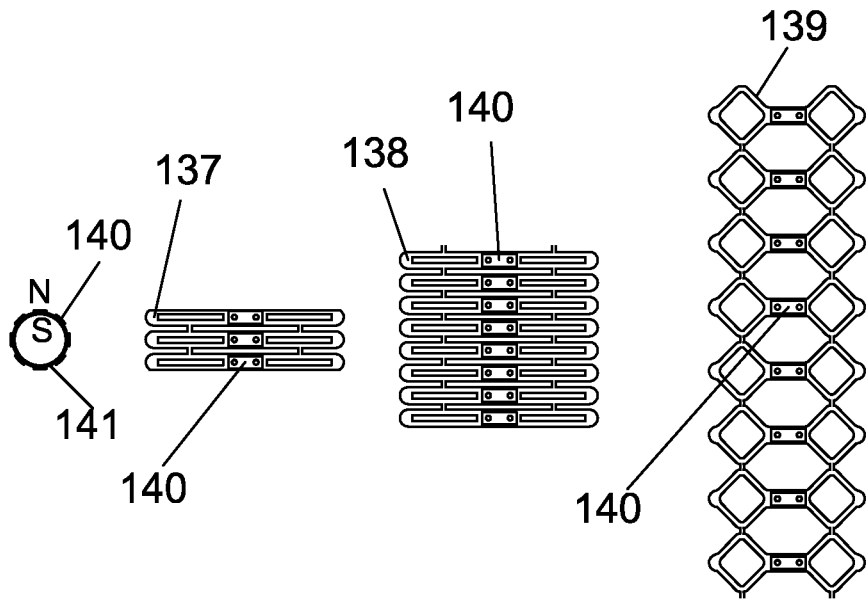
FIG. 6A is a drawing of a stent that can used as a docking element.

FIG. 6A shows various views of a stent that can used as a docking or anchoring element. The stents of this invention can be comprised, for example, of any one or more of the following materials: Nickel titanium alloys (Nitinol), Stainless steel alloys: 304, 316L, BioDur® 108 Alloy, Pyromet Alloy® CTX-909, Pyromet® Alloy CTX-3, Pyromet® Alloy 31, Pyromet® Alloy CTX-1, 21Cr-6Ni-9Mn Stainless, 21Cr-6Ni-9Mn Stainless, Pyromet Alloy 350, 18Cr-2Ni-12Mn Stainless, Custom 630 (17Cr-4Ni) Stainless, Custom 465® Stainless, Custom 455® Stainless Custom 450® Stainless, Carpenter 13-8 Stainless, Type 440C Stainless, Cobalt chromium alloys-MP35N, Elgiloy, L605, Biodur® Carpenter CCM alloy, Titanium and titanium alloys, Ti-6Al-4V/ELI and Ti-6Al-7Nb, Ti-15Mo Tantalum, Tungsten and tungsten alloys, Pure Platinum, Platinum-Iridium alloys, Platinum-Nickel alloys, Niobium, Iridium, Conichrome, Gold and Gold alloys. The stent may also be comprised of the following absorbable metals: Pure Iron and magnesium alloys. The stent may also be comprised of the following plastics: Polyetheretherketone (PEEK), polycarbonate, polyolefin's, polyethylene's, polyether block amides (PEBAX), nylon 6, 6-6, 12, Polypropylene, polyesters, polyurethanes, polytetrafluoroethylene (PTFE) Poly(phenylene sulfide) (PPS), poly(butylene terephthalate) PBT, polysulfone, polyamide, polyimide, poly(pphenylene oxide) PPO, acrylonitrile butadiene styrene (ABS), Polystyrene, Poly(methyl methacrylate) (PMMA), Polyoxymethylene (POM), Ethylene vinyl acetate, Styrene acrylonitrile resin, Polybutylene. The stent may also be comprised of the following absorbable polymeres: Poly (PGA), Polylactide (PLA), Poly(-caprolactone), Poly(dioxanone) Poly(lactide-coglycolide). Stent 137 stent according to various embodiments is laser cut from a round tubing or from a flat sheet of metal. The flat representation of the stent circumference is shown in item 138. The flat representation of an expanded stent is shown in item 139. The end view of the stent is shown 141. Magnets 140 are attached to the stent on the outside diameter. The magnets may be attached to the stent by use of a mechanical fastener, glue, suture, welding, snap fit or other suitable means. The stent can be either balloon expandable or self expanding. The magnets may be located in middle of the stent or at the ends of the stent. Suitable materials for the magnets include: neodymium-iron-boron [Nd—Fe—B], samarium-cobalt [Sm—Co], alnico, and hard ferrite [ceramic] or other suitable material. In some embodiments, the magnets are encapsulated in another metal (e.g., titanium) or polymer to improve corrosion resistance and biocompatibility.

Figure 6B:
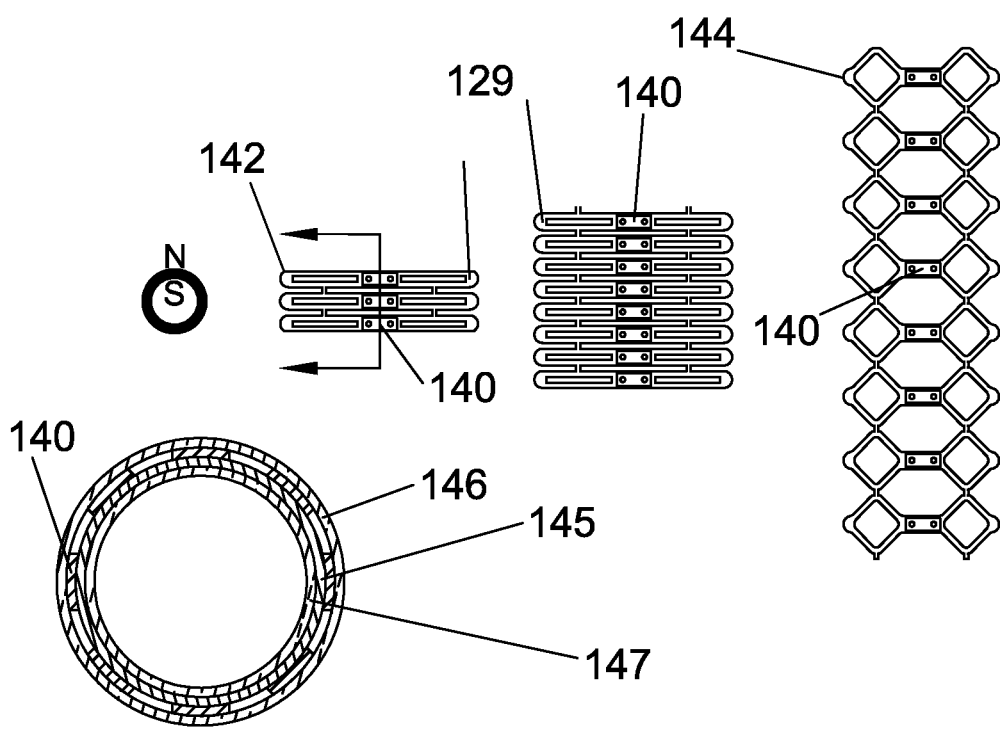
FIG. 6B is a drawing of a stent that can used as a docking element that has a polymer covering on the inside and outside.

FIG. 6B shows various views of a stent that can used as a docking or anchoring element. Stent 142 may be laser cut from a round tubing or from a flat sheet of metal. The flat representation of the stent circumference is shown in item 143. The flat representation of an expanded stent is shown in item 144. The end view of the stent is shown 145. Permanent magnets 140 are attached to the stent on the outside diameter. This stent is a covered stent. The stent covering is not shown on items 142, 143 or 144. The covering are shown on the end view which shows stent 145. Stent may have an outside covering 146, inside covering 147 or both. Suitable materials for the covering include but are not limited to: silicone, polyether block amides (PEBAX), polyurethanes, silicone polyurethane copolymers, nylon 12, polyethylene terphalate (PET), Goretex ePTFE, Kevlar, Spectra, Dyneena, polyvinyl chloride (PVC), polyethylene or polyester elastomers. The coverings may be dip coated onto the stent or they may be made as a separate tube and then attached to the stent by adhesives or mechanical fasteners such as suture, rivets or by thermal bonding of the material to the stent or another layer. The covering may also have drugs incorporated into the polymer to provide for a therapeutic benefit. The covering 146 or 147 may also be of biologic origin. Suitable biologic materials include but are not limited to: Amnion, Collagen Type I, II, III, IV, V, VI—Bovine, porcine, ovine, placental tissue or placental veins or arteries and small intestinal sub-mucosa.

Figure 7:
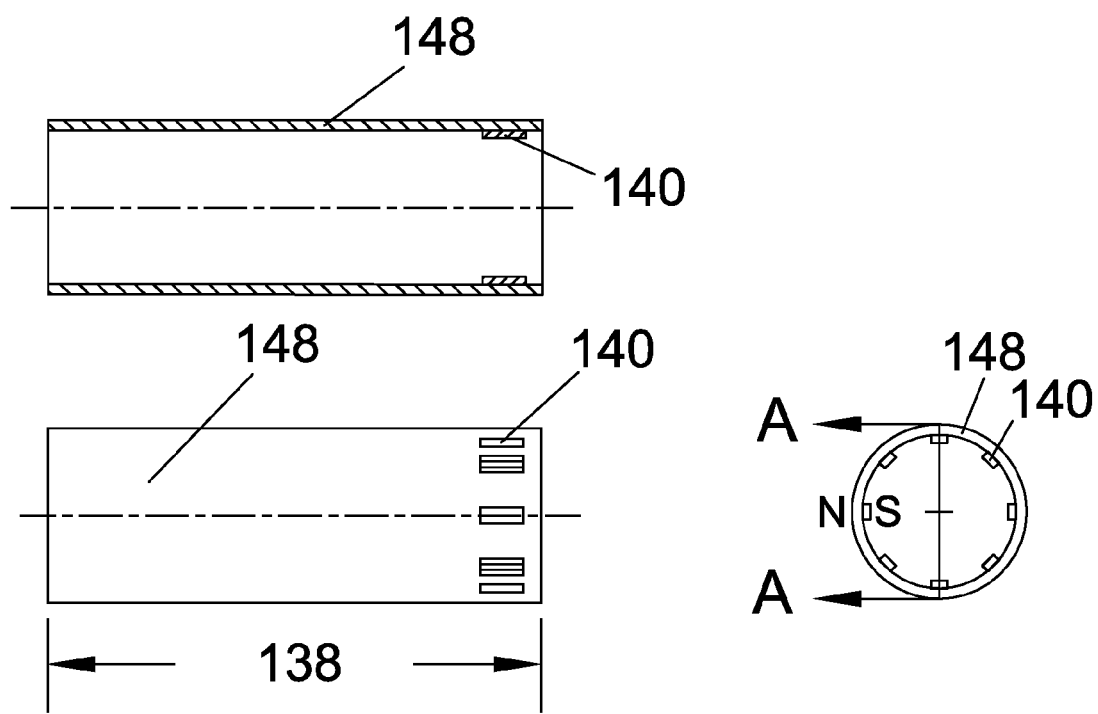
FIG. 7 is a tubular implant that can be used to bypass the stomach, duodenum or other intestinal lumen.

FIG. 7 is a tubular therapy implant that can be used to bypass the stomach 103, duodenum 112 or other intestinal lumens (e.g., a portion or all of the jejunum). The tubular implant is made of a thin wall tube 148 and a series of magnets 140 attached to the inside of the thin wall tube. According to other embodiments, the magnets 140 may be attached to the outside of the tube 148. According to various embodiments, the magnets 140 are disposed about a circumference of the tube 148 such that the location of the magnets correspond to locations of corresponding magnets located on the anchoring or docking element. The tubular implants of this invention may be comprised, for example, of the following materials: silicone, polyether block amides (PEBAX), polyurethanes, silicone polyurethane copolymers, Nylon, polyethylene terphalate (PET), Goretex ePTFE, Kevlar, Spectra, Dyneena, polyvinyl chloride (PVC), polyethylene, polyester elastomers or other suitable materials. The thin wall tube length 149 may range from 1 inch in length up to 5 feet in length. The thickness of the thin walled tube will typically be in the range of 0.0001 inches to 0.10 inches. The diameter of the tubular implant will range from typically 25 to 35 mm, but may also range anywhere from 5 mm to 70 mm in diameter.

Exemplary tubular elements for performing intra-luminal gastrointestinal therapies, e.g., treating metabolic disorders, which may be used with the system of present invention include, for example, those elements disclosed in any of U.S. Pat. Nos. 4,134,405; 4,314,405; 4,315,509; 4,641,653; 4,763,653; and 5,306,300, each of which is hereby incorporated by reference in its entirety.

Figure 8:
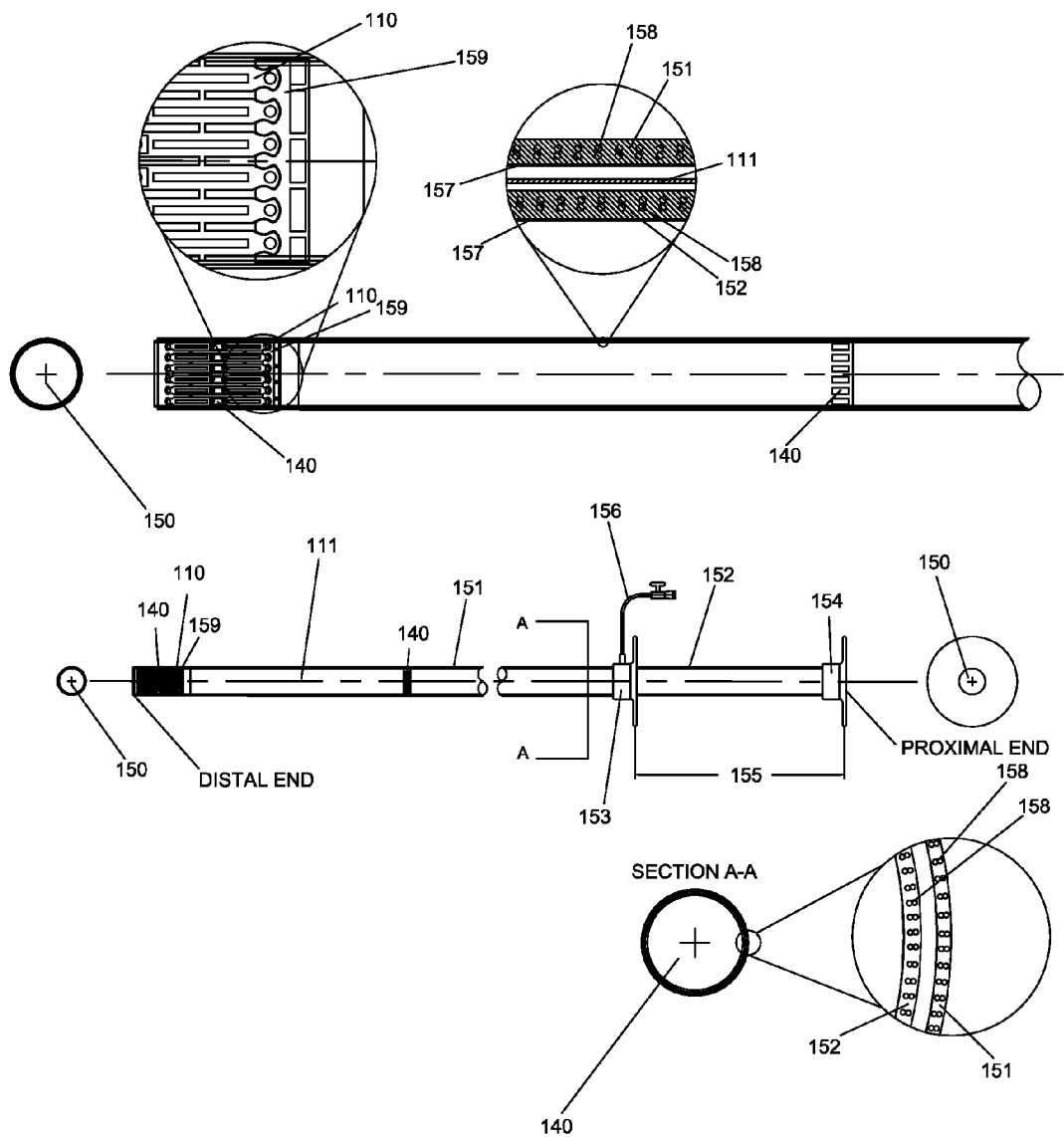
FIG. 8 is a drawing of a delivery catheter for the docking element and tubular implant.

FIG. 8 is a schematic view of a delivery catheter for a delivering a self expanding docking or anchoring element 110 and tubular or therapy implant 111, according to various embodiments of the invention. The delivery catheter is constructed with a central lumen 150 sufficiently large to allow the catheter to loaded be over the outside diameter of the endoscope 114. The delivery catheter consists of an outer catheter 151 and an inner catheter 152. To load the tubular implant onto the delivery catheter, the outer sheath handle 153 is retracted towards the inner catheter handle 154 until distance 155 (between the outer handle 153 and inner handle 154) is relatively small. The tubular implant 111 is then compressed around the inner catheter, and the outer sheath is partially closed by advancing the outer sheath handle 153 away from the inner sheath handle 154. When the tubular implant is completely (or sufficiently) covered by the outer sheath or catheter 151, the loading process is complete for the tubular implant. The delivery catheter also has a space on the inner catheter 151 for the docking or anchoring implant 110 to be loaded. As shown in FIG. 8, the anchoring implant 110 is compressed around the distal portion of the inner catheter 152. The outer sheath handle 153 is then advanced distally until it completely (or sufficiently) covers and retains the anchoring implant. In one embodiment, the tubular or therapy implant 111 is compressed over the inner catheter and the outer catheter is placed over the outside (left to right in FIG. 8) of the tubular implant 111.

As further shown in FIG. 8, according to exemplary embodiments, a stent retainer 159 is attached to the inner catheter. The stent retainer 159 acts to prevent the stent (e.g., the anchoring or docking implant 110) from releasing from the delivery catheter prematurely during deployment. The stent retainer is fastened to the inner catheter. The stent retainer 159 can be made from metal or plastic and can be made radiopaque by making from it from a radiopaque material such as tantalum. The stent retainer has a complementary shape that holds the tips on the stent and does not allow the stent to move distally or forward until the outer sheath 151 is fully retracted to the stent retainer 159.

The catheter has a side port 156 which allows the space between the inner and outer sheaths to be flushed with saline. The outer sheath 151 and inner sheath 152 may be made from made from a simple single layer polymer extrusion such as from polyethylene or PTFE. The outer sheath may also be constructed in the following manner. The sheath inner diameter surface is constructed of a thin wall PTFE liner 157. A layer of reinforcement 158 is placed over the PTFE liner, the reinforcement is preferably either a braid of wire or a coil of wire. The wire cross section can be either round or rectangular. The preferred material for the wire is a metal such as 316 or 304 stainless steel or Nitinol or other suitable material. The wire diameters are typically in the 0.0005 inch to 0.010 inch diameter range. The outer jacket material is preferably reflowed into the reinforcement layer by melting the material and flowing it into the spaces in between the braided wire or the coil wires.

Figure 9A:
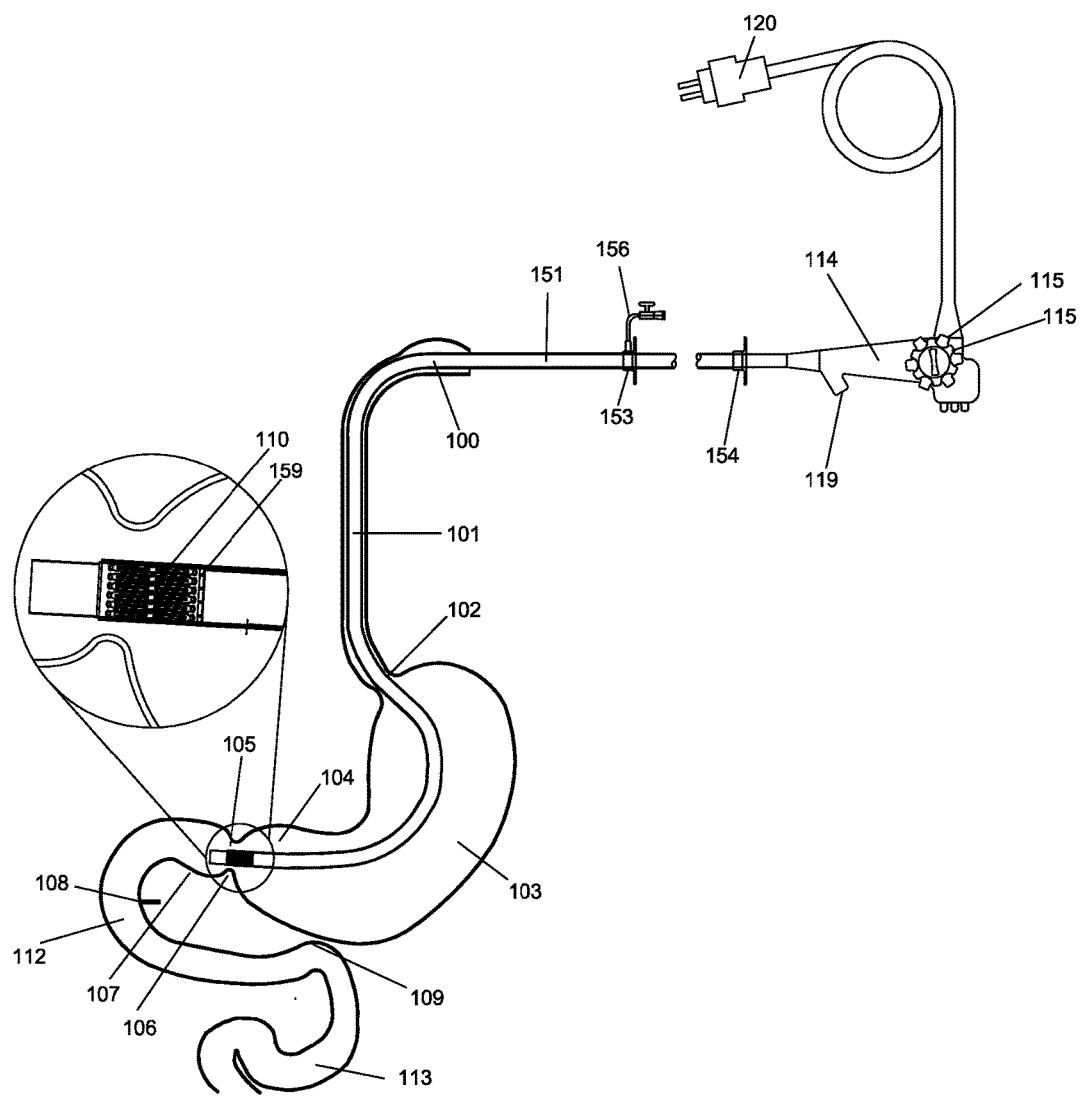
FIG. 9A is a cross sectional view of a portion of the digestive tract in the body. A delivery catheter with a docking element and tubular implant loaded onto the catheter are loaded onto an endoscope. The endoscope is then advanced through the esophagus, stomach and into the duodenal bulb.
Figure 9B:
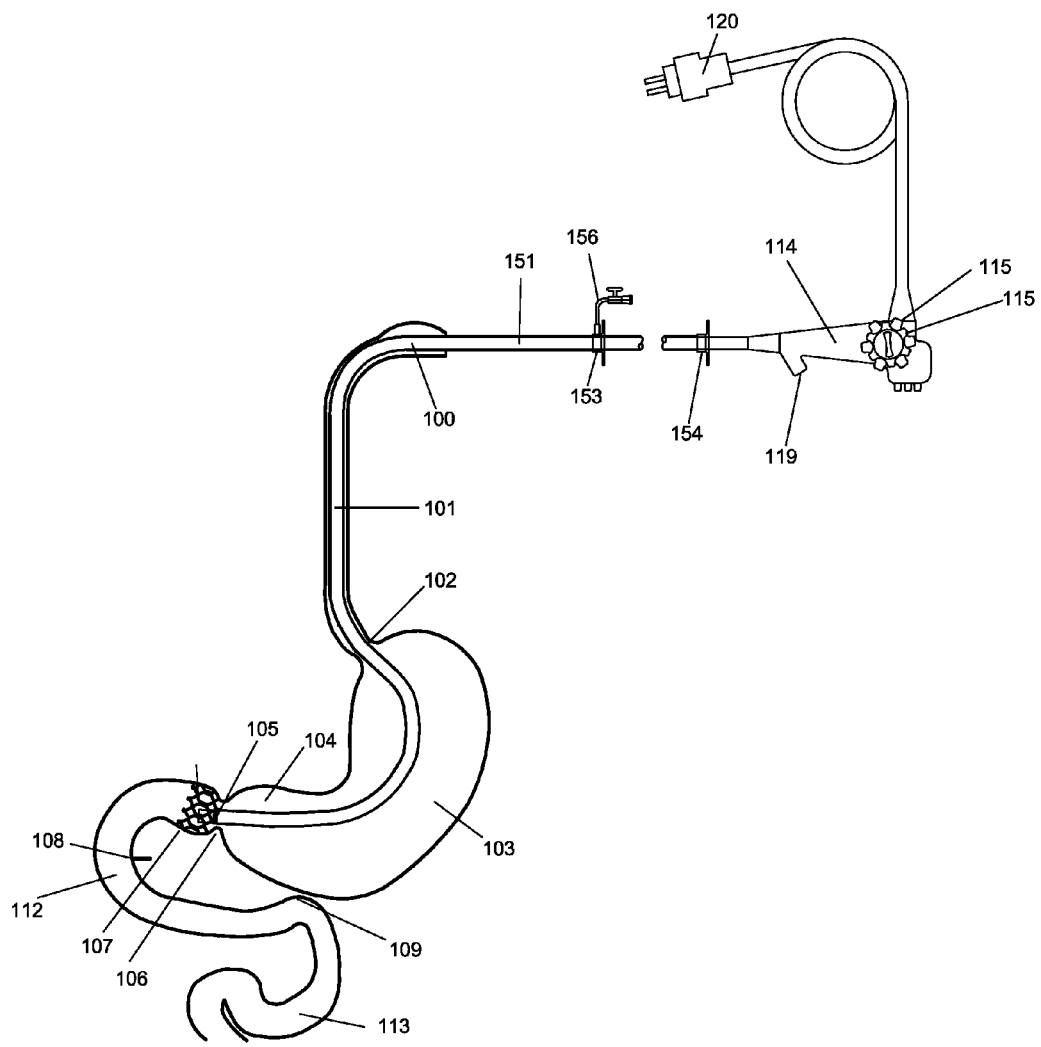
FIG. 9B is a cross sectional view of a portion of the digestive tract in the body. A delivery catheter with a docking element and tubular implant loaded onto are loaded onto an endoscope. The endoscope is then advanced through the esophagus, stomach and into the duodenal bulb. The outer sheath of the delivery catheter is refracted to partially deploy the docking element into the duodenal bulb.
Figure 10:
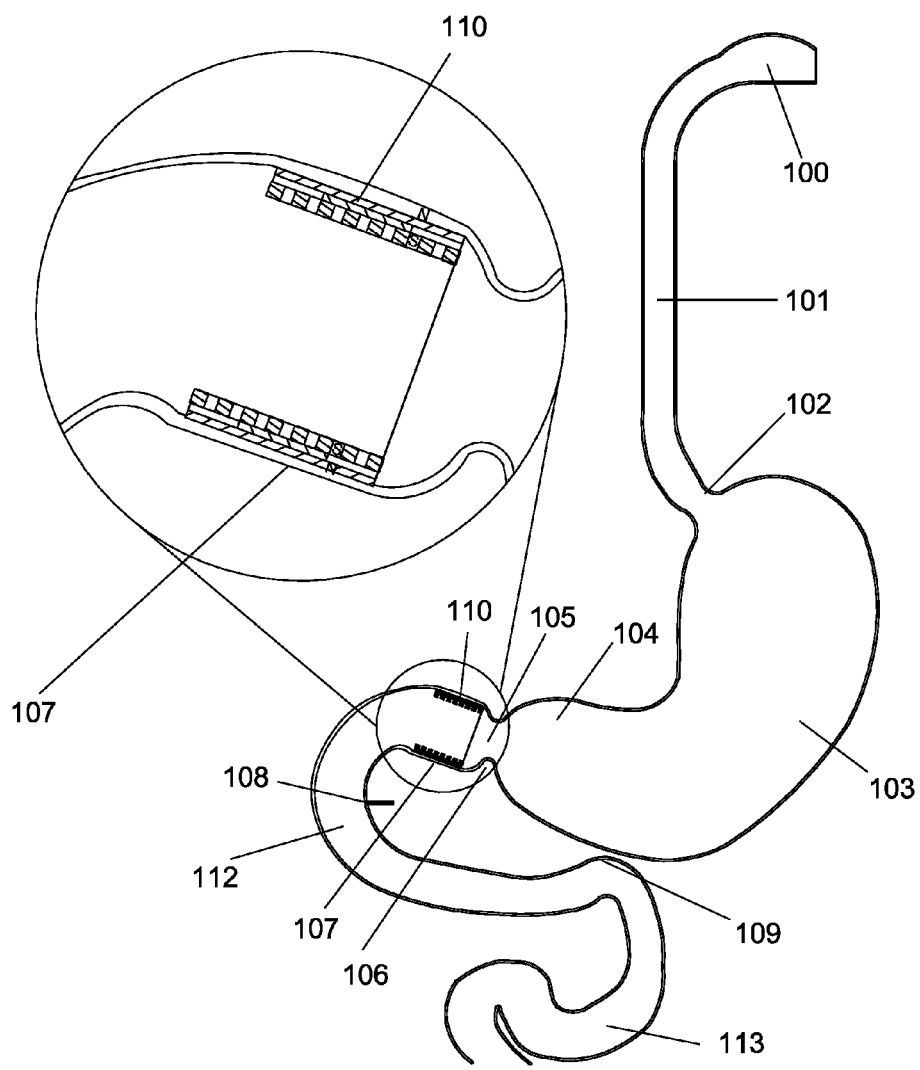
FIG. 10 is a drawing showing the docking element fully deployed into the duodenal bulb. The delivery catheter and endoscope has been has been removed to show clarity

FIGS. 9A-16 shows a series of steps in the implantation of the apparatus herein disclosed, according to an exemplary embodiment. FIG. 9A is a schematic view of a portion of the digestive tract in the body. A delivery catheter with a docking element 110 and tubular implant 111 loaded onto the catheter are loaded over the outside of an endoscope. The endoscope is then advanced through the esophagus, stomach, such that a distal portion is located in the pylorus or the duodenal bulb. FIG. 9B is a schematic view of a portion of the digestive tract in the body. As shown, a delivery catheter with a docking element 110 and tubular implant 111 loaded onto the catheter are loaded onto an endoscope. The endoscope is then advanced through the esophagus, stomach and into the duodenal bulb. The outer sheath or catheter 151 is then retracted by moving outer handle 153 towards inner handle 154 to deploy the docking or anchoring element 110. FIG. 10 is a schematic view of a portion of the digestive tract in the body. The drawing shows the docking element 110 fully deployed into the duodenal bulb 107. The delivery catheter and endoscope have been has been removed to show clarity.

Figure 11:
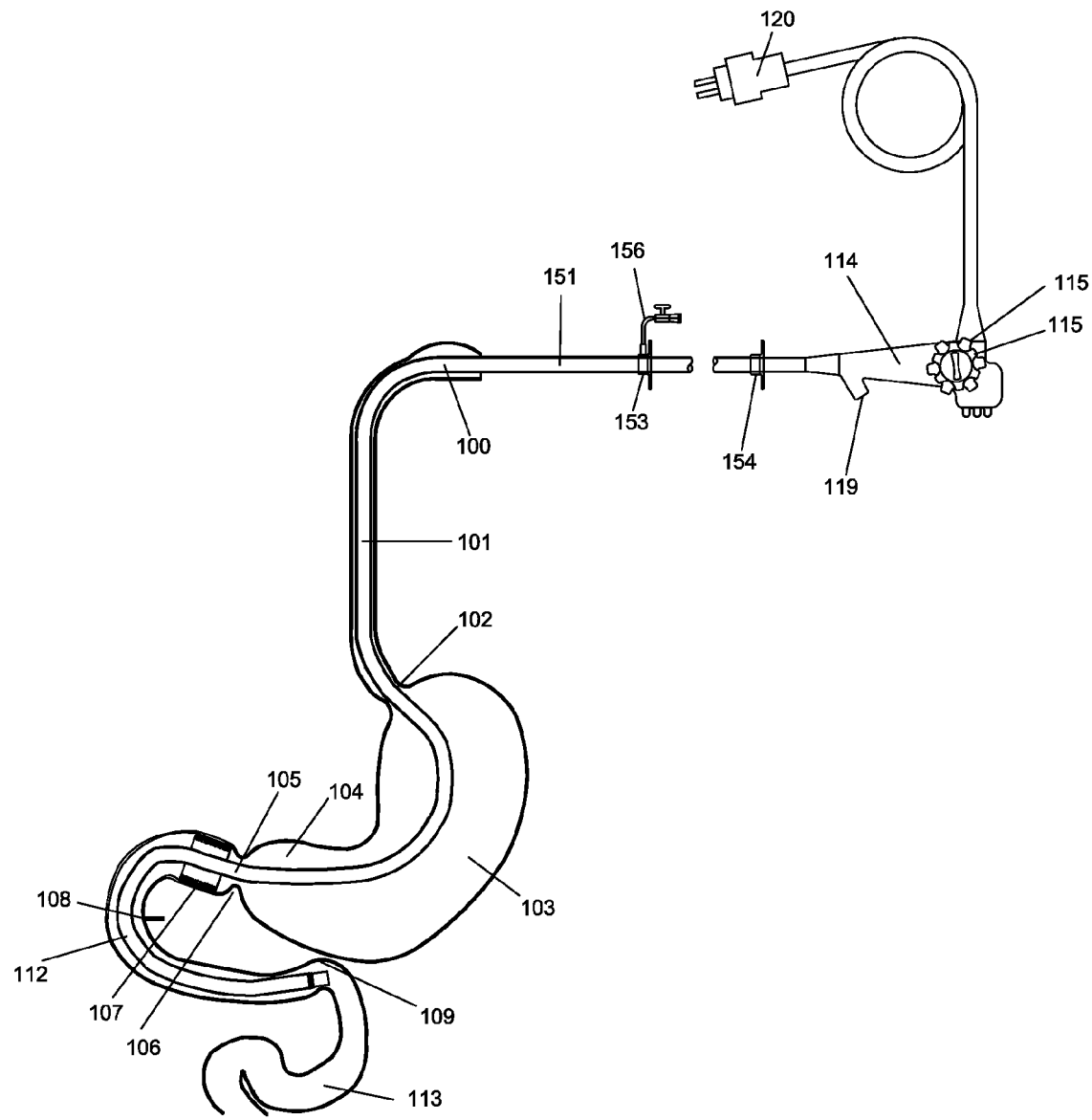
FIG. 11 is a drawing showing the endoscope and delivery catheter advanced through the docking element into the duodenum up to the ligament of treitz.
Figure 12:
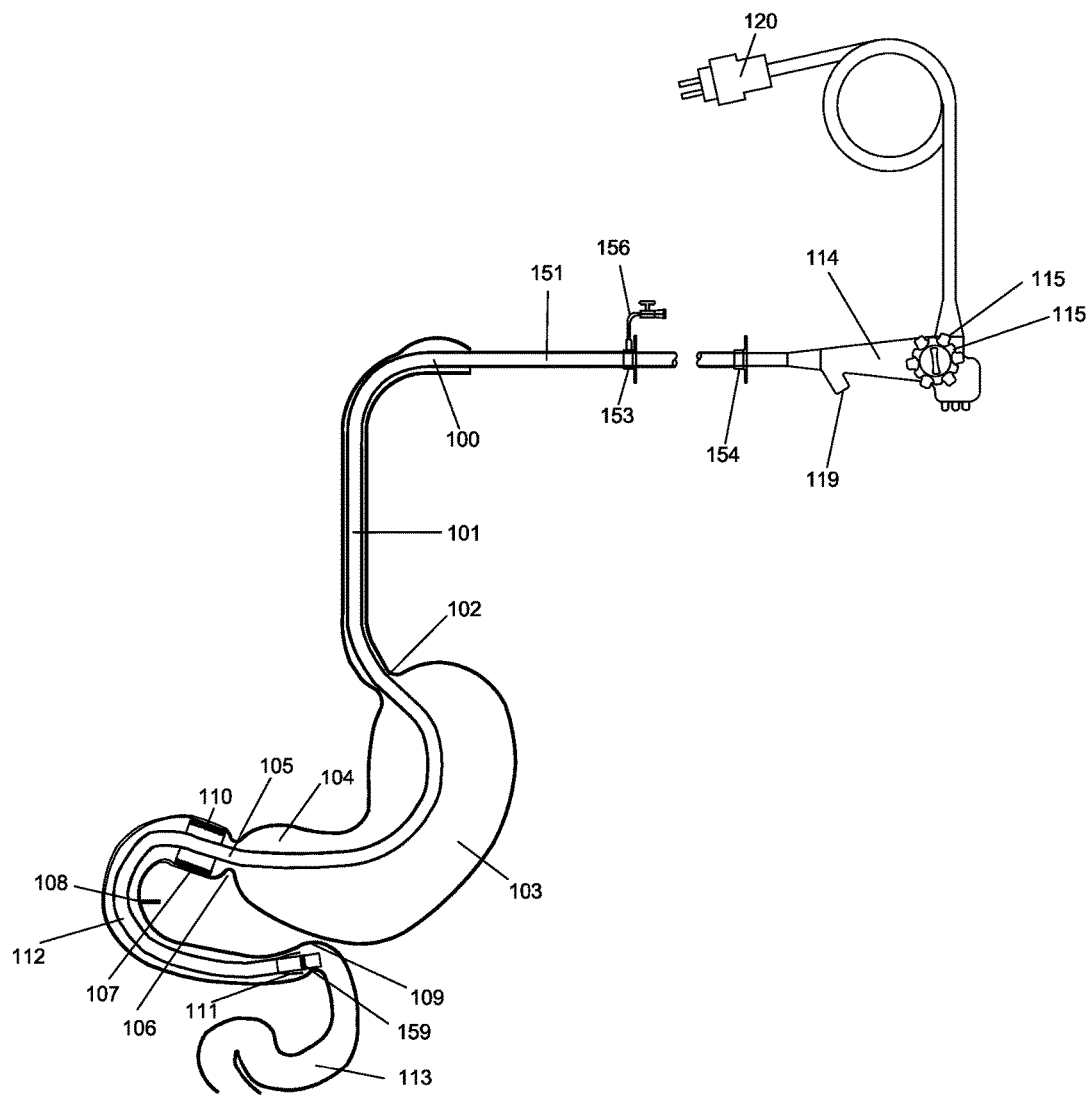
FIG. 12 is a drawing showing the endoscope and delivery catheter advanced through the docking element into the duodenum up to the ligament of treitz. The outer sheath of the delivery catheter is retracted to partially expose the tubular implant.

FIG. 11 is a schematic view showing the delivery catheter (of FIG. 9), wherein the docking element is fully deployed, further advanced into the duodenum 112 until the distal end of the delivery catheter is disposed at or near the ligament of treitz 109. Next, as shown in FIG. 12, the outer sheath 151 of the delivery catheter is refracted slightly (e.g., 1-3 centimeters) to expose the distal portion of the tubular implant 111. Also, the tubular implant 111 is advanced forward slightly (e.g., 1-5 centimeters), such that a sufficient amount of the distal end of the tubular implant 111 is disposed beyond the distal most portion of both the inner sheath 152 and the outer sheath 151. In some embodiments, this is accomplished by use of a third intermediate sleeve to apply a distal force to the tubular implant 111. In other embodiments, after deploying the anchoring element, the physician removes the endoscope from the patient, loads the tubular implant with a sufficient amount extending distally, then advances the endoscope to the appropriate locations and deploys the tubular implant 111.

Figure 13:
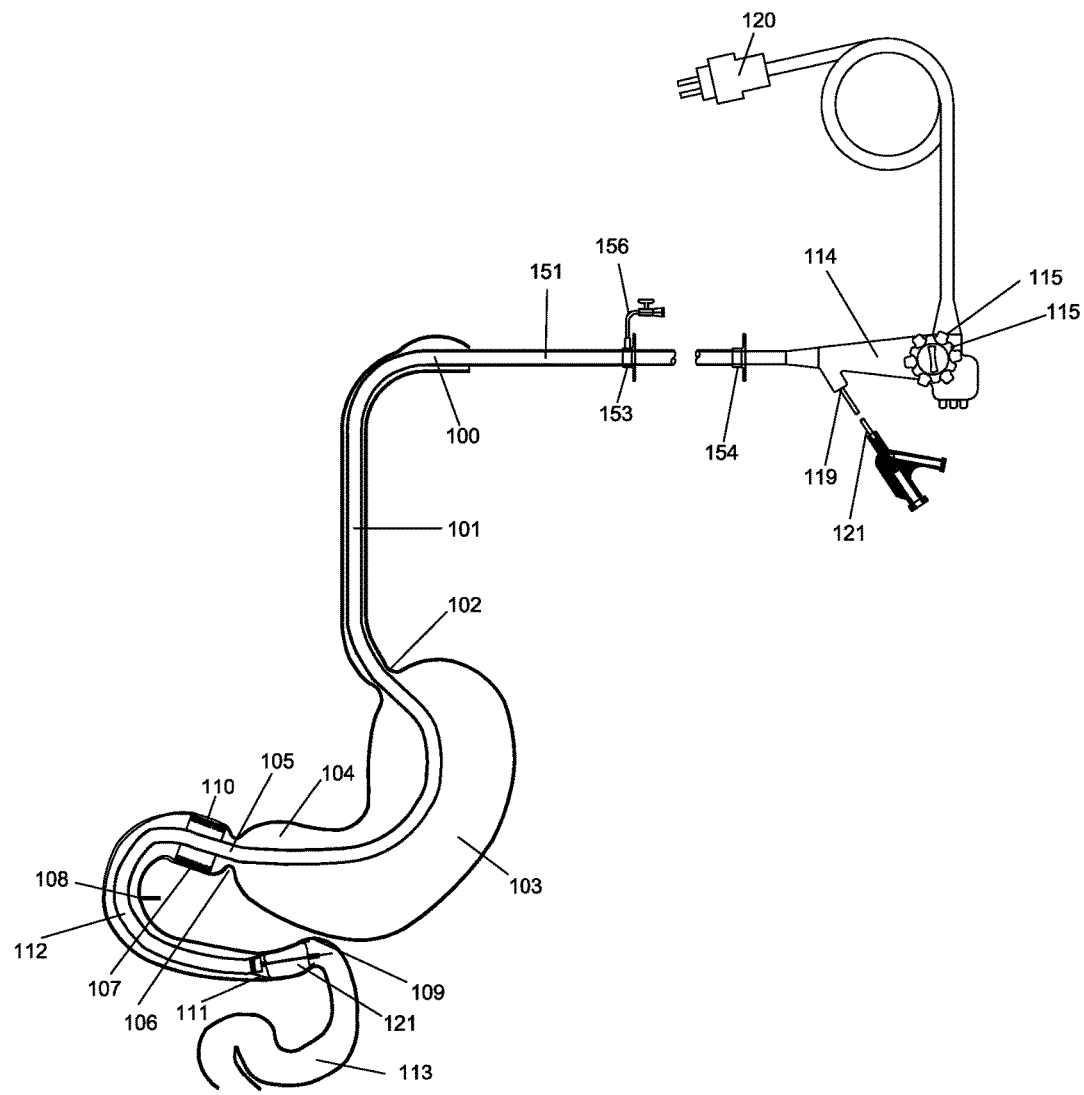
FIG. 13 is a drawing showing the endoscope and delivery catheter advanced through the docking element into the duodenum up to the ligament of treitz. The outer sheath of the delivery catheter is retracted to partially expose the tubular implant. A balloon catheter is inserted through the working channel of the endoscope to the area of the partially exposed tubular implant. The balloon is inflated to temporarily secure the tubular implant to the duodenum.

Then, in FIG. 13, a sizing balloon 121 has been inserted through the working channel 119 on endoscope 114. The sizing balloon 121 is advanced slightly (e.g., 1-2 inches) beyond the distal end of the endoscope 114 but still inside of the tubular implant 111. The sizing balloon 121 is then inflated with saline or contrast agent to generate sufficient radial force to hold the tubular implant 111 in place in the duodenum 112 near the ligament of treitz 109.

Figure 14:
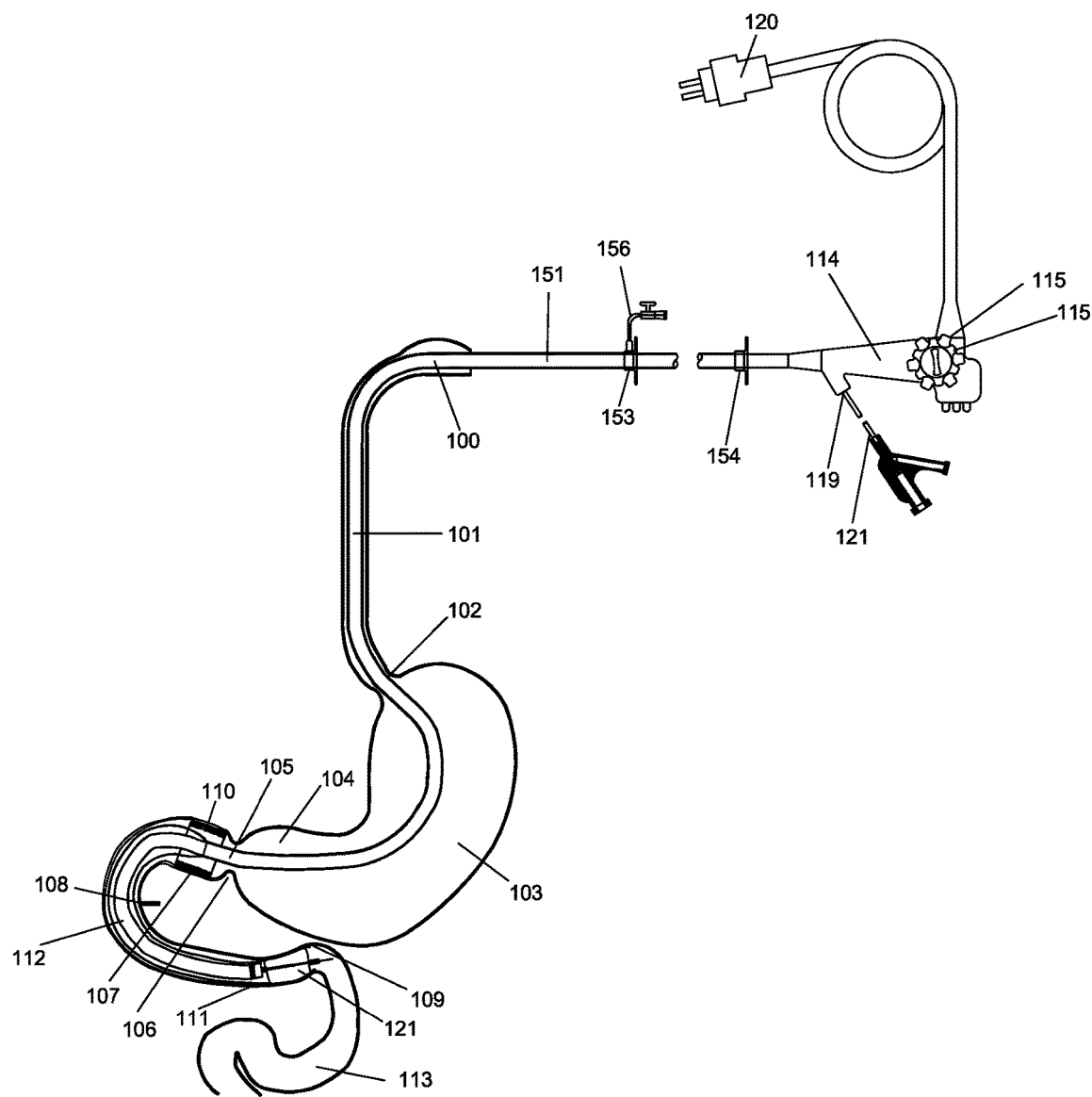
FIG. 14 is a continuation of FIG. 13 where the outer sheath is retracted further to unsheath the tubular implant up to the duodenal bulb.
Figure 15:
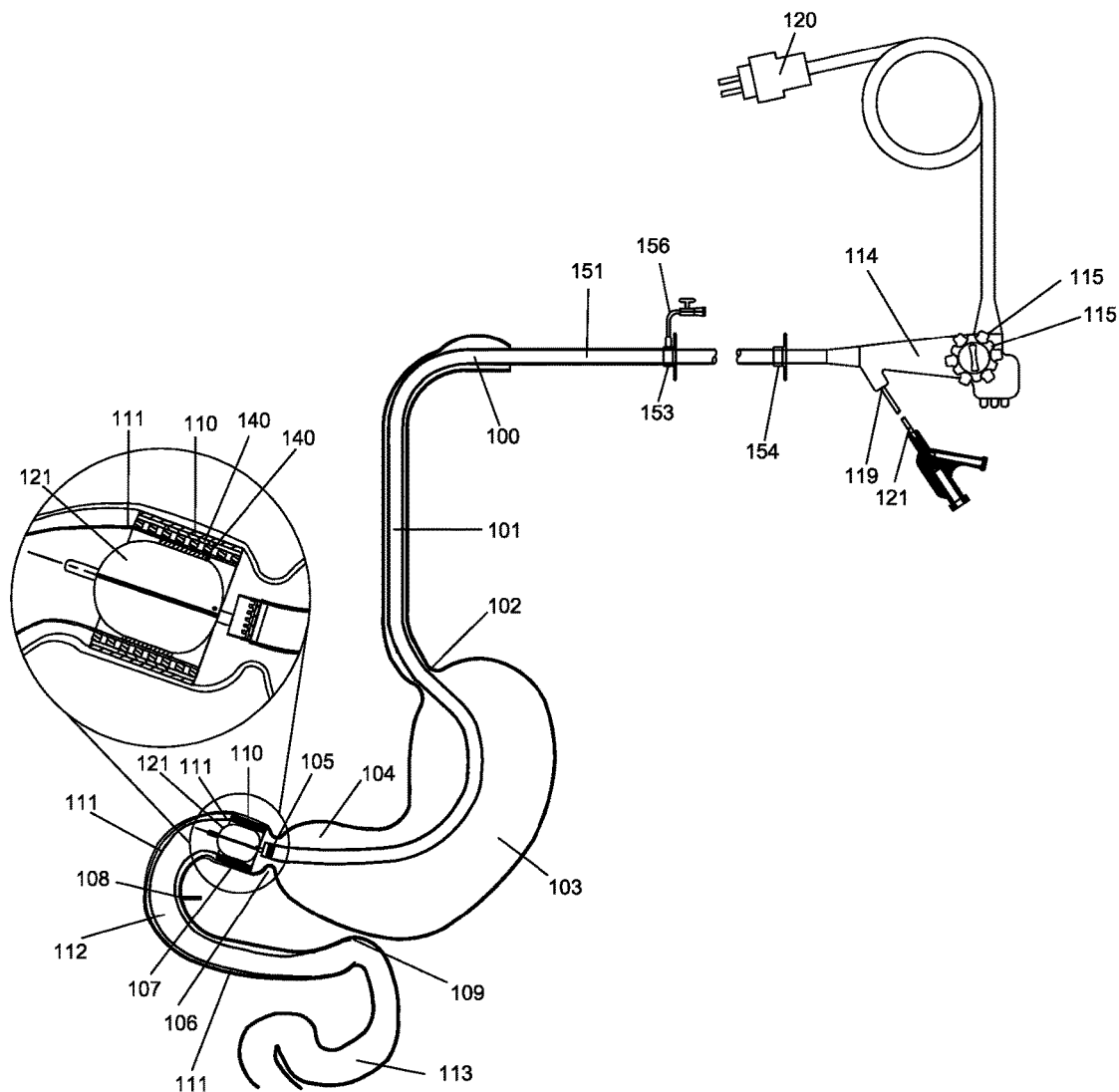
FIG. 15 is a continuation of FIG. 14 where the endoscope has been withdrawn to the duodenal bulb. The balloon on the balloon catheter is then deflated and the balloon catheter is withdrawn to the duodenal bulb. The balloon is then re-inflated to open up and secure the proximal end of the tubular implant to the inside diameter of the docking element.

Next, as shown in FIG. 14, the outer sheath 151 is retracted further to expose much or most (e.g., all but 1-3 centimeters) of the tubular implant 111. The outer sheath 151 end is now located at or near the pylorus 106. Then, a shown in FIG. 15, the distal end of the endoscope 114 has been pulled back to the pyloric orifice 105 and the sizing balloon 121 has been deflated and repositioned at a location near the proximal end of the tubular implant 111. The sizing balloon 121 is then reinflated to force or urge the proximal end of the tubular implant 111 into contact with the docking element 110, such that the magnets 140 on the tubular sleeve are now in contact with the magnets 140 on the docking element. The magnetic attraction between the magnets 140 secures the tubular implant 111 to the docking element 110. The endoscope 114 is then removed and the procedure is complete.

Figure 16:
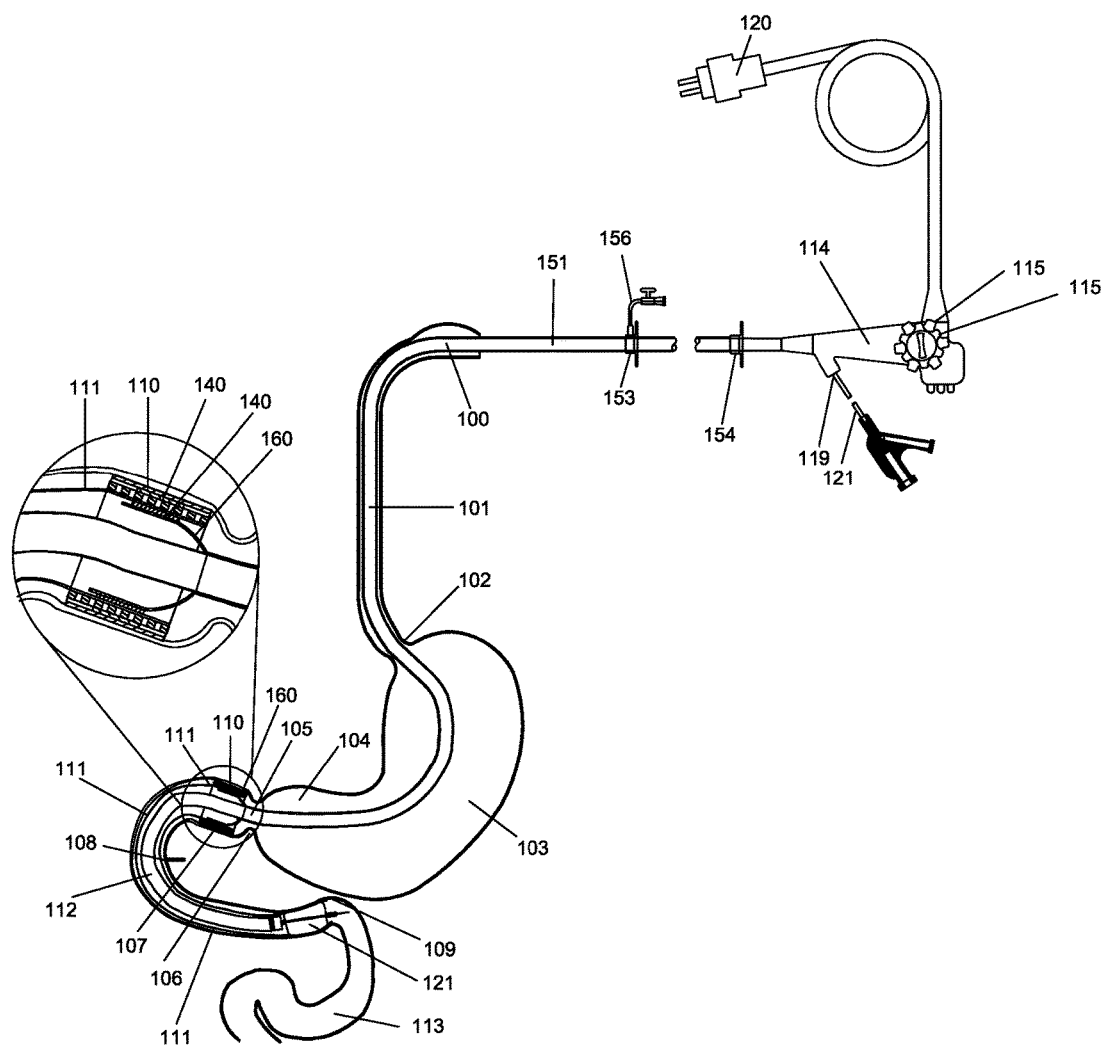
FIG. 16 is a drawing of an alternative device and method for deploying the proximal end of the tubular element.

FIG. 16 shows an alternative embodiment for securing the proximal end of the tubular implant 111 to the docking element 110. As shown, according to various embodiments, a Nitinol conical and tubular shaped forceps 160 are attached to the inner catheter near the proximal end of where the tubal implant is loaded on the delivery catheter. The Nitinol forceps 160 are configured to have an elastic memory in the open state. When the outer sheath 151 is full refracted the conical forceps open and in turn urge open the proximal end of the tubular implant 111 to seat the magnets on the tubular implant 111 to the magnets on the docking station 110.

At some point during or after implantation of the docking element 110 or the tubular implant 111, the physician may wish to remove one or both components. Either or both components may be readily removed using any of a number of techniques generally known in the art. One such technique for removing or extracting the stent or stent-like portion of the docking element 110 or the tubular implant 111 involves use of a retrieval hook and a collapsing sheath or overtube. One such exemplary system is disclosed in EP 1 832 250, which is hereby incorporated by reference in its entirety. Other removal or extraction systems are disclosed, for example in each of U.S. Publication 2005/0080480, U.S. Pat. No. 5,474,563, and U.S. Pat. No. 5,749,921, each of which is hereby incorporated by reference in its entirety.

Figures 17A, 17B:
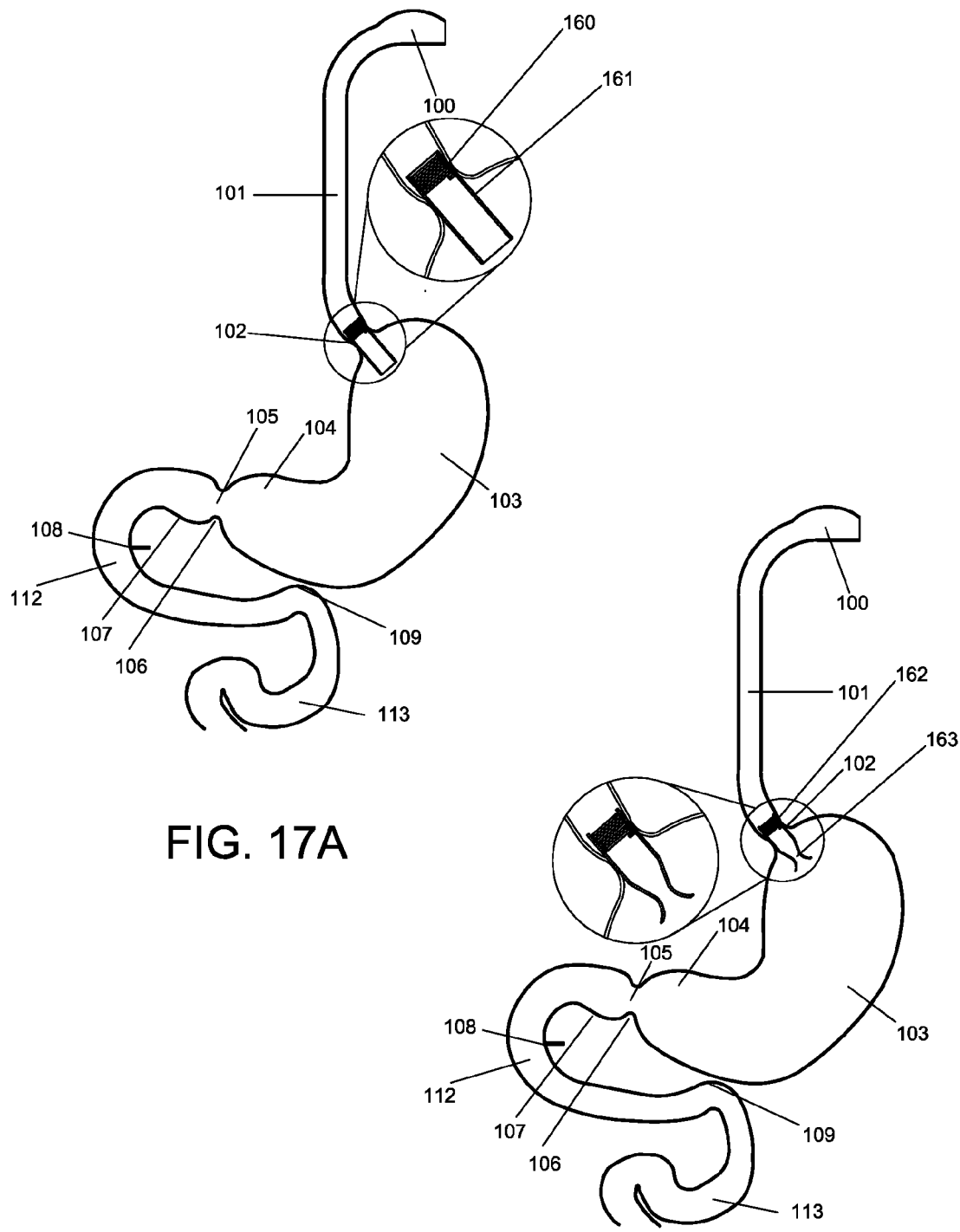
FIG. 17A is a cross sectional view of a portion of the digestive tract in the body. A docking element is implanted in the esophagus at the gastro-esophageal junction. The docking element serves as an anti-reflux valve.
FIG. 17B is a cross sectional view of a portion of the digestive tract in the body. A docking element is implanted in the esophagus at gastro-esophageal junction. The docking element serves as a restrictive stoma.
Figure 18:
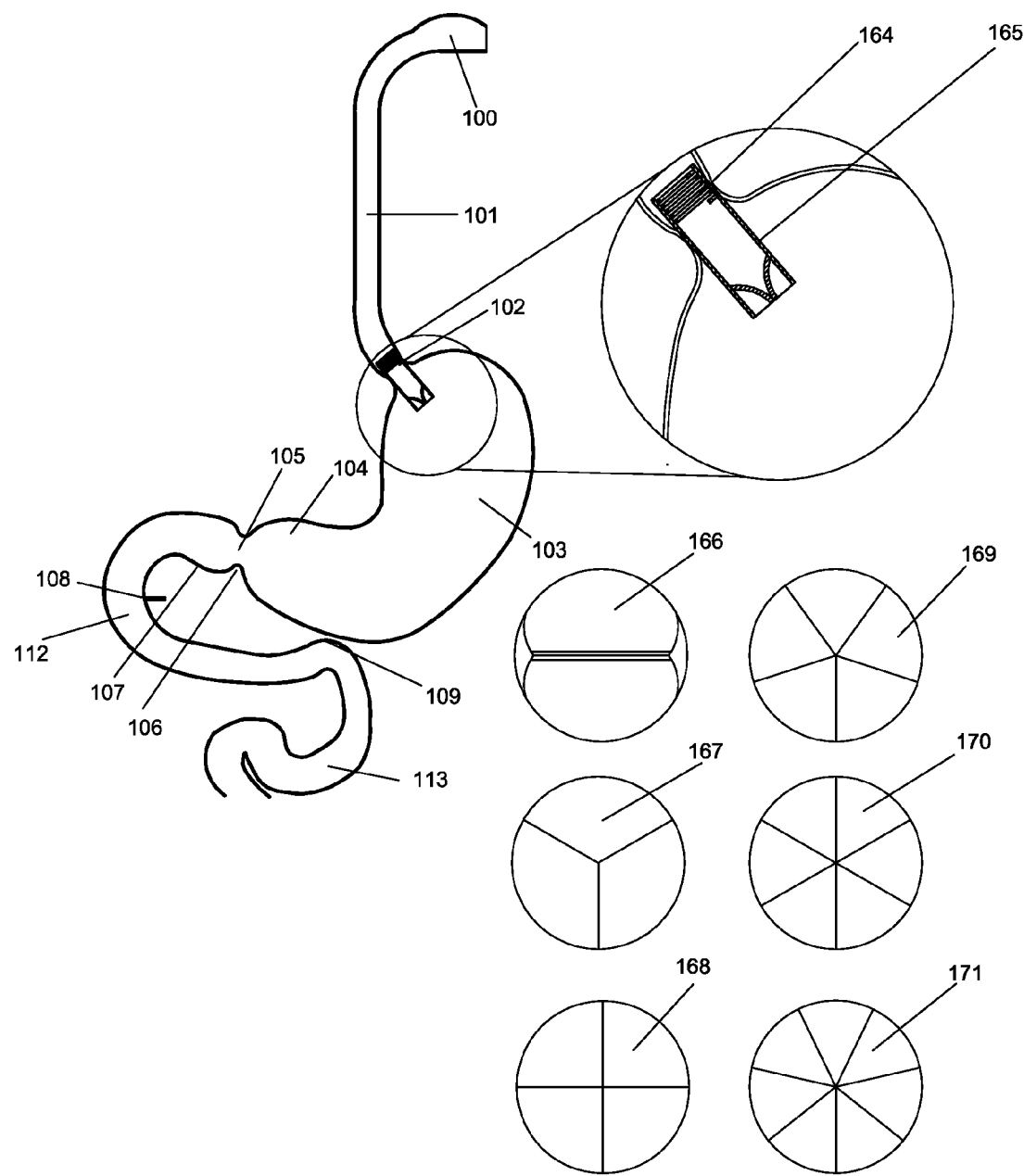
FIG. 18 is a cross sectional view of a portion of the digestive tract in the body. A docking element is implanted in the esophagus at gastro-esophageal junction. The docking element serves as an anti-reflux valve.

FIG. 17A is a schematic view of a portion of the digestive tract in the body. A docking element 160 is implanted in the esophagus at gastro-esophageal junction 102. The docking element serves as an anti-reflux valve when the tube 161 is compressed flat by pressure in the stomach 103. FIG. 17B is a schematic view of a portion of the digestive tract in the body. A docking element 162 is implanted in the esophagus at gastro-esophageal junction 102. The docking element 162 has a neck or narrow portion having an inside diameter less than the diameter of the native gastro-esophageal junction. Due to this reduced diameter, the docking element 162 serves as a restrictive stoma. FIG. 18 is a schematic view of a portion of the digestive tract in the body. A docking element 164 is implanted in the esophagus at gastro-esophageal junction 102. A tubular implant 165 is attached to the docking element 164. The tubular implant can have bi-leaflet reflux valve 166, a tri-leaflet reflux valve 167, a quad-leaflet reflux valve 168, a penta-leaflet reflux valve 169, a six-leaflet reflux valve 170 or seven-leaflet reflux valve.

Figure 19A:
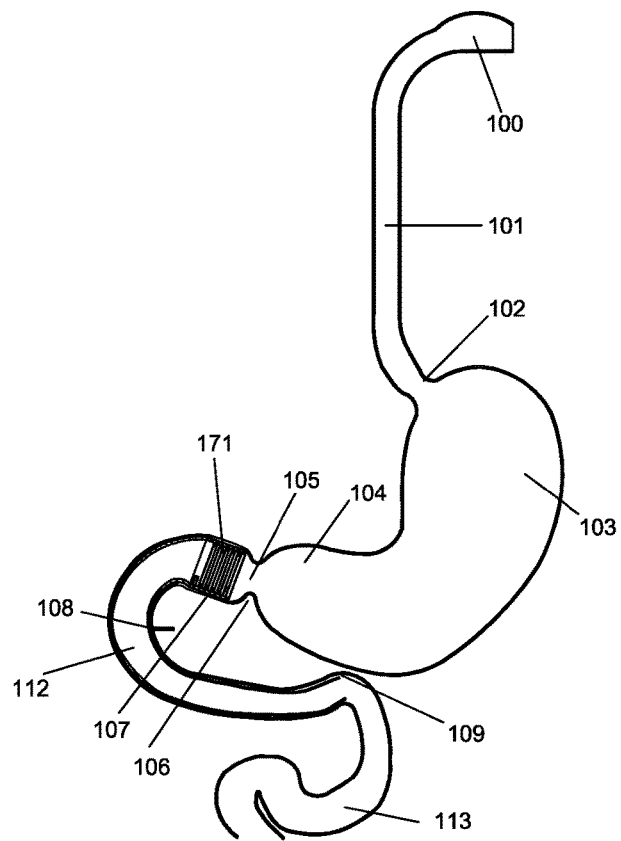
FIG. 19A is a stented sleeve with a stent used to hold open the sleeve. The sleeve located from the duodenal bulb to the ligament of treitz.

FIG. 19A is a schematic view showing an alternative embodiment of the invention, wherein a docking element is not used but a stented sleeve 171 is used. A stent is used to hold open the sleeve and anchor it. The sleeve extends from a proximal end in or near the duodenal bulb 107 to a distal end at or near the ligament of treitz 109. Those of skill in the art will understand that, in the stented-sleeve construct above, the stent and the sleeve could be mechanically pre-attached, such as by sutures or other chemical and mechanical bonding in which case the expansion of the stent results in anchoring of the stented sleeve structure on to the tissue. On the other hand, the stent could also reside freely within the sleeve at its end and when expanded could press the sleeve against the tissue to anchor it. All the stents and delivery catheters herein disclosed may also be used to deliver and anchor a stented sleeve or deliver a stent within a sleeve to anchor it on to surrounding tissue.

Figure 19B:
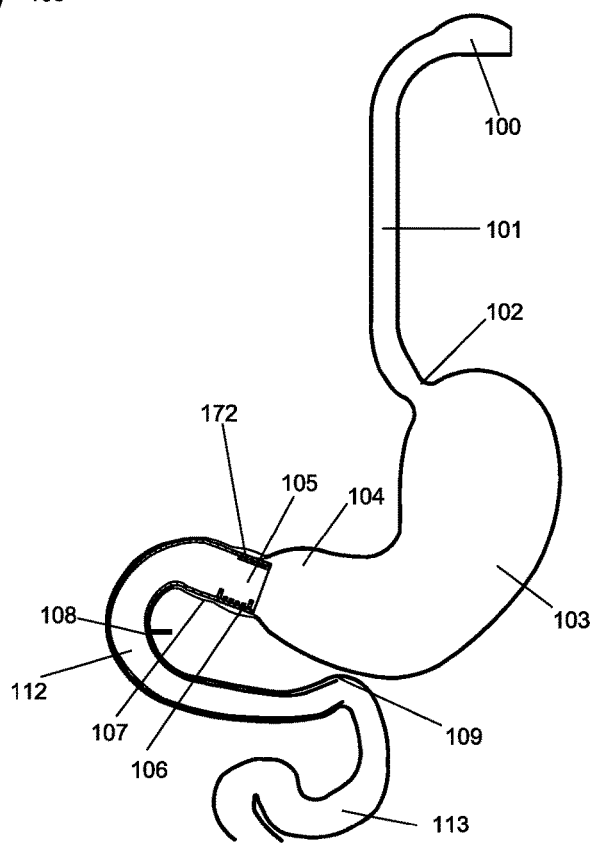
FIG. 19B is a stented sleeve with a stent used to hold open the sleeve. The sleeve located from the pylorus to the ligament of treitz.

FIG. 19B is an alternative embodiment of the invention wherein a docking element is not used but a stented sleeve 172 is used. A stent is used to hold open the sleeve and anchor it. As shown, in this embodiment, the sleeve extends from a proximal end at or near the pylorus 106 to a distal end at or near the ligament of treitz 109. Those of skill in the art will understand that in the stented-sleeve construct above the stent and the sleeve could be mechanically pre-attached, such as by sutures or other chemical and mechanical bonding in which case the expansion of the stent results in anchoring of the stented sleeve structure on to the tissue. On the other hand the stent could also reside freely within the sleeve at its end and when expanded could press the sleeve against the tissue to anchor it. All the stents and delivery catheters herein disclosed may also be used to deliver and anchor a stented sleeve or deliver a stent within a sleeve to anchor it on to surrounding tissue.

Figure 20:
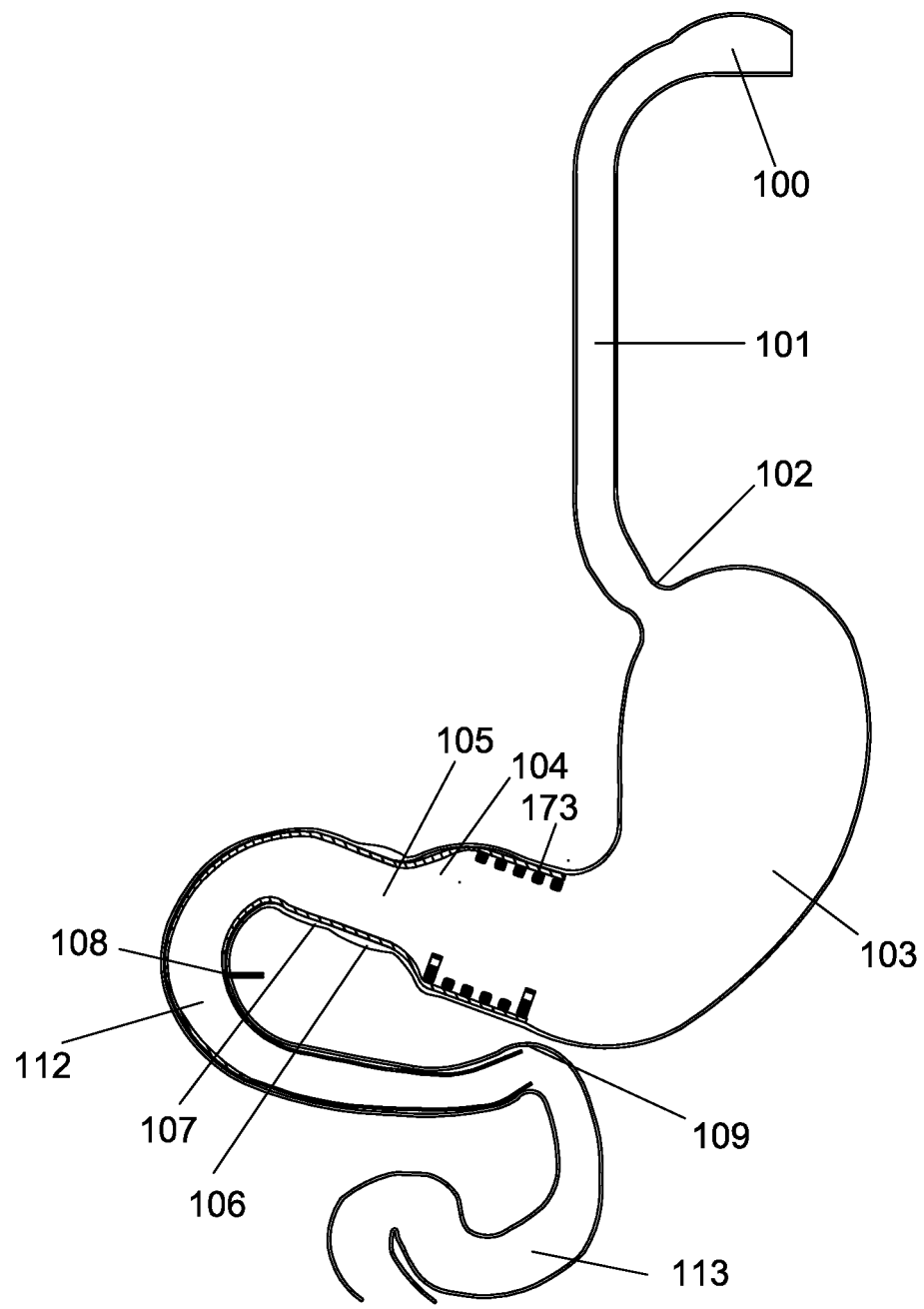
FIG. 20 is a stented sleeve with a stent used to hold open the sleeve. The sleeve is located from the stomach antrum to the ligament of treitz.

FIG. 20 is an alternative embodiment of the invention wherein a docking element is not used but a stented sleeve 173 is used. A stent is used to hold open the sleeve and anchor it. As shown, in this embodiment, the sleeve extends from a proximal end in the pyloric antrum 104 to a distal end at or near the ligament of treitz 109. Those of skill in the art will understand that in the stented-sleeve construct above the stent and the sleeve could be mechanically pre-attached, such as by sutures or other chemical and mechanical bonding in which case the expansion of the stent results in anchoring of the stented sleeve structure on to the tissue. On the other hand the stent could also reside freely within the sleeve at its end and when expanded could press the sleeve against the tissue to anchor it. All of the stents and delivery catheters herein disclosed may also be used to deliver and anchor a stented sleeve or deliver a stent within a sleeve to anchor it on to surrounding tissue.

Figures 21A, 21B:
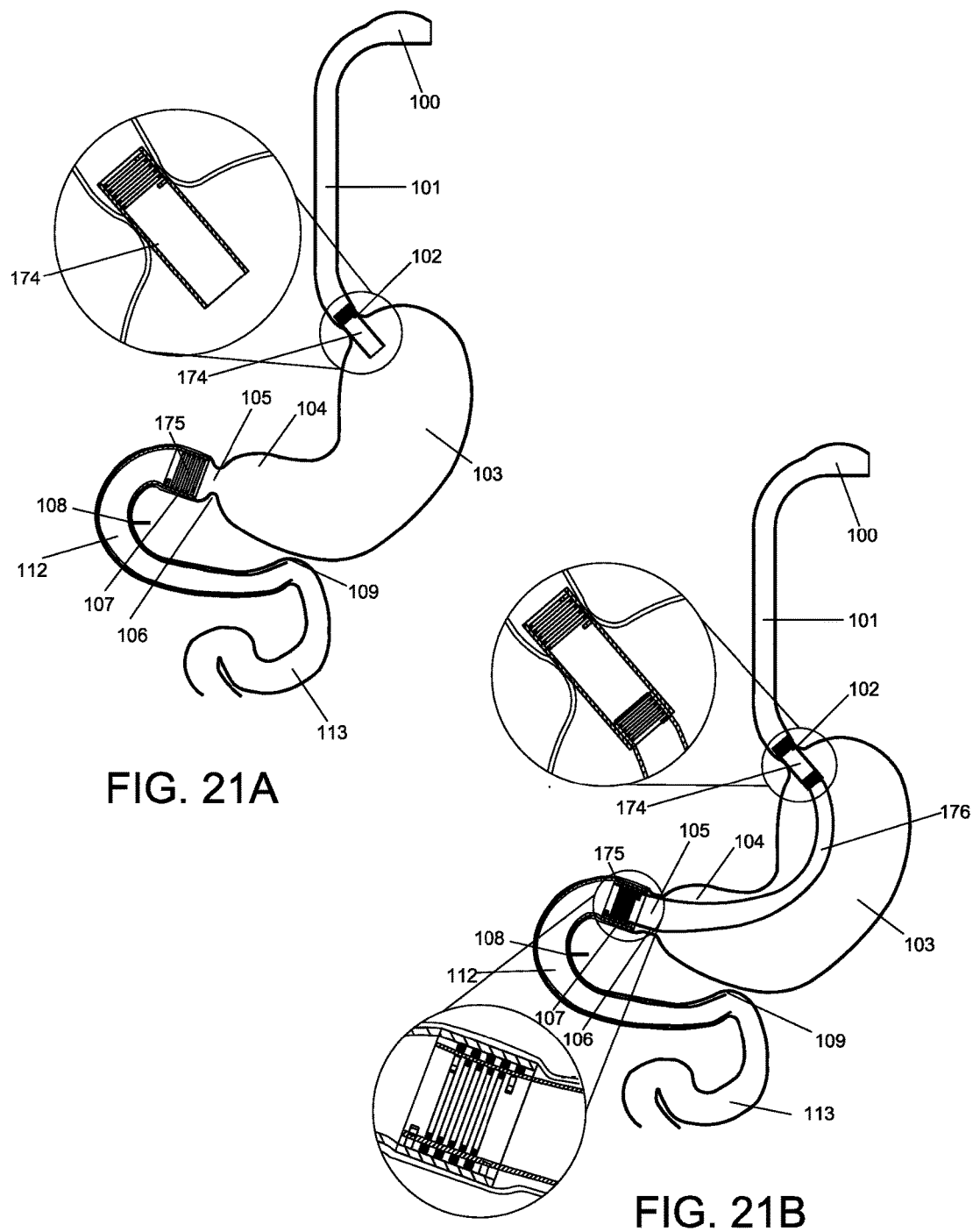
FIG. 21A is a sectional view of a portion of the digestive tract in the body. A docking element is implanted in the esophagus at the gastro-esophageal junction. A docking element and tubular implant is implanted in the duodenum also.
FIG. 21B is a sectional view of a portion of the digestive tract in the body. A docking element is implanted in the esophagus at the gastro-esophageal junction. A docking element and tubular sleeve is implanted in the duodenum also. A third implant element bypasses the stomach.

FIG. 21A shows an embodiment of the invention wherein a first docking (or anchoring) element 174 or a stented sleeve is implanted in the gastro-esophageal junction 102 and a second docking (or anchoring) element 175 or stented sleeve is implanted in the duodenal bulb 107. FIG. 21B shows an embodiment of the invention wherein a first docking element 174 or a stented sleeve is implanted in the gastro-esophageal junction 102, a second docking element 175 or stented sleeve in the duodenal bulb 107, and a third docking element and tubular implant 176 is implanted to bypass the stomach from 174 to 175.

FIG. 22A is an alternative embodiment of the invention wherein a first docking element 178 is implanted in the gastro-esophageal junction 102, a second docking element 177 and tubular implant is implanted extending from the docking element 178 to a distal end at or near the ligament of treitz. FIG. 22B is an alternative embodiment of the invention wherein a first docking element 178 is implanted in the gastro-esophageal junction 102, a second docking element 179 and tubular implant is implanted from the 178 docking element to the duodenal bulb 107.

Figure 23A:
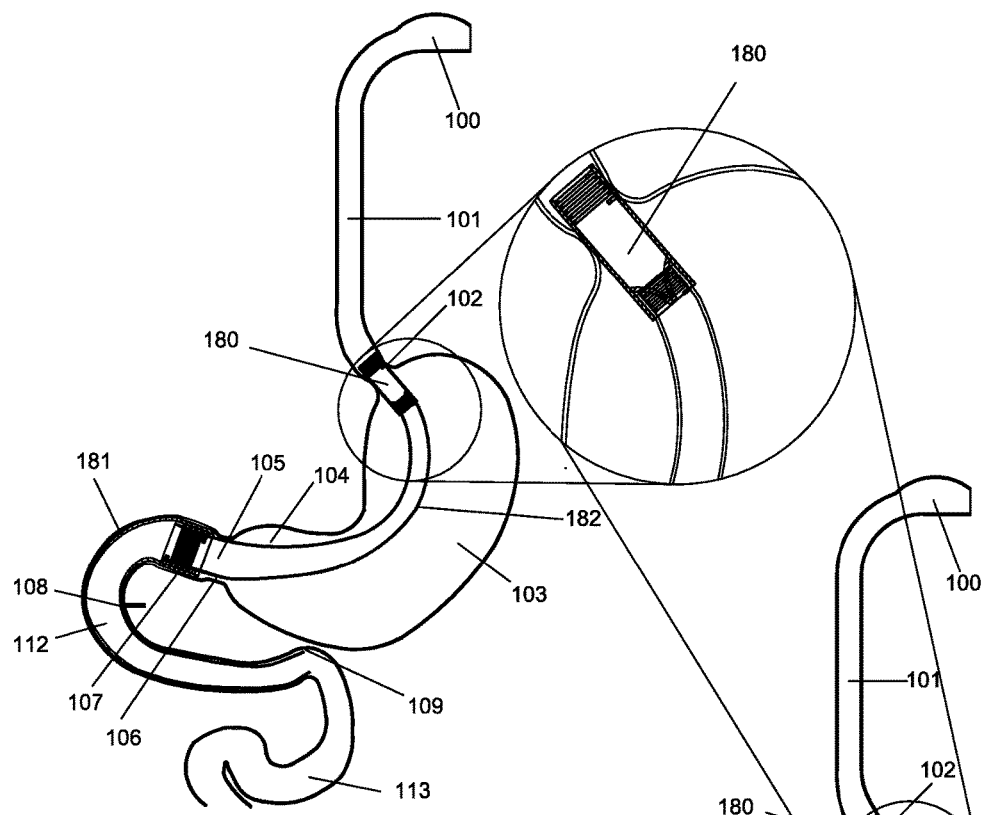
FIG. 23A is a sectional view of a portion of the digestive tract in the body. A docking element and tubular implant is implanted in the esophagus at the gastro-esophageal junction. The modular implant has an anti-reflux valve. A second docking station and tubular implant is placed in the duodenal bulb and extends to the ligament of treitz. A third docking station and tubular implant connects the esophageal implant and the duodenal implant.
Figure 23B:
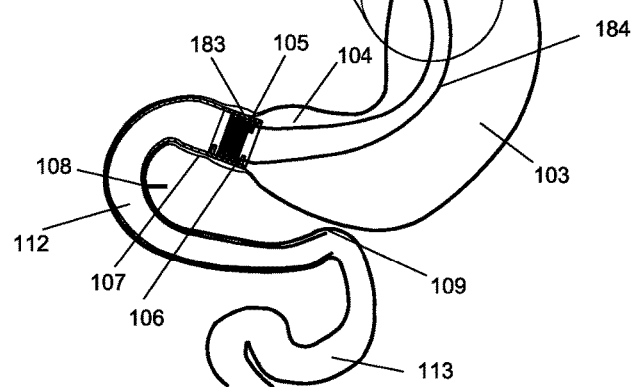
FIG. 23B is a sectional view of a portion of the digestive tract in the body. A docking element and tubular implant is implanted in the esophagus at the gastro-esophageal junction. The modular implant has an-anti reflux valve. A second docking station and tubular implant is placed in the pylorus and extends to the ligament of treitz. A third docking station and tubular implant connects the esophageal implant and the duodenal implant at the pylorus.

FIG. 23A is an alternative embodiment of the invention wherein a first docking element 180, having an anti-reflux valve, is implanted in the gastro-esophageal junction 102, a second docking element 181 and tubular implant is implanted from the duodenal bulb 107 to a location at or near the ligament of treitz. A third docking element 182 and tubular implant is implanted from the docking element 180 to the docking element 181. FIG. 23B is an alternative embodiment of the invention wherein a first docking element 180 with an anti-reflux valve is implanted in the gastro-esophageal junction 102, a second docking element 183 and tubular implant is implanted from a the pylorus 106 to the ligament of treitz. A third docking element 184 and tubular implant is implanted from the 183 docking to the 184 docking element.

Figure 24:
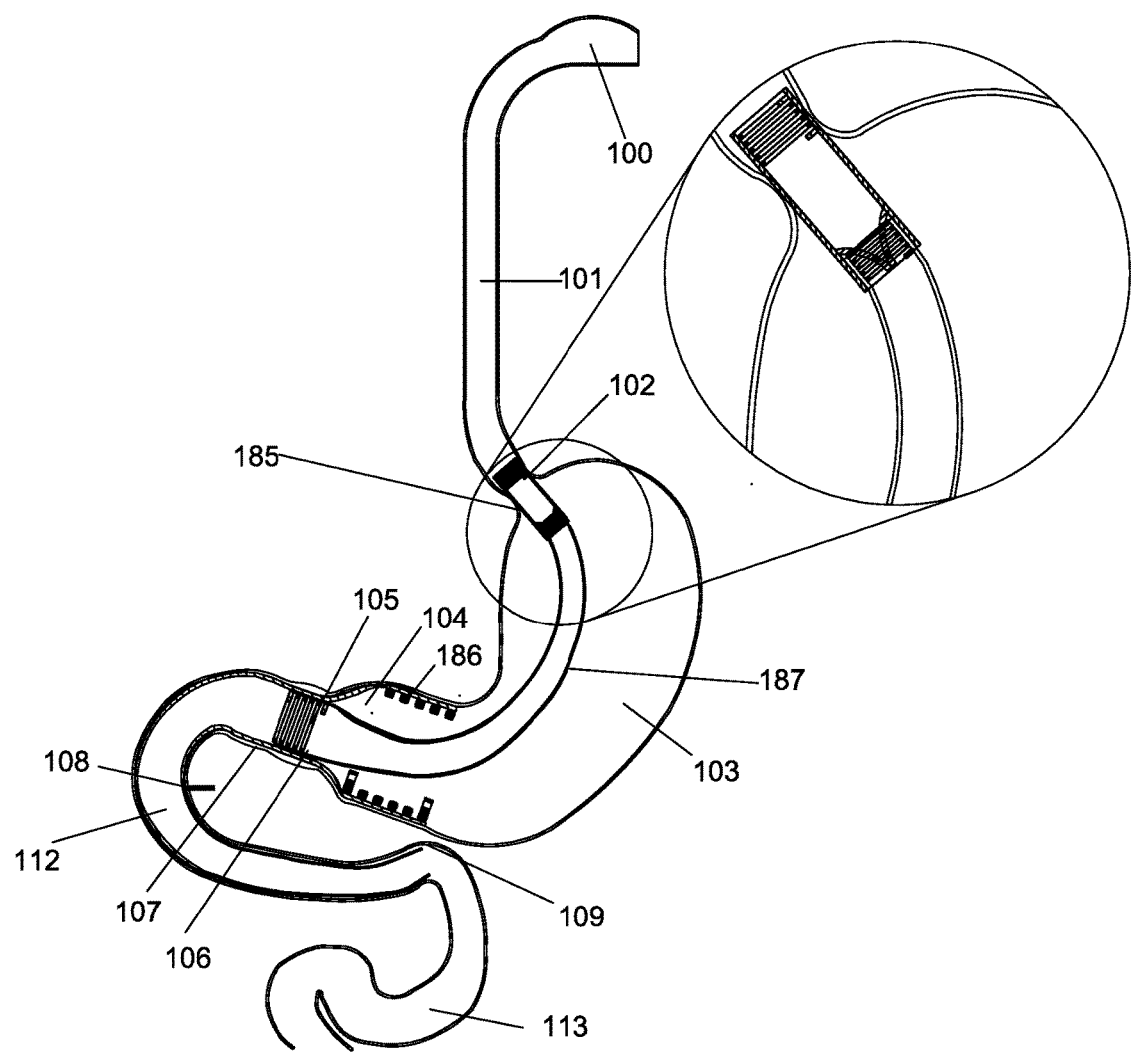
FIG. 24 is a sectional view of a portion of the digestive tract in the body. A docking element and tubular implant is implanted in the esophagus at gastro-esophageal junction. The modular implant has an-anti reflux valve. A second docking station and tubular implant is placed in the pyloric antrum and extends to the ligament of treitz. A third docking station and tubular implant connects the esophageal implant and the duodenal implant at the pyloric antrum.

FIG. 24 is an alternative embodiment of the invention wherein a first docking element 185 with an anti-reflex valve is implanted in the gastro-esophageal junction 102, a second docking element 186 and tubular implant is implanted from the pyloric antrum 104 to the ligament of treitz. A third docking element and tubular implant 187 is implanted from the docking element 185 to the docking element 186. As shown, the implant 187 includes a stent or stent-like anchoring element, which is adapted for delivery in a compressed configuration and to engage the first docking element 185 in an expanded configuration.

Figure 25:
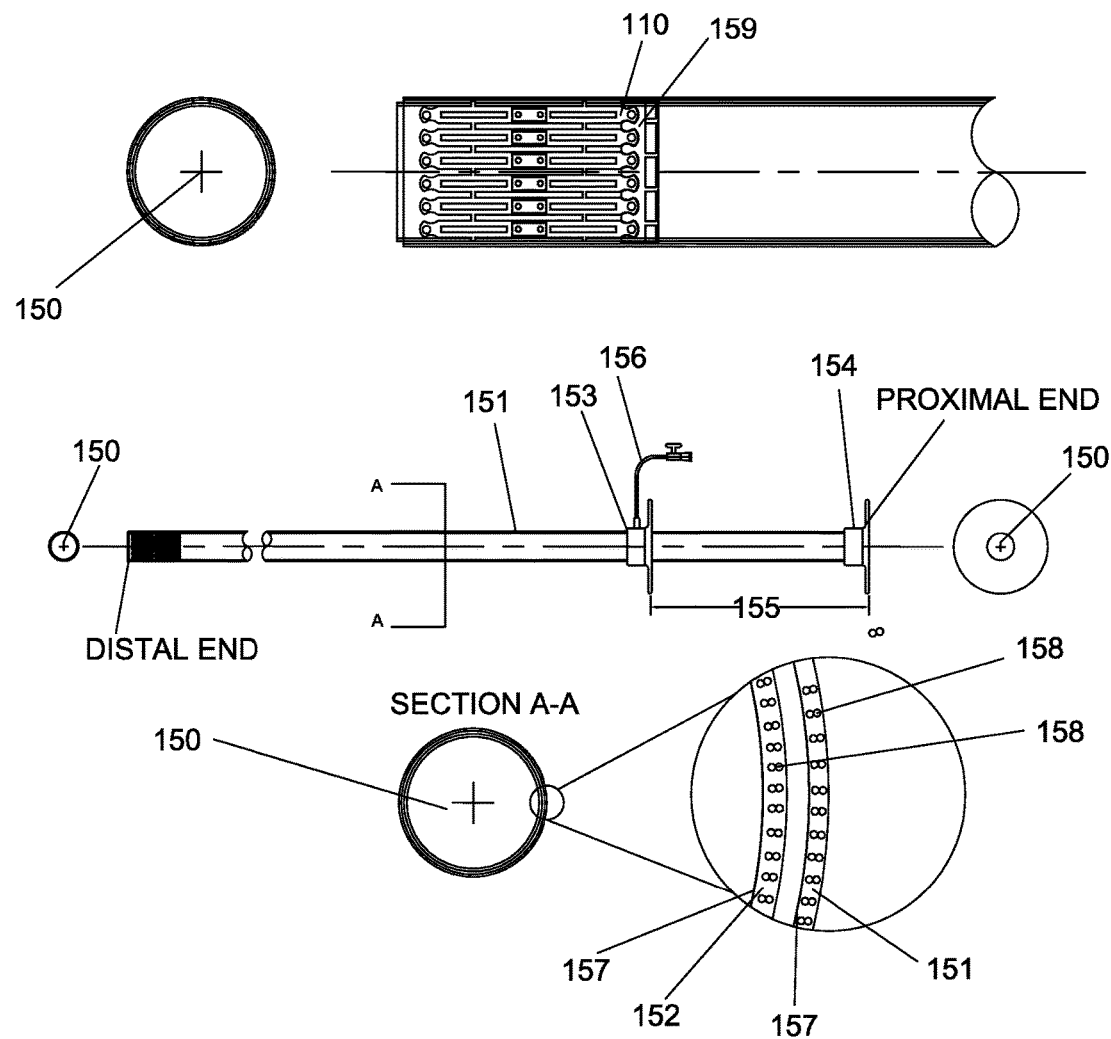
FIG. 25 is a drawing of a delivery catheter with a docking element loaded onto it.

FIG. 25 is a schematic view of a delivery catheter for a self expanding docking element 110, according to embodiments of the invention. As shown in FIG. 25, the catheter is preloaded with the docking element but not the tubular implant. The delivery catheter is constructed with a central lumen 150 sufficiently large to allow the catheter to loaded be over the outside diameter of an endoscope. The delivery catheter consists of an outer catheter 151 and an inner catheter 152. To load the tubular implant onto the delivery catheter the outer sheath handle 153 is retracted towards the inner catheter handle 154 until distance 155 is sufficiently small. Once the tubular implant is loaded over the inner catheter, the outer sheath is partially closed by advancing the outer sheath handle away from the inner sheath handle 154. The outer sheath 151 is then advanced further until the tubular implant is completely (or sufficiently) covered by the outer sheath.

The delivery catheter also has a space on the inner catheter for the modular implant 110 to be loaded. Attached to the inner catheter is a stent retainer 159. The purpose of the stent retainer 159 is to prevent the stent from releasing from the delivery catheter prematurely during deployment. The stent retainer is fastened to the inner catheter. The stent retainer 159 can be made from metal or plastic and can be made radiopaque by making from it from a radiopaque material such as tantalum. The stent retainer has a complementary shape that holds the tips on the stent and does not allow the stent to move distally or forward until the outer sheath 151 is fully retracted to the stent retainer 159. The catheter has a side port 156 which allows the space between the inner and outer sheaths to be flushed with saline. The outer sheath 151 and inner sheath 152 may be made from made from a simple single layer polymer extrusion such as from polyethylene or PTFE. The outer sheath may also be constructed in the following manner. The sheath inner diameter surface is constructed of a thin wall PTFE liner 157. A layer of reinforcement 158 is placed over the PTFE liner, the reinforcement is preferably either a braid of wire or a coil of wire. The wire cross section can be either round or rectangular. The preferred material for the wire is a metal such as 316 or 304 stainless steel or Nitinol or other suitable material. The wire diameters are typically in the 0.0005 inch to 0.010 inch diameter range. The outer jacket material is preferably reflowed into the reinforcement layer by melting the material and flowing it into the spaces in between the braided wire or the coil wires.

Figure 26:
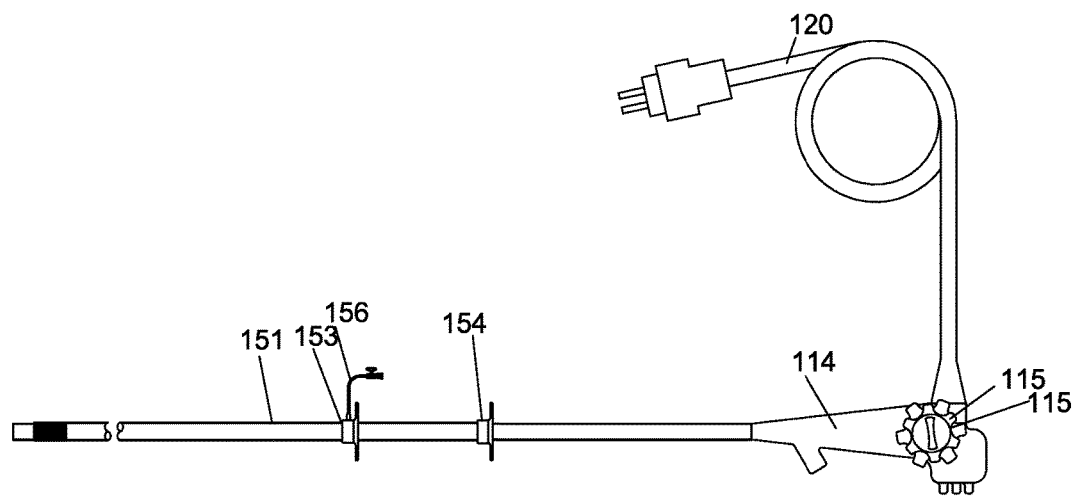
FIG. 26 is a drawing of a delivery catheter with the endoscope inserted through inner diameter of the delivery catheter.
Figure 27:
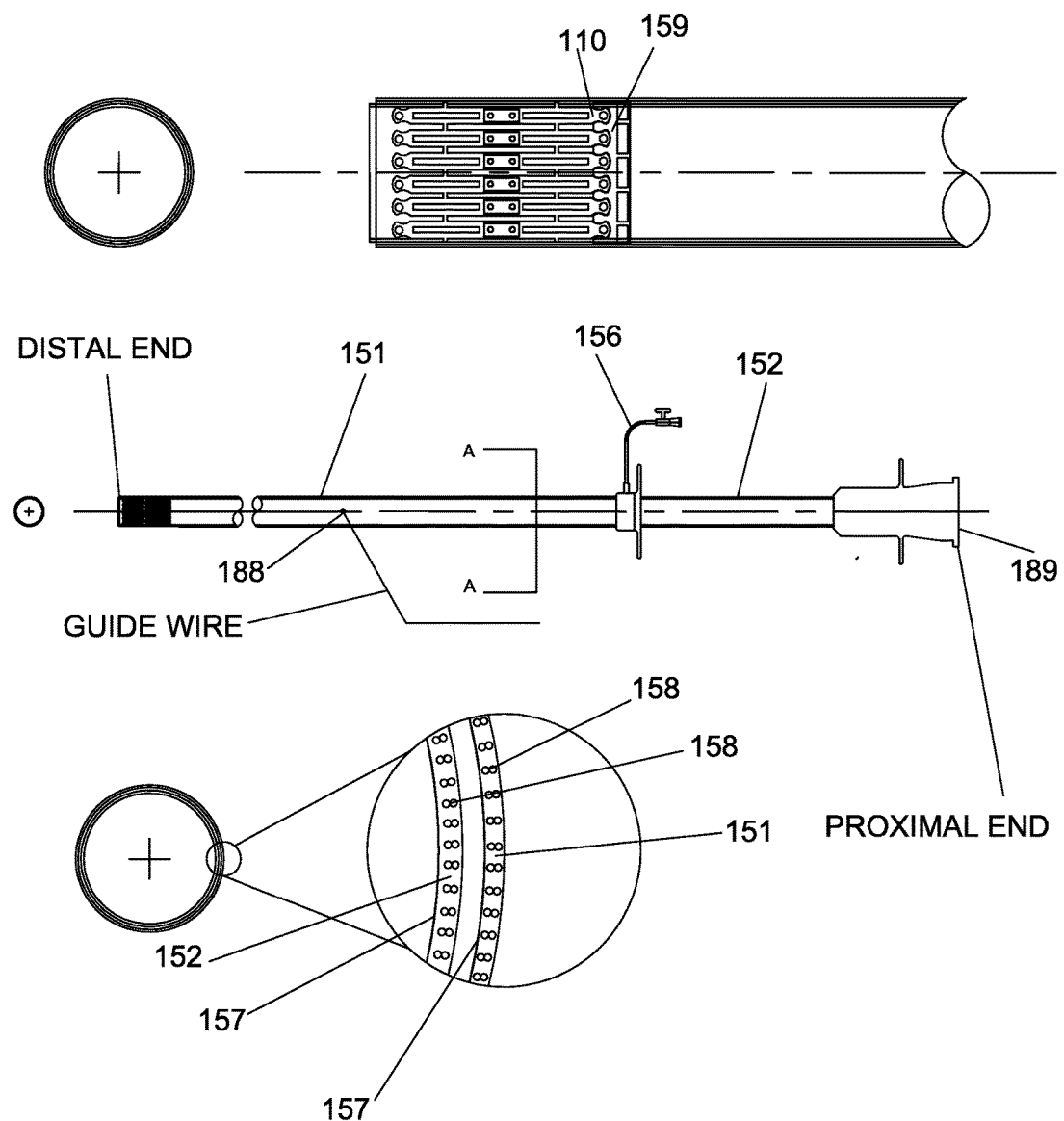
FIG. 27 is a drawing of a delivery catheter which is designed to be inserted through the working channel of the endoscope.

FIG. 26 is a schematic view showing the delivery catheter for the apparatus disclosed loaded over an endoscope. FIG. 27 is a schematic view of an alternative delivery catheter for a self expanding docking element 110, tubular implant 111 or for both 110 and 111 on the same catheter. The delivery catheter is constructed with a smaller outside diameter to allow the catheter to be inserted through the working channel of the endoscope 114. The delivery catheter consists of an outer catheter 151 and an inner catheter 152. Attached to the inner catheter is a stent retainer 159. The purpose of the stent retainer 159 is to prevent the stent from releasing from the delivery catheter prematurely during deployment. The stent retainer is fastened to the inner catheter. The stent retainer 159 can be made from metal or plastic and can be made radio-opaque by making from it from a radio-opaque material such as tantalum. The stent retainer has a complementary shape that holds the tips on the stent and does not allow the stent to move distally or forward until the outer sheath 151 is fully retracted to the stent retainer 159.

The catheter has a side port 156 which allows the space between the inner and outer sheaths to be flushed with saline. The outer sheath 151 and inner sheath 152 may be made from made from a simple single layer polymer extrusion such as from polyethylene or PTFE. The outer sheath may also be constructed in the following manner. The sheath inner diameter surface is constructed of a thin wall PTFE liner 157. A layer of reinforcement 158 is placed over the PTFE liner, the reinforcement is preferably either a braid of wire or a coil of wire. The wire cross section can be either round or rectangular. The preferred material for the wire is a metal such as 316 or 304 stainless steel or Nitinol or other suitable material. The wire diameters are typically in the 0.0005 inch to 0.010 inch diameter range. The outer jacket material is preferably reflowed into the reinforcement layer by melting the material and flowing it into the spaces in between the braided wire or the coil wires. The outside diameter of this catheter will range typically from 1 mm to 4 mm. The catheter can be constructed to be an over the wire catheter or a rapid exchange catheter. For a rapid exchange design the guidewire will enter the central lumen of the distal end of the catheter and exit at point 188. For an over the wire catheter design the guidewire will enter the central lumen of the distal end of the catheter and exit at point 189.

Figure 28:
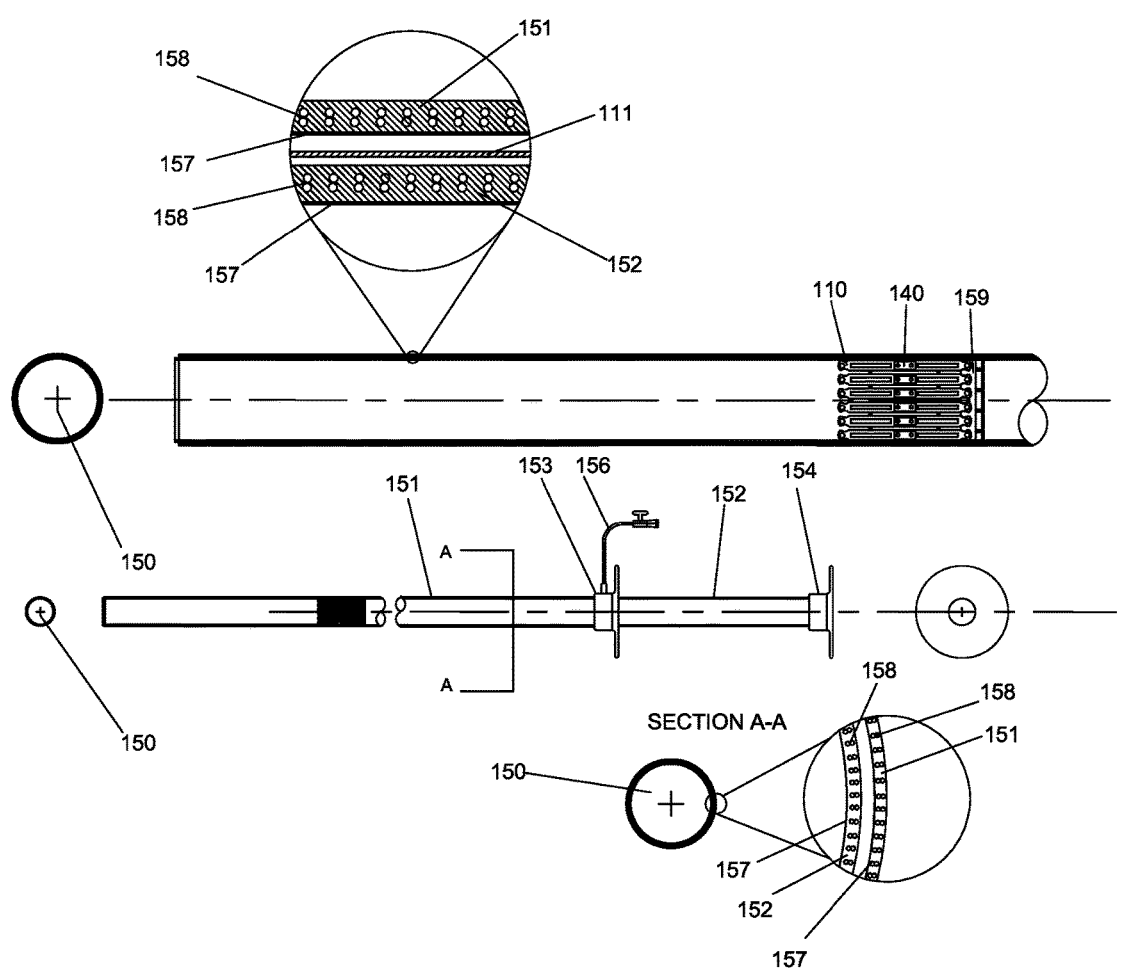
FIG. 28 is a drawing of a delivery catheter with a docking element and tubular implant loaded onto it.

FIG. 28 is a schematic view of an alternative embodiment drawing of a delivery catheter for a self expanding docking element 110 and tubular implant 111. As shown in FIG. 28, the tubular implant is located distal to the docking element. The delivery catheter could also be used for delivery of a stented sleeve construct where the sleeve and stent are integrated together into one implant. The delivery catheter is constructed with a central lumen 150 large enough to allow the catheter to loaded be over the outside diameter of the endoscope 114. The delivery catheter consists of an outer catheter 151 and an inner catheter 152. To load the tubular implant onto the delivery catheter, the outer sheath handle 153 is retracted towards the inner catheter handle 154 until distance 155 is a sufficiently small. The outer sheath is then partially closed by advancing the outer sheath handle away from the inner sheath handle 154. The outer sheath 151 is then further advanced until the tubular implant is completely (or sufficiently) covered by the outer sheath. The delivery catheter also has a space on the inner catheter for the modular implant 110 to be loaded. Attached to the inner catheter is a stent retainer 159. The purpose of the stent retainer 159 is to prevent the stent from releasing from the delivery catheter prematurely during deployment. The stent retainer is fastened to the inner catheter. The stent retainer 159 can be made from metal or plastic and can be made radio-opaque by making from it from a radioopaque material such as tantalum. The stent retainer has a complementary shape that holds the tips on the stent and does not allow the stent to move distally or forward until the outer sheath 151 is fully retracted to the stent retainer 159.

The catheter has a side port 156 which allows the space between the inner and outer sheaths to be flushed with saline. The outer sheath 151 and inner sheath 152 may be made from made from a simple single layer polymer extrusion such as from polyethylene or PTFE. The outer sheath may also be constructed in the following manner. The sheath inner diameter surface is constructed of a thin wall PTFE liner 157. A layer of reinforcement 158 is placed over the PTFE liner, the reinforcement is preferably either a braid of wire or a coil of wire. The wire cross section can be either round or rectangular. The preferred material for the wire is a metal such as 316, 304 stainless steel, Nitinol or other suitable material. The wire diameters are typically in the 0.0005 inch to 0.010 inch diameter range. The outer jacket material is preferably reflowed into the reinforcement layer by melting the material and flowing the melted polymer into the spaces in between the braided wire or the coiled wires.

Figure 29:
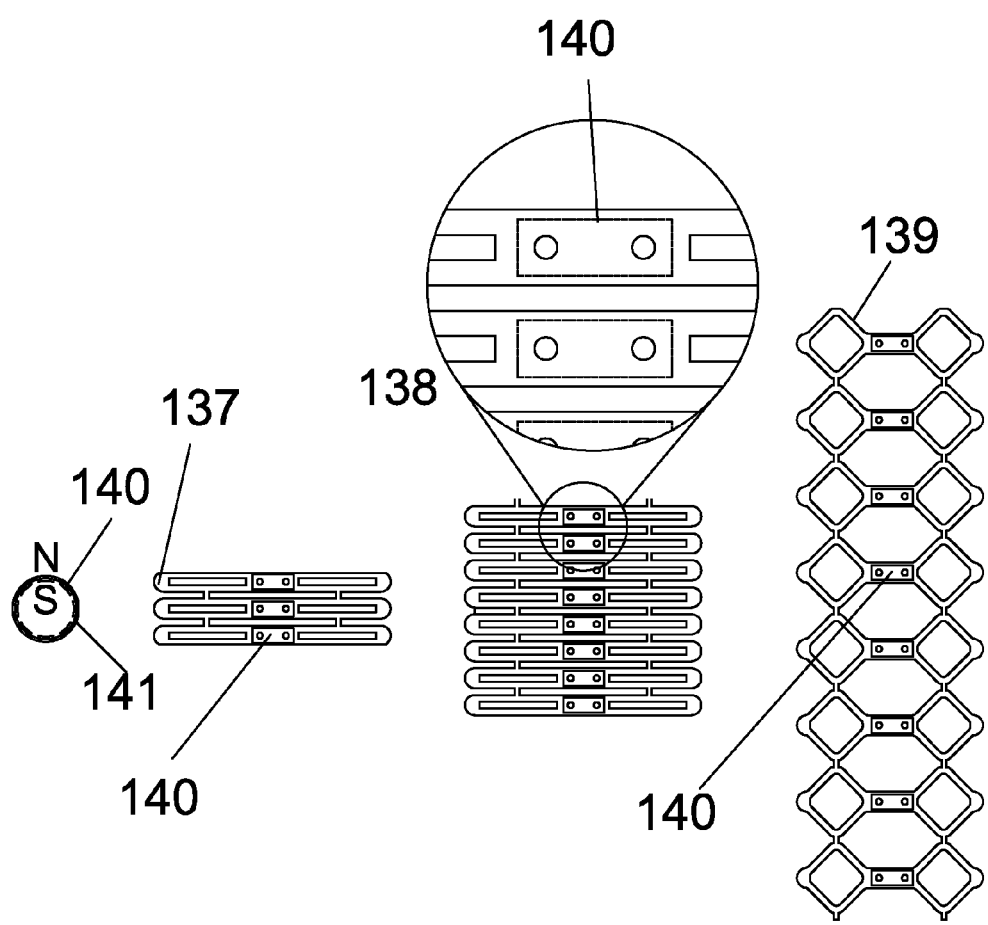
FIGS. 29-35 show a variety of stents that can be used as a docking element.

FIG. 29 is a drawing of a stent that can used as a docking element. Stent 137 stent is preferably laser cut from a round metal tubing or from a flat sheet of metal. The flat representation of the stent circumference is shown in item 138. The flat representation of an expanded stent is shown in item 139. The end view of the stent is shown 141. Magnets 140 are attached to the stent on the inside diameter. The magnets may be attached to the stent by use of a mechanical fastener, glue, suture, welding, snap fit or other suitable means. The stent can be either balloon expandable or self expanding. The magnets may be located in middle of the stent or at the ends of the stent. Suitable materials for the magnets include, for example, neodymium-iron-boron [Nd—Fe—B], samarium-cobalt [Sm—Co], alnico, and hard ferrite [ceramic] or other suitable material. The stent may be balloon expanded or self expanding.

Figure 30:
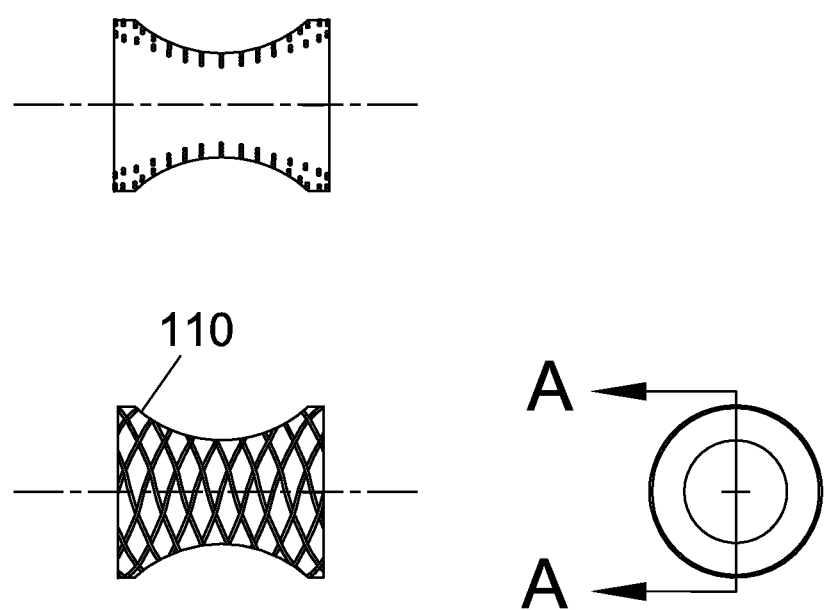

FIG. 30 is a drawing of a stent that can be used as a docking or anchoring element 110. The stent can be laser cut from metal tubing or from a flat sheet of metal. The stent can also be braided or woven from round or flat wire. As shown in FIG. 30, the stent has a double-layer mesh construction and it can a have separation between the two layers to allow other mechanical elements attached to mating tubular implant to mechanically interlock with the stent without exerting any anchoring force against the tissue.

In the picture shown, the stent has a narrowed diameter in the midpoint of the length this will provide for the stent to anchor more securely in anatomical locations such as the pylorus 106. According to other embodiments, the stent has a cylindrical or other shape of double layer construction like a dumbbell shape. The mesh of the stent may be left open or it may be covered with a suitable material previously disclosed in this application. Magnets or other mechanical means for attachment of a tubular implant may be incorporated as disclosed in this application. The stent may be balloon expanded or self expanding. The mesh of the stent may be left open or it may be covered with a suitable material previously disclosed in this application. While the preferred embodiment of the above stent is a double-layer mesh construction, other single or multi-layer constructs which create hollow space within the structure to permit interlocking with other tubular implants could also be used. The space between the two mesh layers of the stent also help prevent or minimize tissue in-growth reaching the second (i.e., inner) layer of the stent and likewise from reaching an tubular or therapy implant coupled to the inner layer of the stent. Preventing or minimizing such tissue in-growth facilitates safe and easy removal (or replacement) of any such tubular or therapy implant.

Figure 31A:
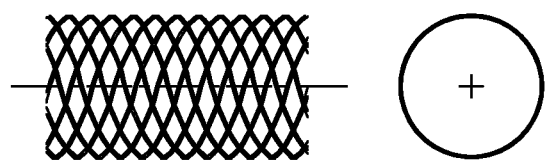
Figure 31B:
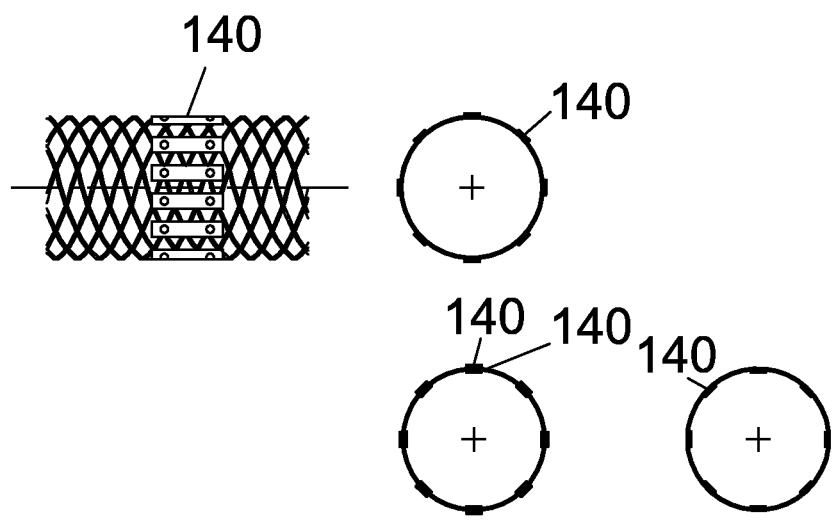

FIG. 31A is a drawing of a stent that can be used as a docking or anchoring element. The stent can be braided from round or flat wire. As depicted in FIG. 31A, the stent is in the expanded state. The mesh of the stent may be left open or it may be covered with a suitable material, as previously disclosed in this application. The stent may be balloon expanded or self expanding. The mesh of the stent may be left open or it may be covered with a suitable material previously disclosed in this application. FIG. 31B is a drawing of a stent that can be used as a docking element. The stent can be braided from round or flat wire. As depicted in FIG. 31B, the stent is in the expanded state. The stent may include magnets 140 attached to the stent. The magnets may be on the inside diameter, outside diameter, both the inside or outside diameter or incorporated into the wall. The magnets can be used as a means to attach a tubular implant such as 111. The mesh of the stent may be left open or it may be covered with a suitable material previously disclosed in this application. The stent may be balloon expanded or self expanding. The mesh of the stent may be left open or it may be covered with a suitable material, as previously disclosed in this application.

Figure 32A:
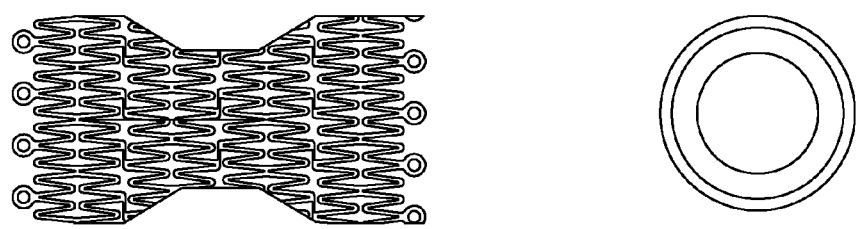
Figure 32B:
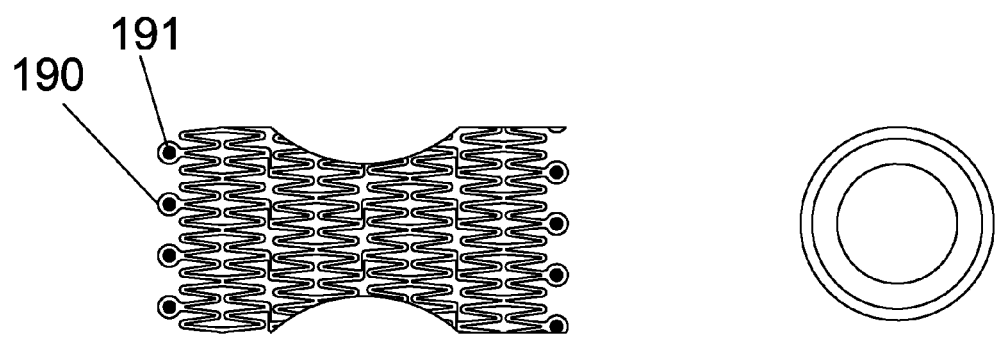

FIG. 32A is a drawing of a stent that can be used as a docking or anchoring element. The stent may be laser cut from round metal tubing or from a flat sheet of metal. The central portion of the stents diameter may be set to a smaller diameter to provide increased resistance to stent migration. The stent may be balloon expanded or self expanding. The mesh of the stent may be left open or it may be covered with a suitable material previously disclosed in this application. FIG. 32B is a drawing of a stent that can be used as a docking element. The stent may be laser cut from round metal tubing or from a flat sheet of metal. The central portion of the stents diameter may be shaped to an hour glass shape to provide increased resistance to stent migration. As shown in FIG. 32B, the stent has hoops 190 at the end of the stent. The hoops may be used to interlock with a stent retainer 159 on the inner catheter 152 to prevent premature deployment for the sheath is full y retracted. Radiopaque markers 191 can be attached to the end of the stent to increase the radiopacity of the stent. A metal insert may be pressed or swaged into the hoops 190. The insert may be made from a high atomic density material such as tantalum, gold, platinum or iridium. The insert may take form of a disk or sphere and may be plastically deformed to fill the hoop cavity. The stent may be balloon expanded or self expanding. The mesh of the stent may be left open or it may be covered with a suitable material previously disclosed in this application.

Figure 33A:
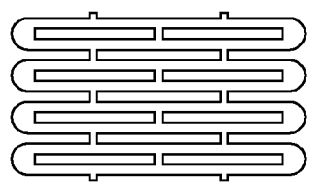
Figure 33A:
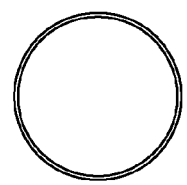
Figure 33B:
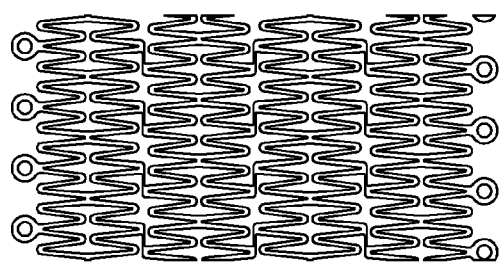
Figure 33B:
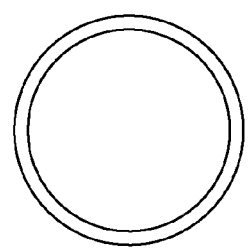

FIG. 33A is a drawing of a stent that can be used as a docking element. Stent is preferably laser cut from round metal tubing or from a flat sheet of metal. The stent may be balloon expanded or self expanding. The mesh of the stent may be left open or it may be covered with a suitable material previously disclosed in this application. FIG. 33B is a drawing of a stent that can be used as a docking element. Stent is preferably laser cut from round metal tubing or from a flat sheet of metal. The stent may be balloon expanded or self expanding. The mesh of the stent may be left open or it may be covered with a suitable material previously disclosed in this application.

Figure 34A:
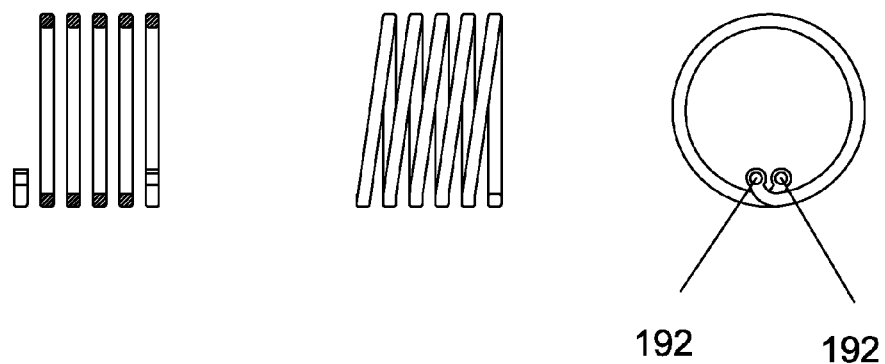
Figure 34B:
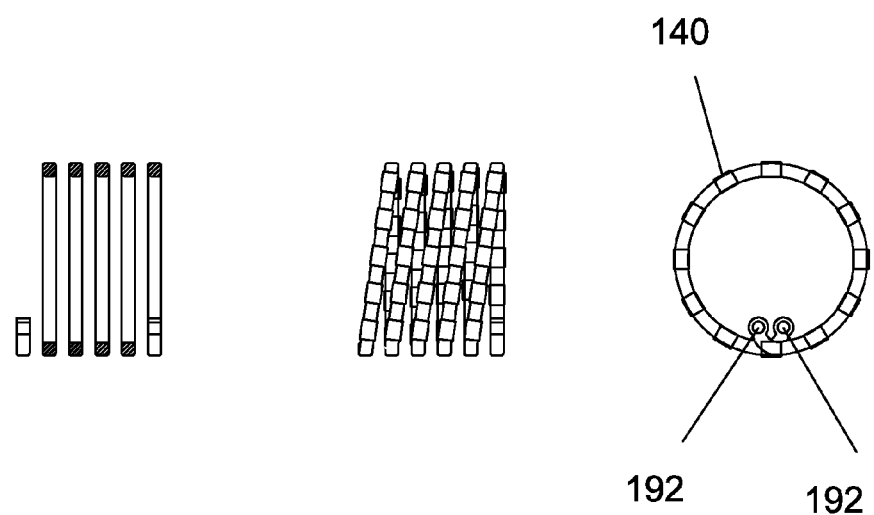

FIG. 34A is a drawing of a coil stent that can be used as a docking element. Stent is preferably made from round or flat wire. The stent is preferably self expanding, but may be made to be balloon expandable. The stent also may be laser cut into a coil from tubing. The preferred material for the stent is Nitinol. The mesh of the stent may be left open or it may be covered with a suitable material previously disclosed in this application. The stent has a hoop 192 at each end of the coil. The stent can be wound down onto a catheter by inserting a pin into the hoops on each end of the stent and rotating the pins in opposite directions to cause the stent to wind down onto the catheter. FIG. 34B is a drawing of a coil stent that can be used as a docking element. The stent is preferably made from round or flat wire. The stent is preferably self expanding, but may be made to be balloon expandable. The stent also may be laser cut into a coil from tubing. The preferred material for the stent is Nitinol. The mesh of the stent may be left open or it may be covered with a suitable material previously disclosed in this application. The stent has a hoop 192 at each end of the coil. The stent can be wound down onto a catheter by inserting a pin into the hoops on each end of the stent and rotating the pins in opposite directions to cause the stent to wind down onto the catheter. The stent has magnets 140 and the coil of the stent. The magnets can be used as an attachment means to a tubular implant.

Figure 35:
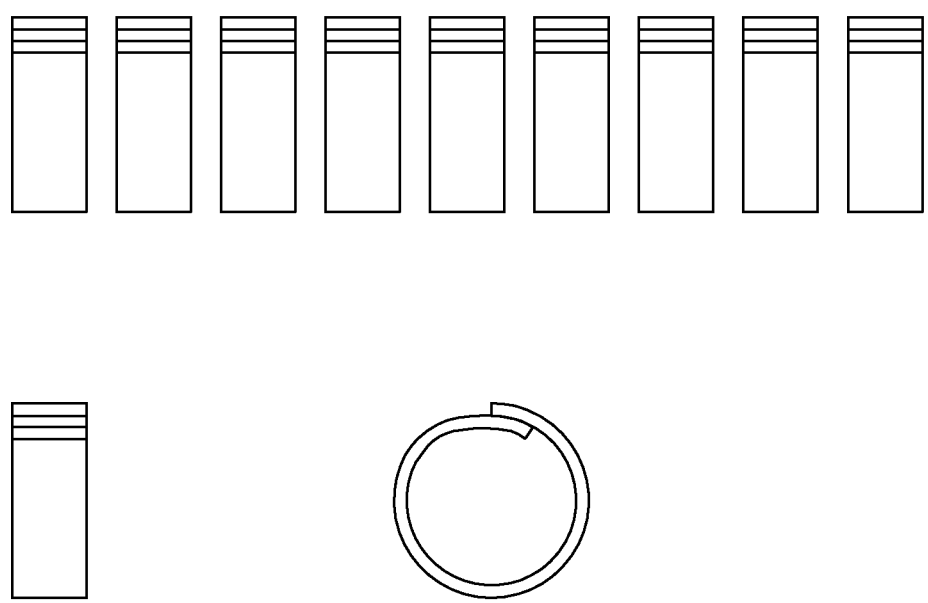

FIG. 35 is a drawing of a coil stent that can be used as a docking element. The stent is preferably made from wire or sheet Nitinol metal. Several stents in series adjacent to each other can be used to form the docking element.

Figure 36:
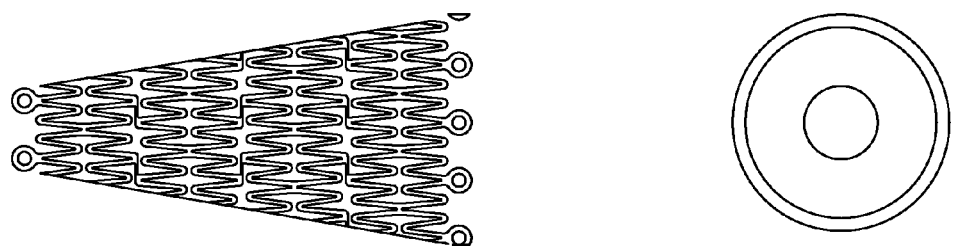
FIG. 36A is a drawing of a stent that can be used as a docking element.
FIG. 36B is a drawing of a stent that can be used as a docking element.
Figure 36B:
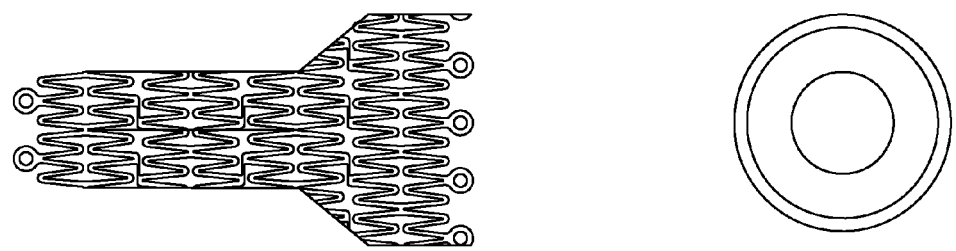

FIG. 36A is a drawing of a stent that can be used as a docking element. Stent is preferably laser cut from round metal tubing or from a flat sheet of metal. The stent is shaped to a conical shape to provide increased resistance to stent migration and to more closely fit the anatomy. The stent may be balloon expanded or self expanding. The mesh of the stent may be left open or it may be covered with a suitable material previously disclosed in this application. FIG. 36B is a drawing of a stent that can be used as a docking element. Stent is preferably laser cut from round metal tubing or from a flat sheet of metal. The stent is shaped to a have a stepped diameter to provide increased resistance to stent migration and to more closely fit the anatomy. The stent may be balloon expanded or self expanding. The mesh of the stent may be left open or it may be covered with a suitable material previously disclosed in this application.

Figure 37:
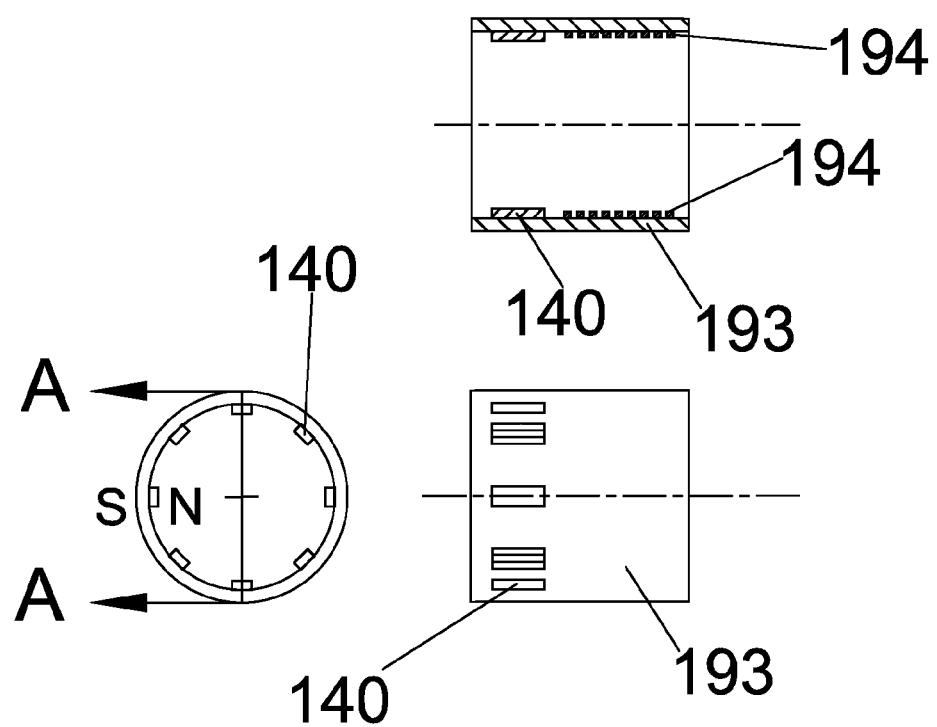
FIGS. 37-39 show docking elements.

FIG. 37 shows schematic views of a docking element. The docking element is composed of three primary components: A stent 194, a sleeve material 193 and magnets 140. The stent can be self expanding or balloon expandable. The sleeve can be any suitable material, as was previously disclosed in this application. The magnets may be attached to the sleeve by adhesive or mechanical fasteners such as rivets, screws, suture or mechanical interlocking.

Figure 38:
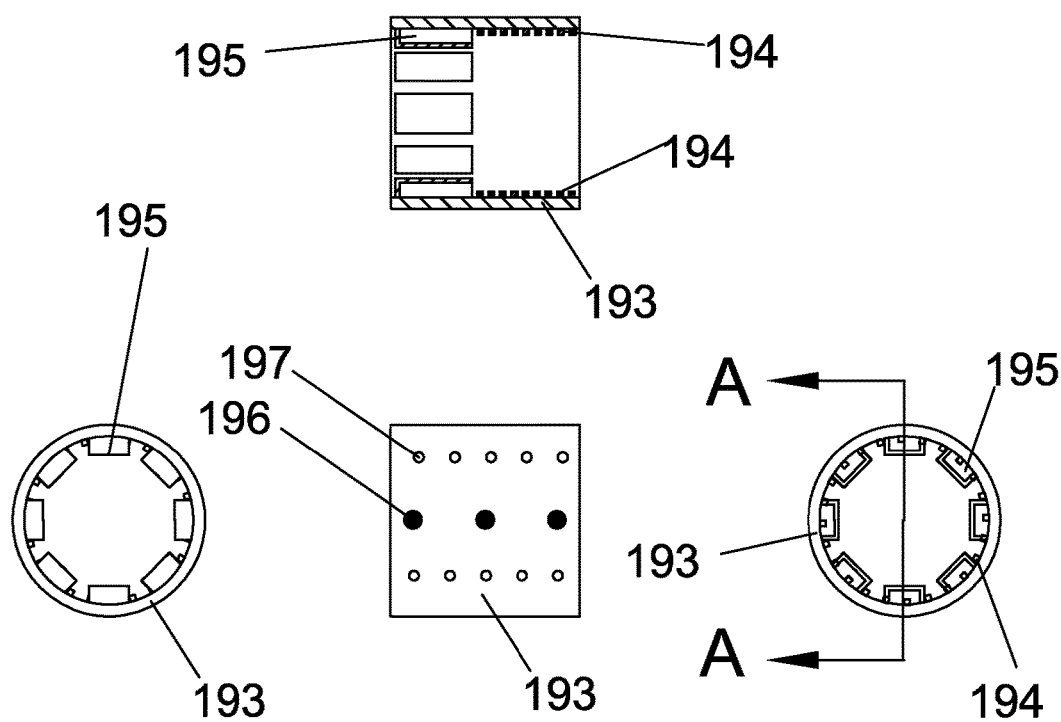

FIG. 38 shows schematic views of a docking element. The docking element is composed of four primary components: A stent 194, a sleeve material 193, radio-opaque markers 196 and pockets 195. The stent can be self expanding or balloon expandable. The sleeve can be made from any suitable material, as was previously disclosed in this application. The pockets 195 are like small sleeves that are created in the sleeve material 194. The pockets 195 may be made by sewing or by the use of a mechanical fastener. The pockets 195 form receptacles to hold magnets or other fasteners that will be delivered to the pocket, such that the docking element may be assembled in-situ. This design allows much larger magnetic or mechanical fastening elements to be incorporated into the docking element. A guide wire may be inserted into the pockets and the magnets or fasteners can be advanced over the guide wire into the pocket under endoscopic guidance. The sleeve may have holes 197 cut into it to allow some fluid transfer through the docking element if desired.

Figure 39:
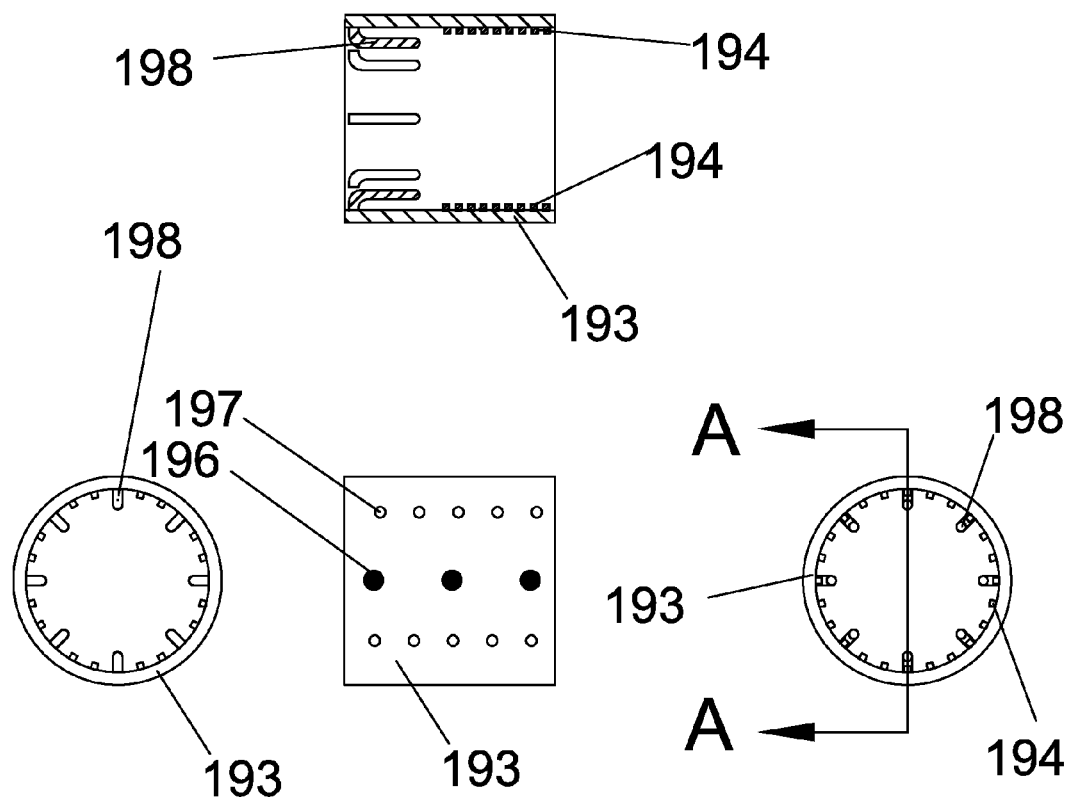

FIG. 39 is a drawing of a docking element. The docking element is composed of four primary components: A stent 194, a sleeve material 193, radio-opaque markers 196 and hooks 198. The stent can be self expanding or balloon expandable. The sleeve can be made from any suitable material as was previously disclosed in this application. The hooks 198 are made from metal or plastic and are attached by adhesive, mechanical means or integrated into the sleeve material. The hooks serve as a docking feature for coupling with a corresponding feature on a tubular implant. The sleeve may have holes 197 in it to allow some fluid transfer through the docking element if desired.

Figure 40A:
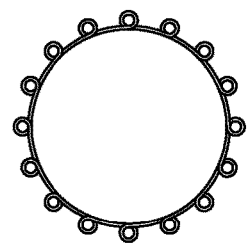
FIG. 40A is an expandable ring that can attached to a sleeve to form a tubular implant.
Figure 40A:
Figure 40B:
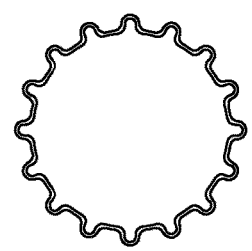
FIG. 40B is an expandable ring that can attached to a sleeve to form a tubular implant.
Figure 40B:
Figure 40C:
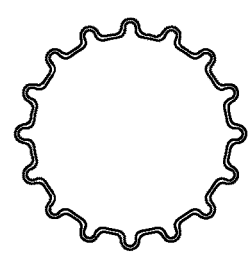
FIG. 40C is an expandable ring that can attached to a sleeve to form a tubular implant.
Figure 40C:
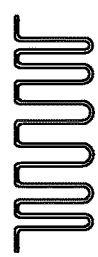

FIGS. 40A-40C show expandable rings that can be attached to a sleeve to form a tubular implant 111. The rings can be made of metal or plastic and can be self expanding or balloon expandable. In various embodiments, the rings are made of Nitinol. The expandable rings serve as coupling feature that operate to releasably couple the tubular implant 111 to a docking feature on the docking or anchoring element 110.

Figure 41:
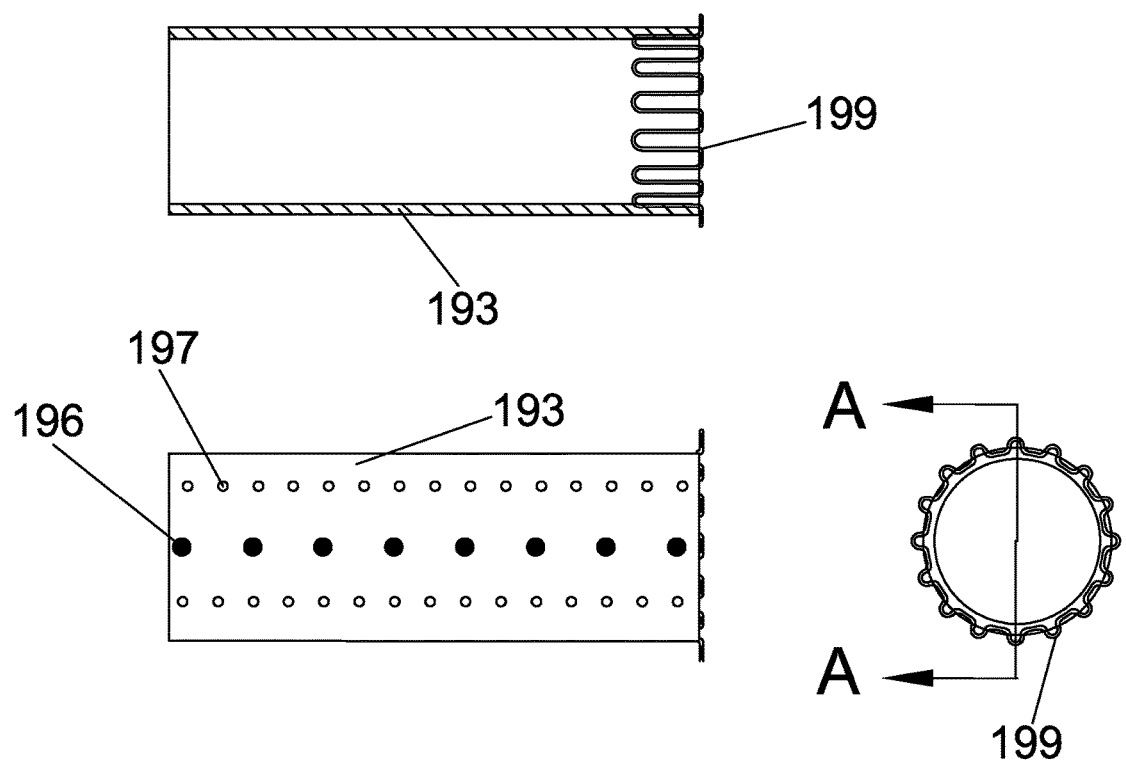
FIG. 41 is a tubular implant that uses an expandable ring as in FIG. 40A, 40B or 40C as an anchoring means.
Figure 42:
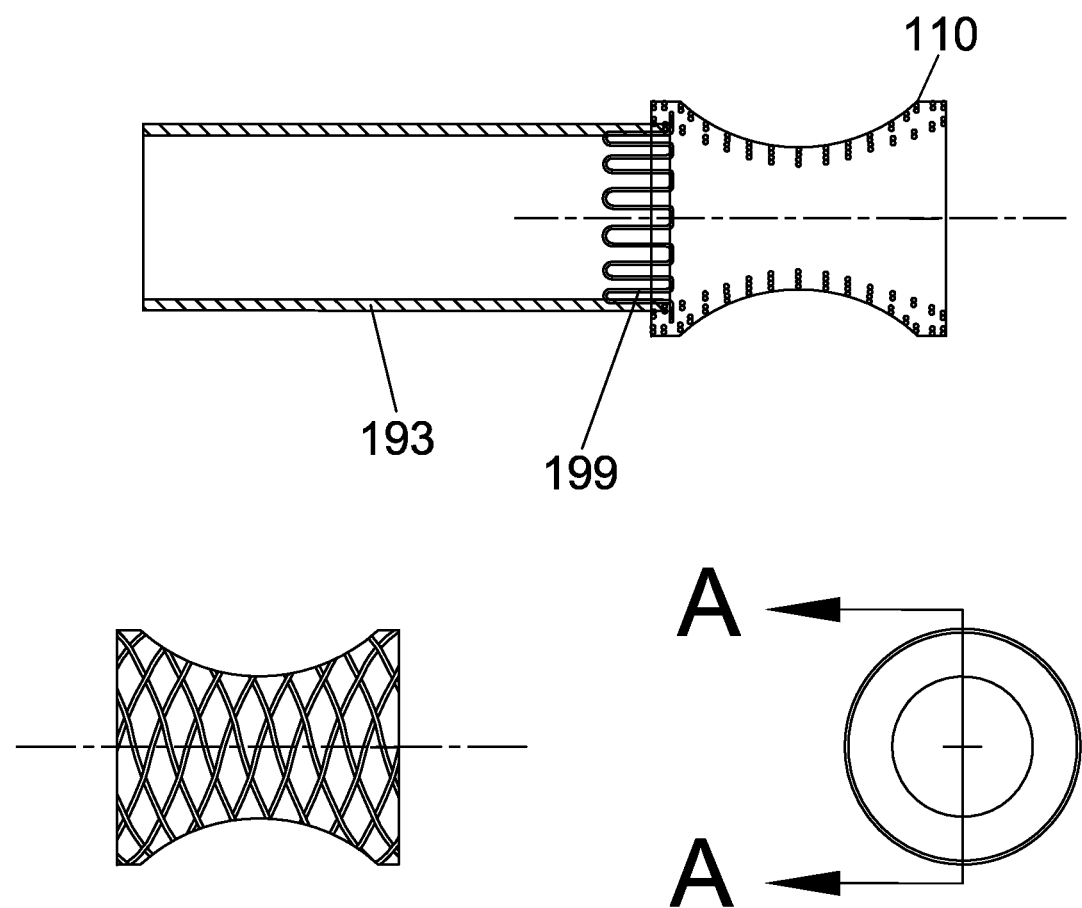
FIG. 42 is a tubular implant that uses an expandable ring as in FIG. 40A, 40B or 40C as an anchoring means. The tubular implant is placed and secured within a docking element.
Figure 43:
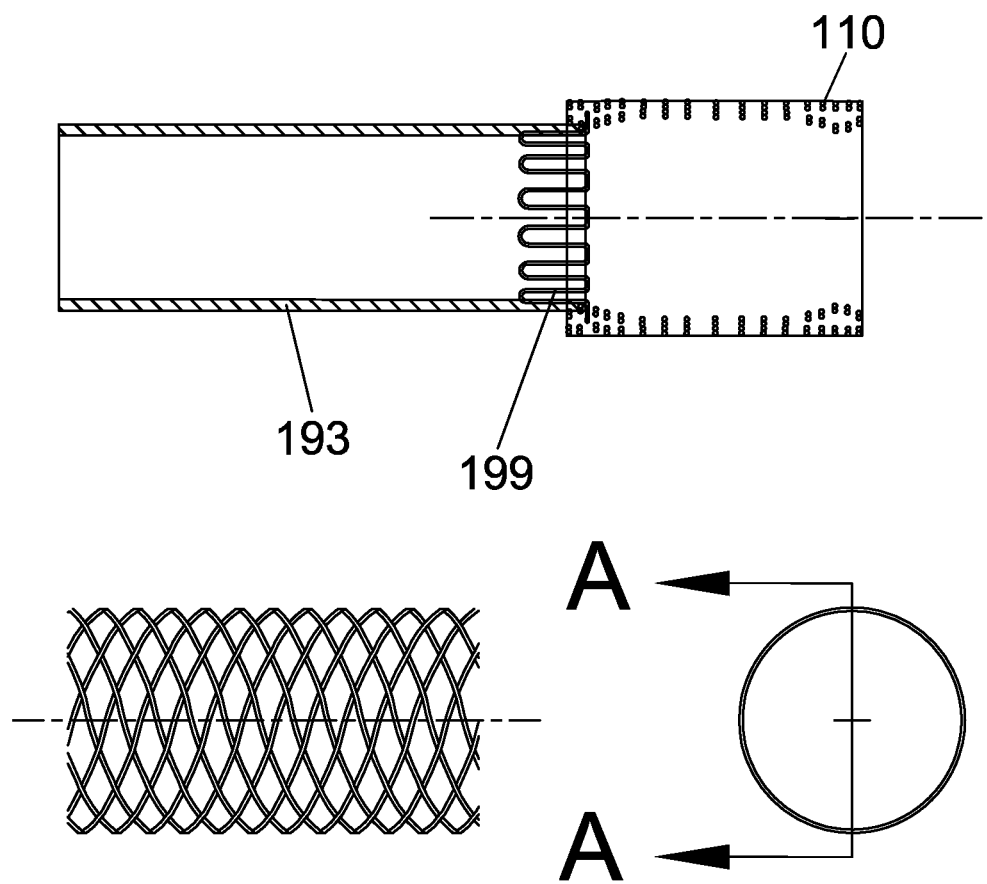
FIG. 43 is a tubular implant that uses an expandable ring as in FIG. 40A, 40B or 40C as an anchoring means. The tubular implant is expanded and secured within the docking element.

FIG. 41 is a drawing of a tubular implant. The implant is composed of sleeve material 193, expandable ring 199, and a radiopaque marker 196. The sleeve can be any suitable material as was previously disclosed in this application and the expandable ring can be of any suitable design as disclosed in FIGS. 40A-40C. Holes 197 can be cut into the sleeve to allow drainage through the sleeve. The expandable ring can be fastened to the sleeve by mechanical fasteners such as suture, wire, clips, or by adhesive or other suitable means. FIG. 42 is drawing of a tubular implant with expandable ring 199 and sleeve material 193 placed expanded and anchored to a docking or anchoring element (such as, for example, the anchoring element shown in FIG. 30). FIG. 43 is drawing of a tubular implant with expandable ring 199 and sleeve material 193 placed expanded and anchored to a docking element. The docking element is a modification to FIG. 30. The docking element has the two layers of braid or material, but is it cylindrical without the hour glass shape of FIG. 30. In both FIGS. 42 and 43 the coupling feature of the tubular implant is configured to releasably couple to the inner portion of the stent (i.e., the docking feature) of the docking or anchoring element.

Figure 44:
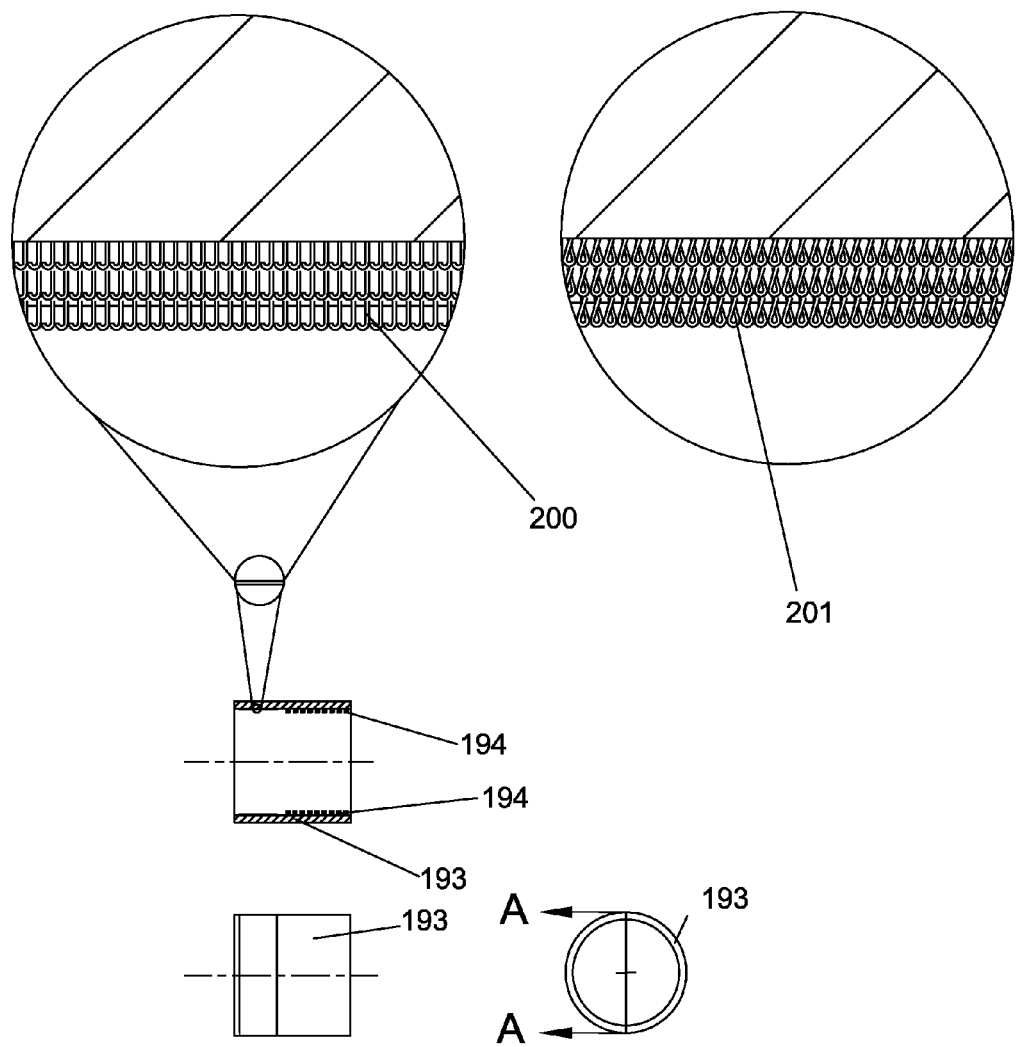
FIG. 44 is a drawing of a docking element which uses hook and loop to secure the tubular implant to docking element.

FIG. 44 shows a docking element composed of three primary components: A stent 194, a sleeve material 193 and hook and loop fastener (velcro) 200 or 201. The stent can be self expanding or balloon expandable. The hook and loop fastener may be sewn or glued onto the sleeve material. The tubular implant that fastens to the docking element of this construction must have the hook fastener if the docking station has the loop fastener or vice-versa.

Figure 45A:
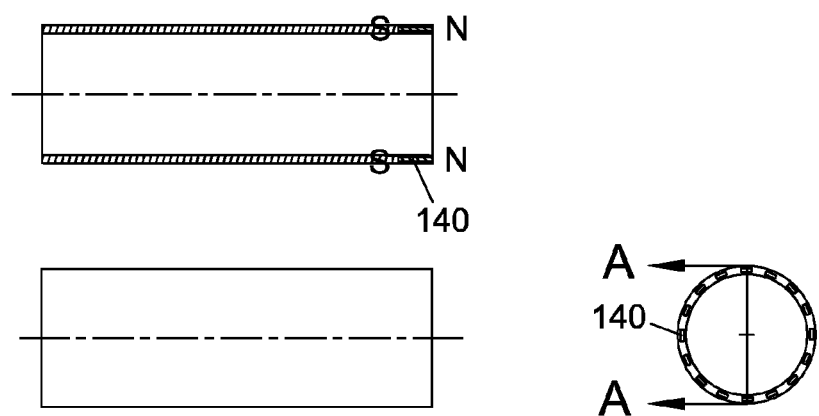
FIG. 45A is a drawing of a tubular implant that has magnets in the wall to allow attachment to another tubular implant or to a docking element.
Figure 45B:
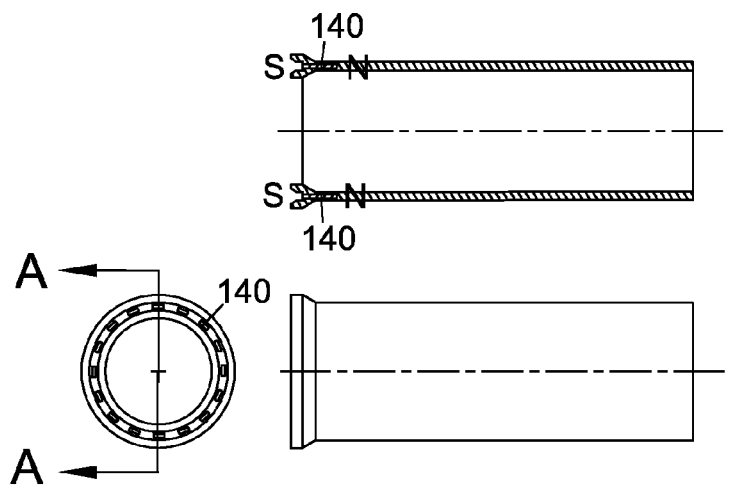
FIG. 45B is a drawing of a tubular implant that has magnets in the wall to allow attachment to another tubular implant or to a docking element, it has a female receptacle to allow attachment to a docking element or other tubular implant.

FIG. 45A is a drawing of a tubular implant. The tubular implant is designed to attach to another tubular implant or to a docking station by a magnetic attachment means. The tubular implant has magnets 140 embedded in the wall. Alternatively, the magnets could be located on either or both of the inner and outer walls. The magnets provide for an end-to-end connection method between components. FIG.

45B shows a tubular implant with a complementary end or female component to match with the male component of FIG. 45A.

Figure 46A:
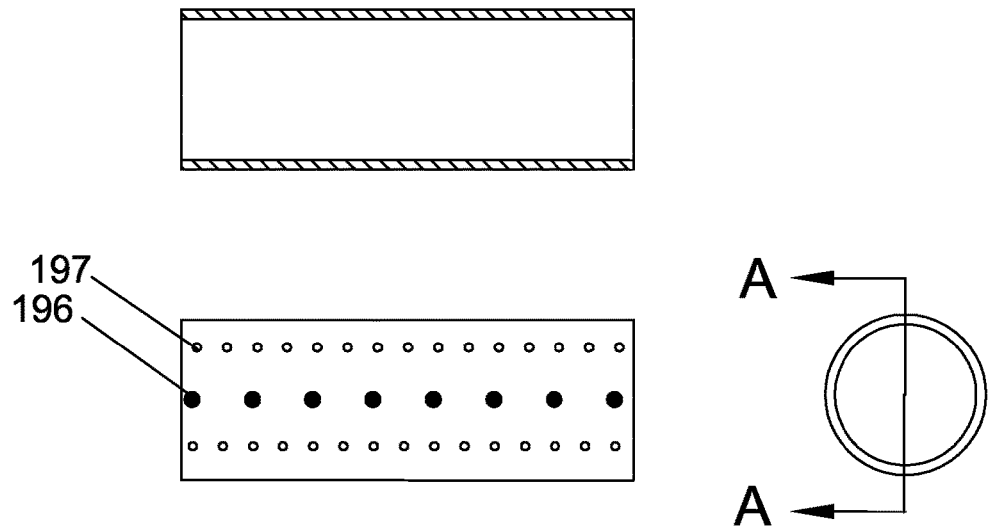
FIGS. 46A and 46B show tubular implants.
Figure 46B:
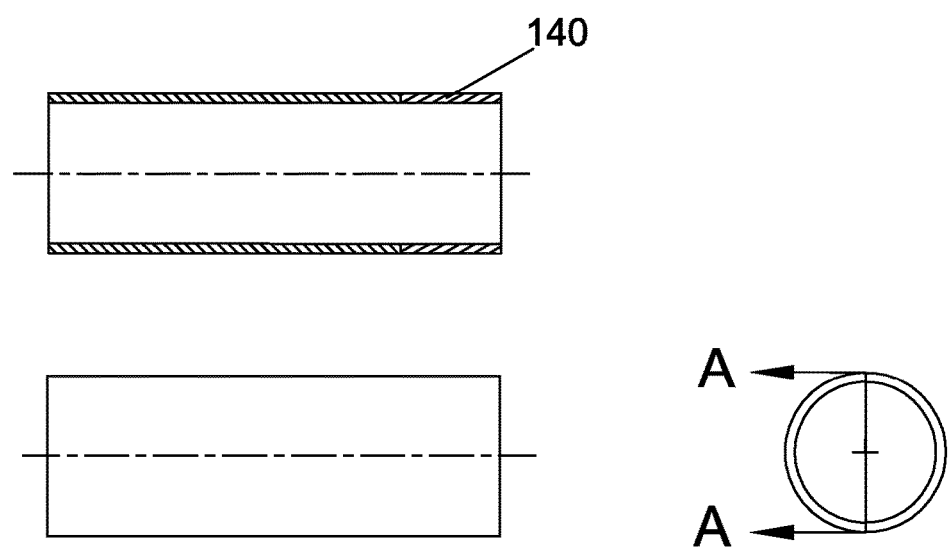

FIG. 46A shows a basic sleeve that is to be used as a component of a docking station, tubular implant, or for extending a tubular implant. The sleeve has radio-opaque markers 196 and may have holes in the sleeve 197 to allow some fluid flow thru the sleeve if required. FIG. 46B shows a basic sleeve that is to be used as a component of a docking station, tubular implant, or for extending a tubular implant. The sleeve has magnetic particles or ferromagnetic material 140 incorporated into the sleeve to allow attachment of the sleeve to a magnetic docking station or tubular implant.

Figure 47A:
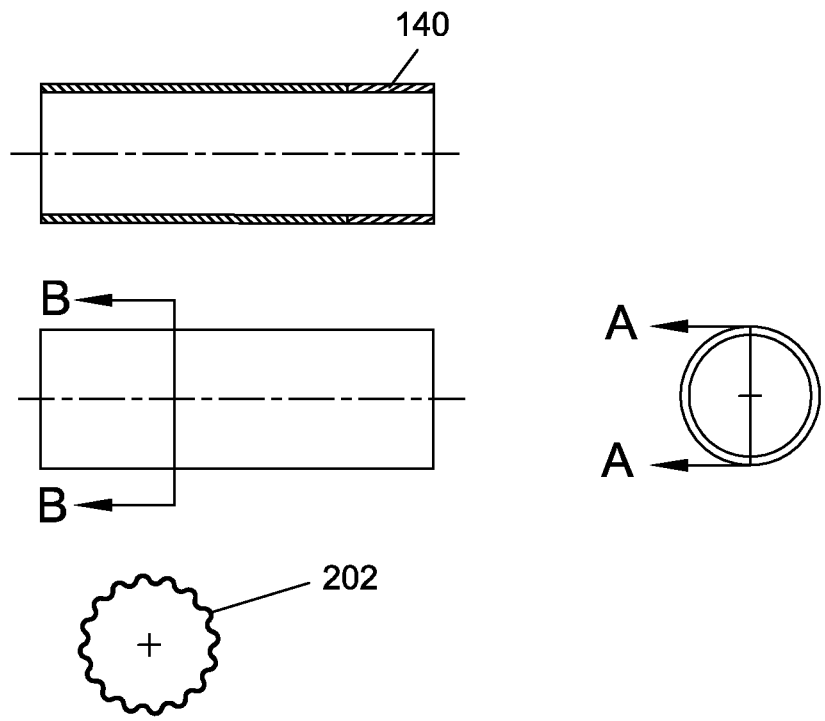
FIGS. 47A and 47B show tubular implants in which the sleeve has longitudinal or circumferential pleats, respectively.
Figure 47B:
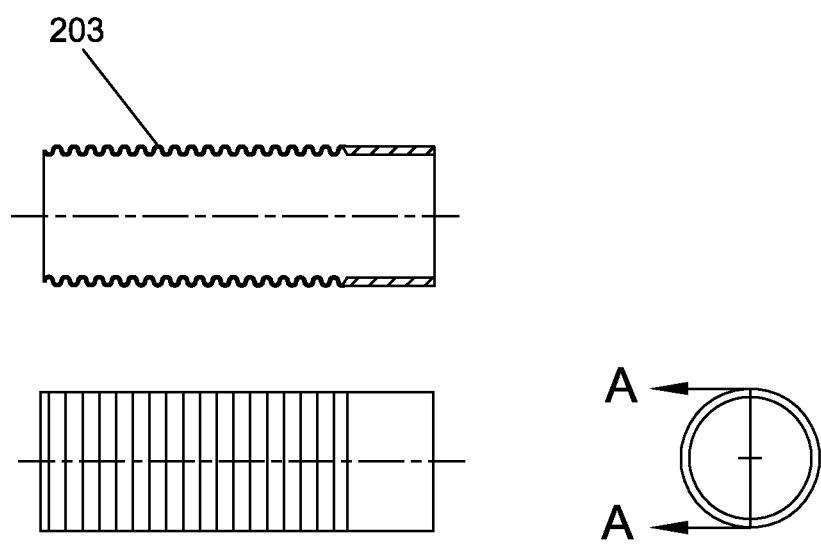

FIG. 47A shows a basic sleeve that is to be used as a component of a docking station, tubular implant, or for extending a tubular implant. The sleeve has magnetic particles or ferromagnetic material 140 incorporated into the sleeve to allow attachment of the sleeve to a magnetic docking station or tubular implant. The sleeve also has longitudinal pleats 202 in the surface to allow it to collapse in diameter more uniformly and may help to reduce the loaded profile. The longitudinal pleats may be over the entire length or only a portion of the diameter or length. FIG. 47B shows a basic sleeve that is to be used as a component of a docking station, tubular implant, or for extending a tubular implant. The sleeve also has pleats around the circumference 203. The circumferential pleats will allow the tubular implant or sleeve to bend easier without kinking.

Figure 48A:
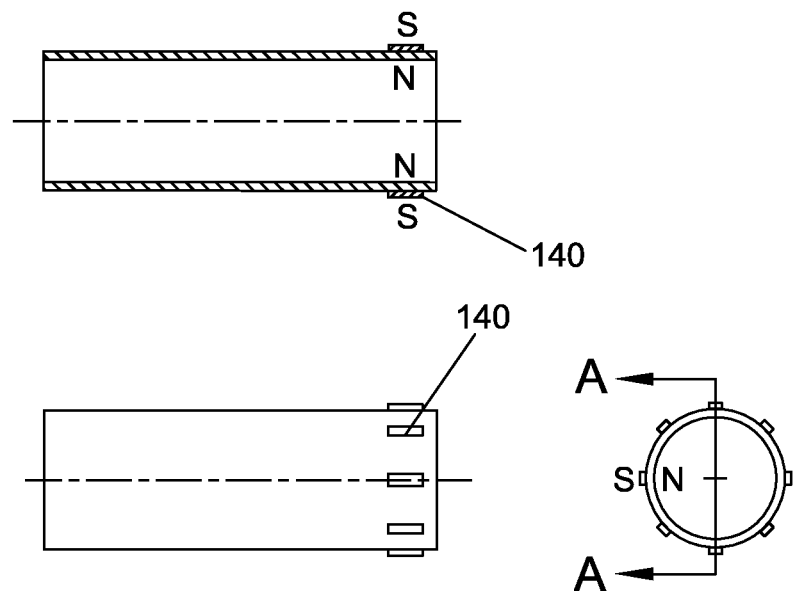
FIGS. 48A and 48B show tubular implants or sleeves with a magnetic attachment means.
Figure 48B:
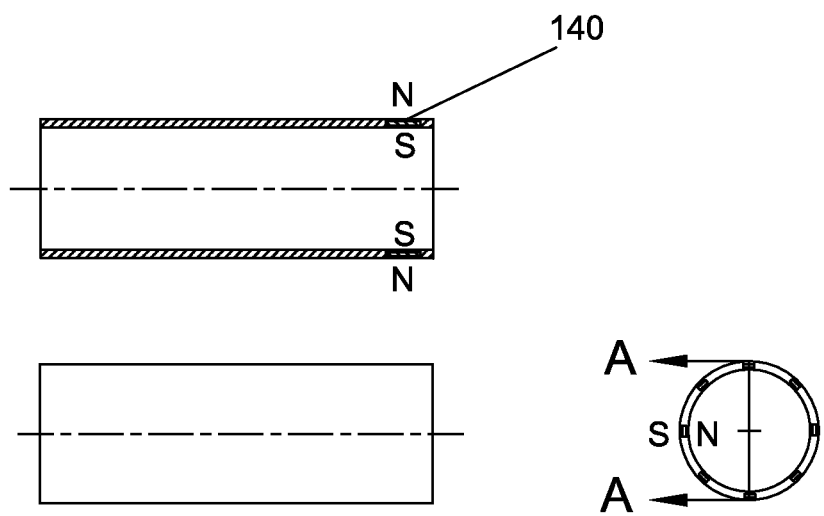

FIG. 48A shows a tubular implant designed to attach to another tubular implant or to a docking station by a magnetic attachment means. The tubular implant has magnets 140 on the outside diameter. FIG. 48B shows a tubular implant designed to attach to another tubular implant or to a docking station by a magnetic attachment means. The tubular implant has magnets 140 in the wall thickness.

Figure 49:
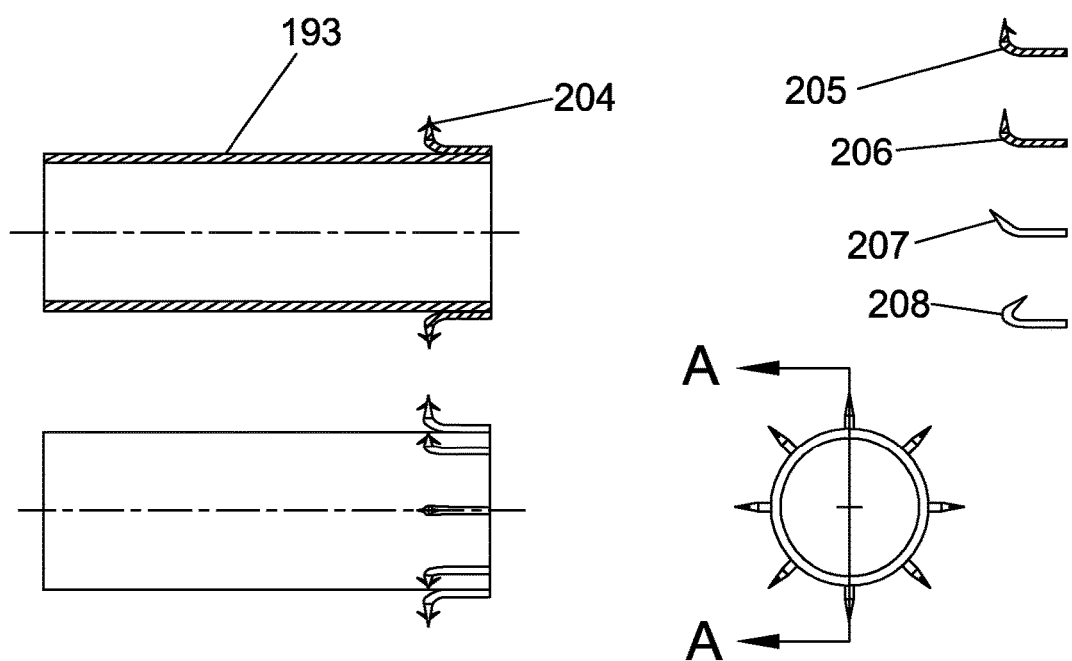
FIG. 49 is a drawing of a tubular implant or sleeve with barbs to attach to attach to tissue or to a docking element.

FIG. 49 shows a tubular implant that is constructed with a sleeve 193 material, and set of barbed hooks 204. Hook 204 has 2 barbs per hook, hook 205 has one barb per hook, hook 206 has no barbs, hook 207 and 208 have different bend angles. The modular implant can attach to a docking element or directly to the anatomy or to another sleeve.

Figure 50A:
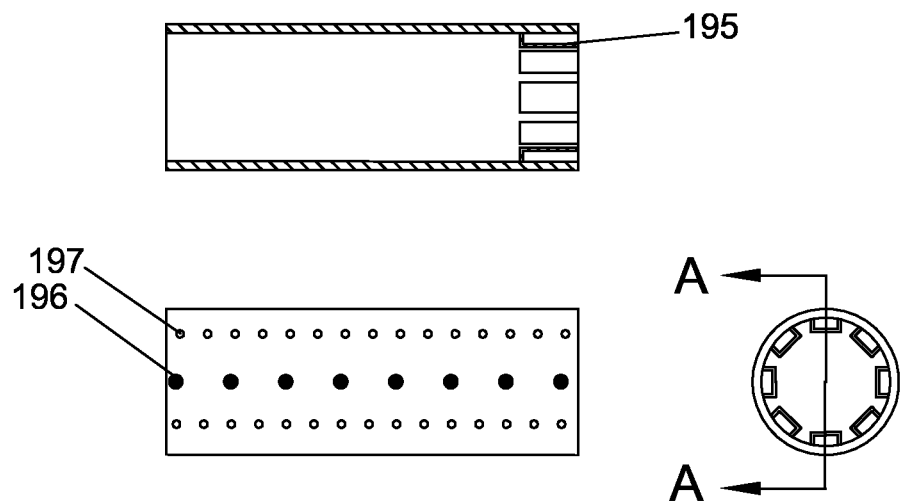
FIG. 50A is a drawing of a tubular implant or sleeve with pockets to insert magnets to allow attachment to a docking element or to another tubular implant.
Figure 50B:
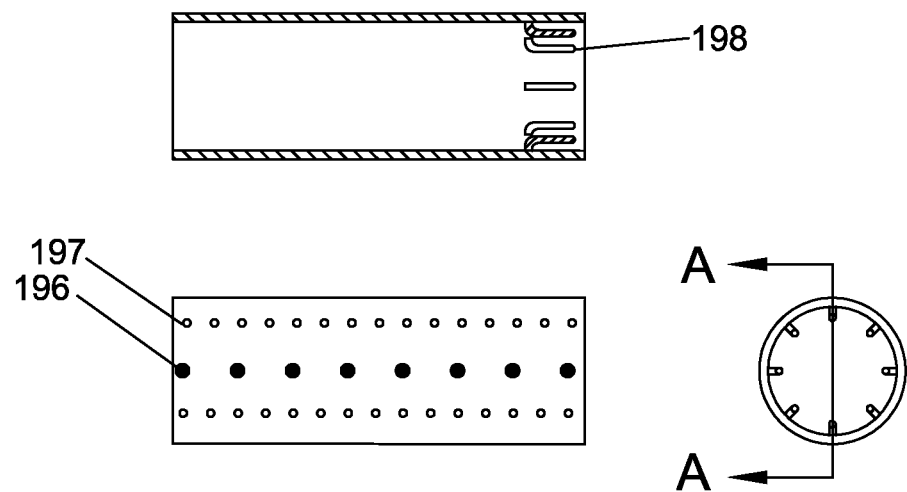
FIG. 50B is a drawing of a tubular implant or sleeve with hooks to attach docking element or another tubular implant.
Figure 51A:
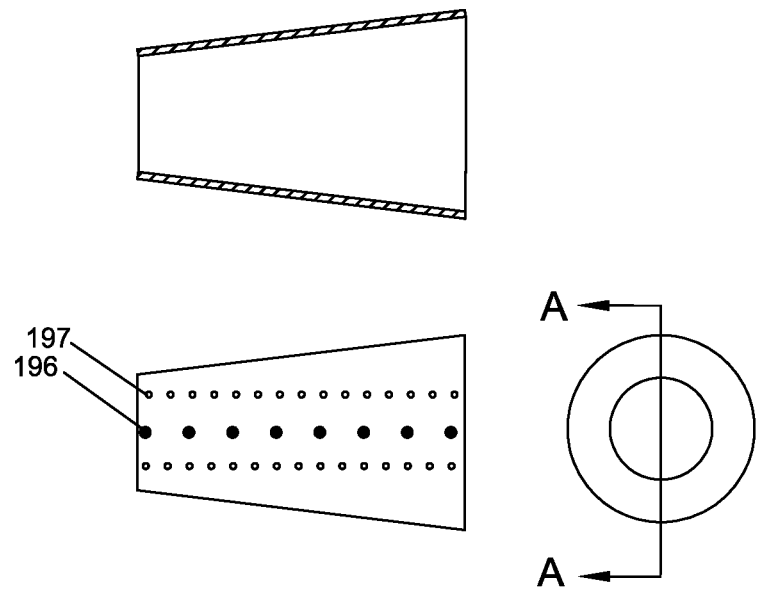
FIG. 51A is a conical or tapered shaped docking element or tubular implant.
Figure 51B:
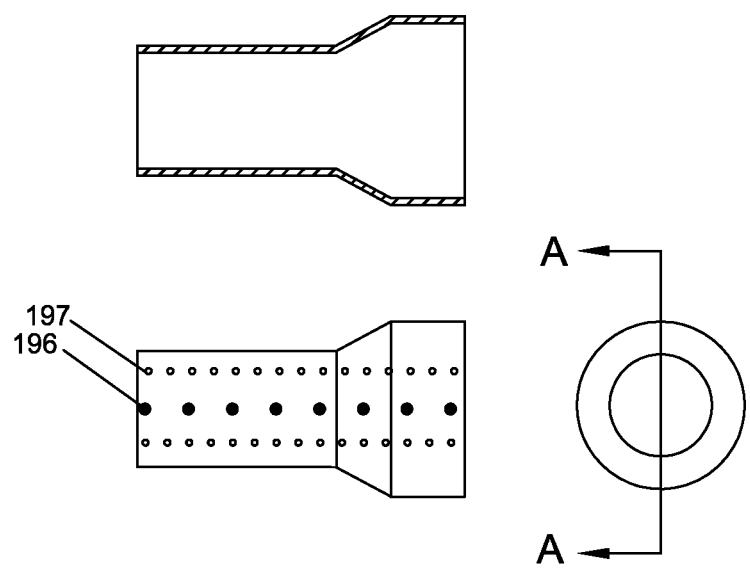
FIG. 51B is a docking element or tubular implant with a stepped diameter.
Figure 52:
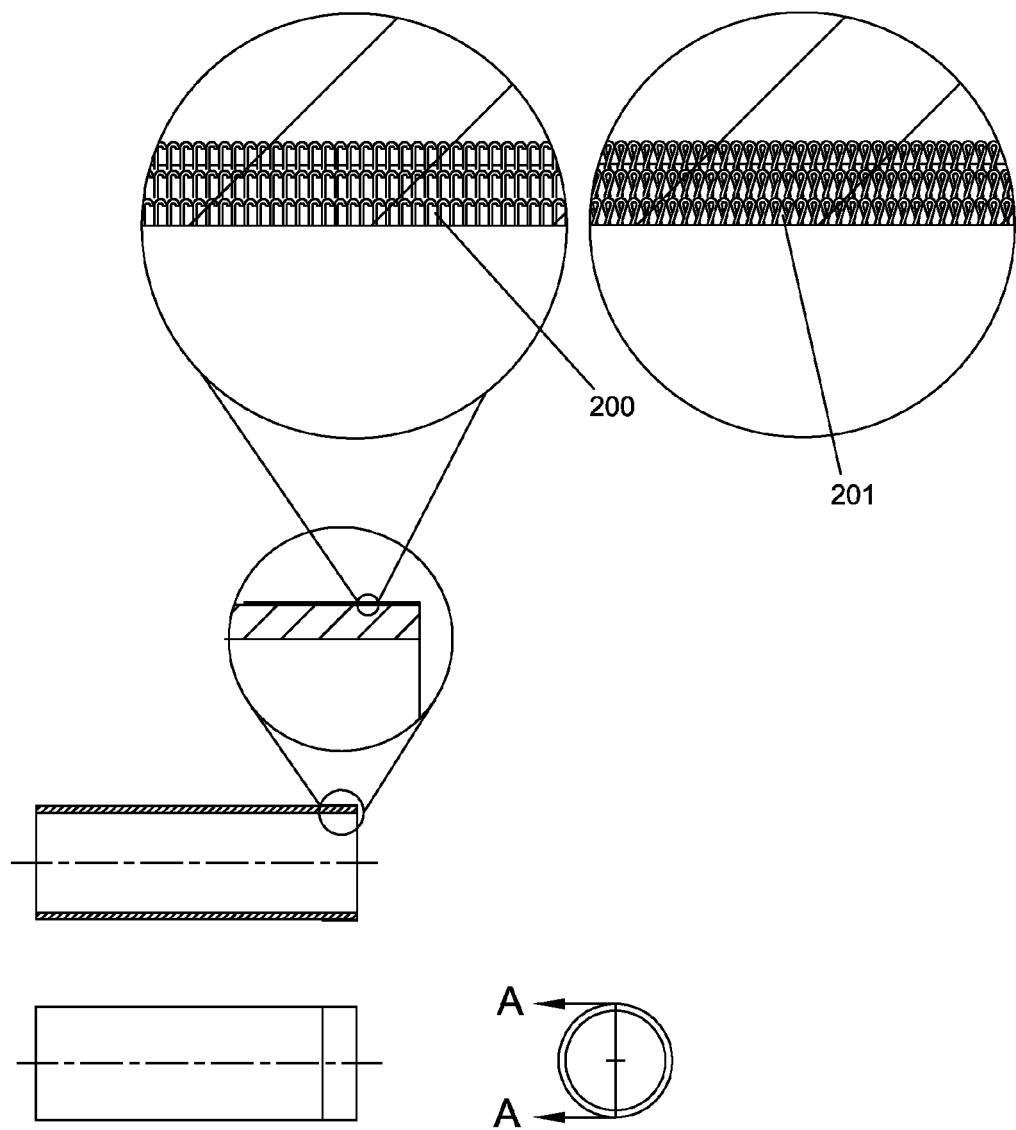
FIG. 52 is a tubular implant that has hook and loop (velcro) attachment means to attach to a docking element or another tubular implant.

FIG. 50A shows a basic sleeve with pockets 195. The basic sleeve may be used as part of a docking station or tubular implant. FIG. 50B shows a basic sleeve with hooks 198. The sleeve may be used as part of a docking station or tubular implant. FIG. 51A is a basic sleeve with a conical diameter. The sleeve may be used as part of a docking station or tubular implant. FIG. 51B is a basic sleeve with a stepped diameter. The simple sleeve may be used as part of a docking station or tubular implant. FIG. 52 is a basic sleeve with hook and loop fastener (Velcro) on the outside diameter. The sleeve may be used as part of a docking station or tubular implant.

Figure 53A:
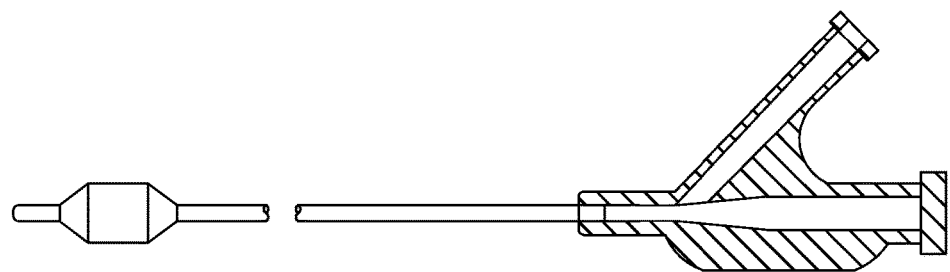
FIG. 53A is an over the wire balloon catheter for delivering and expanding balloon expandable stents for a docking element.
Figure 53B:
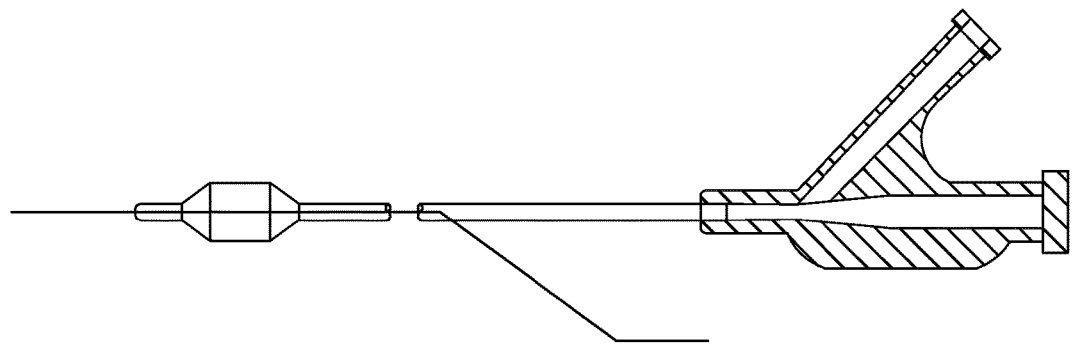
FIG. 53B is a rapid exchange balloon catheter for delivering and expanding balloon expandable stents for a docking element.

FIG. 53A is a balloon catheter for delivery of stents for docking elements or stented sleeves. The catheter is an over the wire design. FIG. 53B is a balloon catheter for delivery of stents for docking elements or stented sleeves. The catheter is of rapid exchange design.

Figure 54:
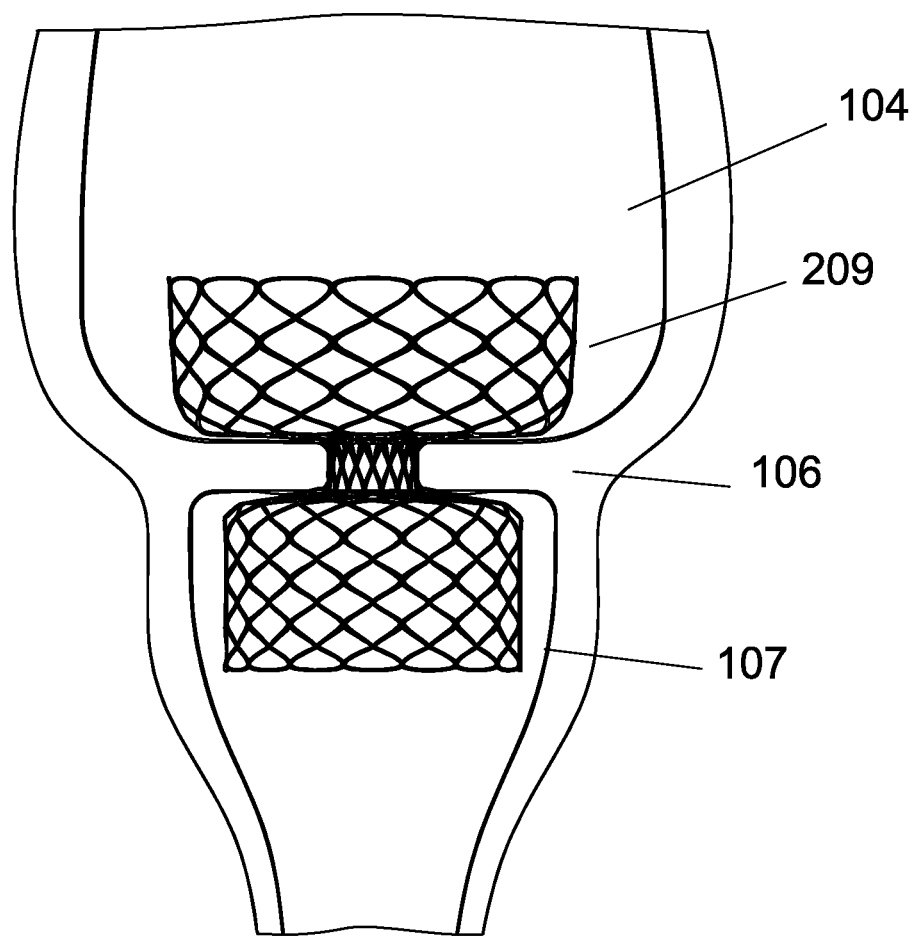
FIG. 54 shows a docking element design with a single-braided or laser-cut design placed at the pyloric junction.

FIG. 54 shows an enlarged view of the gastro-intestinal anatomy of the junction between the stomach and the duodenum, including the pyloric antrum 104, the pylorus 106, and the duodenal bulb 107. A soft, braided docking or anchoring element 209 is placed at the pyloric junction (i.e., extending across the pylorus). As shown in FIG. 54, the docking element is a variant of the element shown in FIG. 42 using a single braid. As shown, the docking element 209 is shaped such that it does not exert radial forces on the stomach wall or the duodenal wall for anchoring. It is retained within the pyloric junction due to its shape, which has an outer diameter larger than the maximum outer diameter of the pyloric orifice. As shown in FIG. 54, the docking element 209 includes a proximal portion (i.e., the portion located in the pyloric antrum 106), a distal portion (i.e., the portion located in the duodenal bulb 107, and a neck portion adapted to extend through the pylorus 106. According to various embodiments, the proximal and distal portion are shaped such that each has an unconstrained diameter of between about 15 and about 25 millimeters, and the neck portion has an unconstrained diameter of between about 5 and about 15 millimeters. In some embodiments, the ratio of the diameter of the proximal portion to the diameter of the neck portion is between about 1.2 and about 5. According to various embodiments, the neck portion is formed with an unconstrained diameter smaller than a maximum diameter of the native pylorus, such that the neck portion operates to restrict flow from the stomach into the duodenum (i.e., to function as a restrictive stoma). In other embodiments, the neck portion is formed with an unconstrained diameter larger than a maximum diameter of the native pylorus, such that the neck portion does not restrict flow from the stomach into the duodenum (i.e., through the pylorus).

Figure 55:
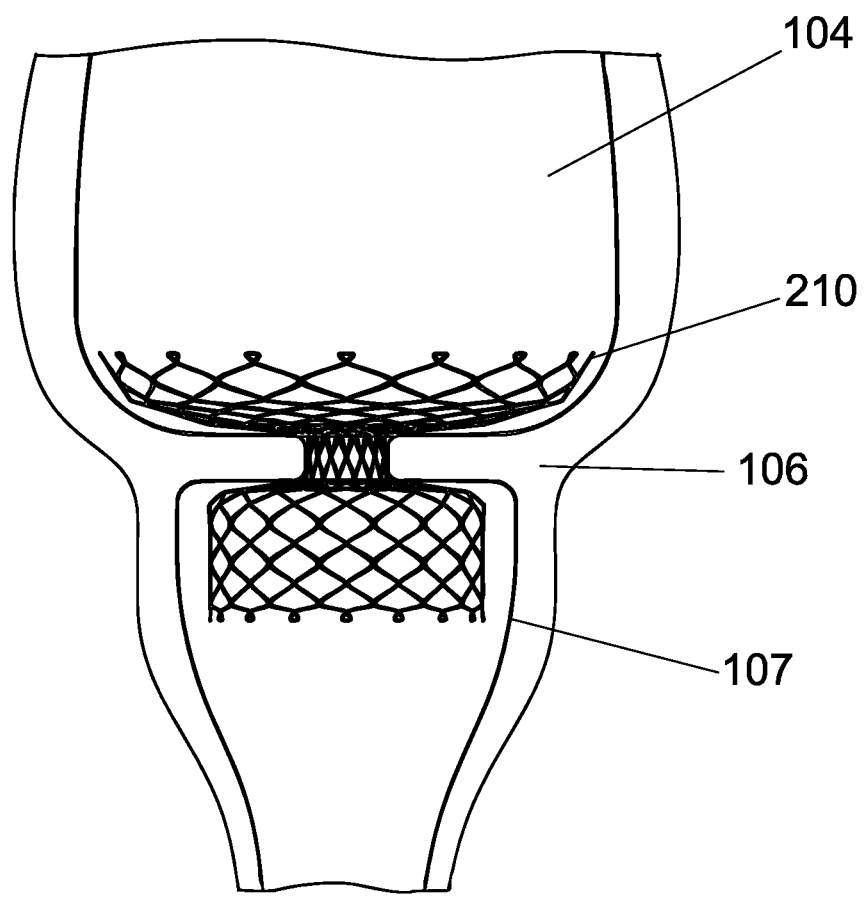
Figure 56:
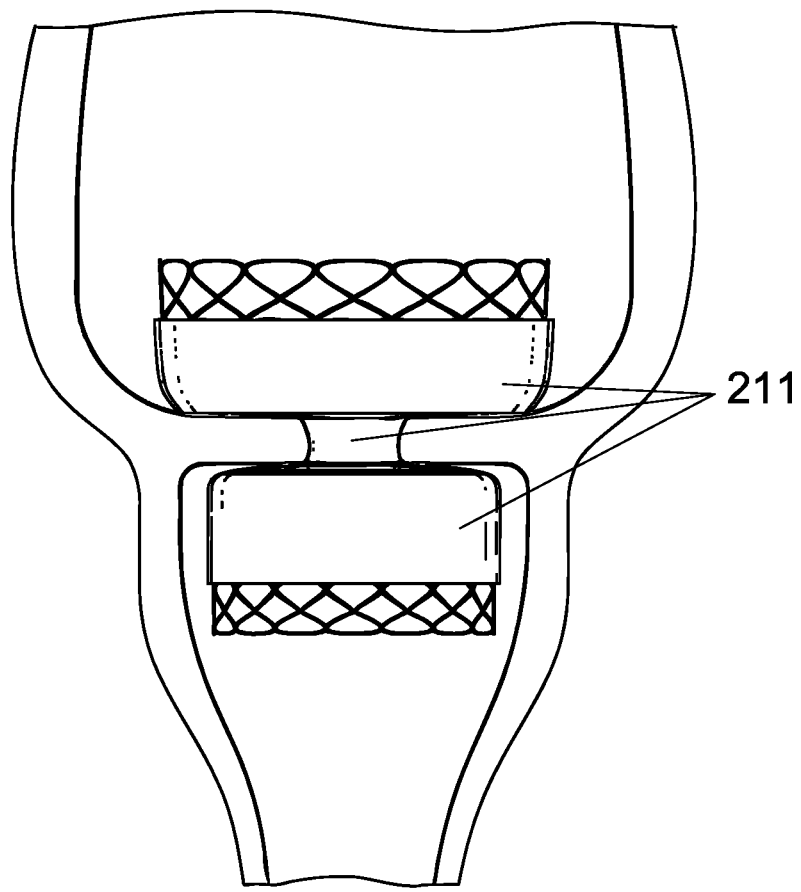
FIGS. 56 and 57 show docking elements of FIG. 55 and FIG. 56 covered with fabric or polymer sheets in areas where they contact tissue.
Figure 57:
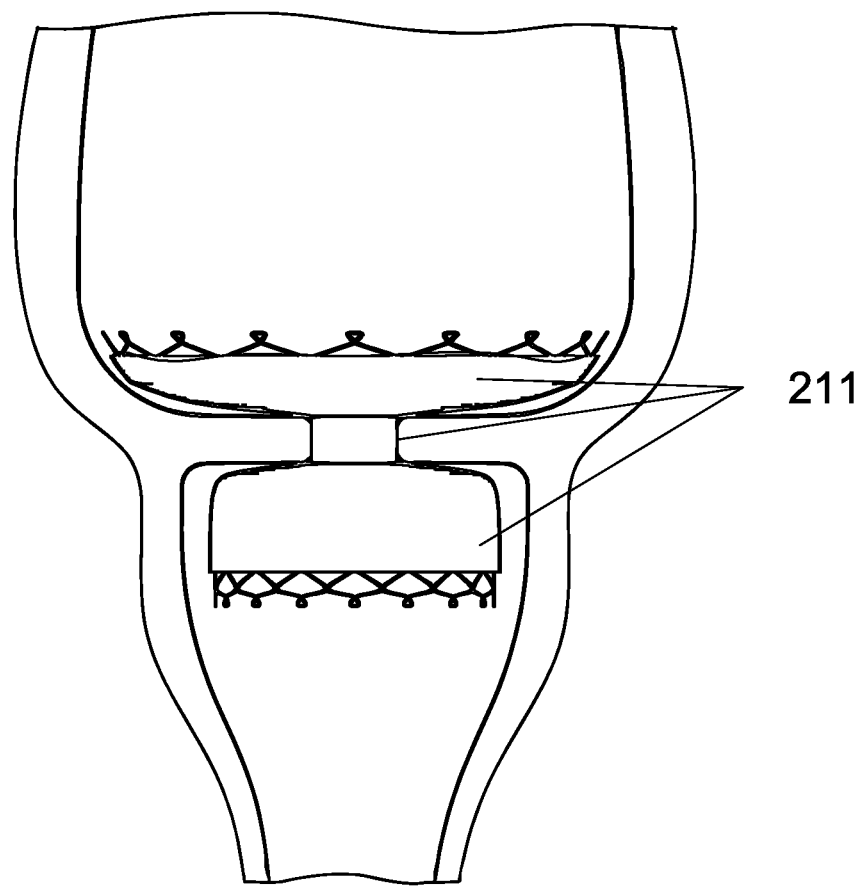

FIG. 55 shows another docking or anchoring element 210 having an alternate shape. In this instance, the proximal portion of the anchoring element 210 (i.e., the portion located on the pyloric antrum side) is more disk-like and serve as a pronounced anchoring/retaining flange for the device. In some embodiments, the anchoring element 210 has a maximum or unconstrained diameter slightly larger than an internal diameter of the pyloric antrum, such that the docking element 210 exerts a slight radial force on the wall of the pyloric antrum. In other embodiments, the unconstrained shape is such that the anchoring element 210 does not exert a radial force on the wall of the pyloric antrum. To minimize or prevent abrasive injury to tissue and tissue in-growth, and to provide for ease of replacement exemplary embodiments of the docking elements 209 and 210 could be covered with flexible woven fabric or nonwoven, extruded polymeric material used in synthetic medical grafts such as polyurethane, silicone, ePTFE, etc. FIGS. 56 and 57 show exemplary covered embodiments where the docking element includes a covering 211.

According to various embodiments, one or both of the proximal portion and the distal portion of the anchoring element are sized or shaped such that at least a portion of the anchoring element has an unconstrained diameter larger than the diameter of the corresponding anatomical organ (e.g., the pyloric antrum or the duodenal bulb), such that when implanted the anchoring element exerts a radial force upon the wall of the organ.

Figure 58:
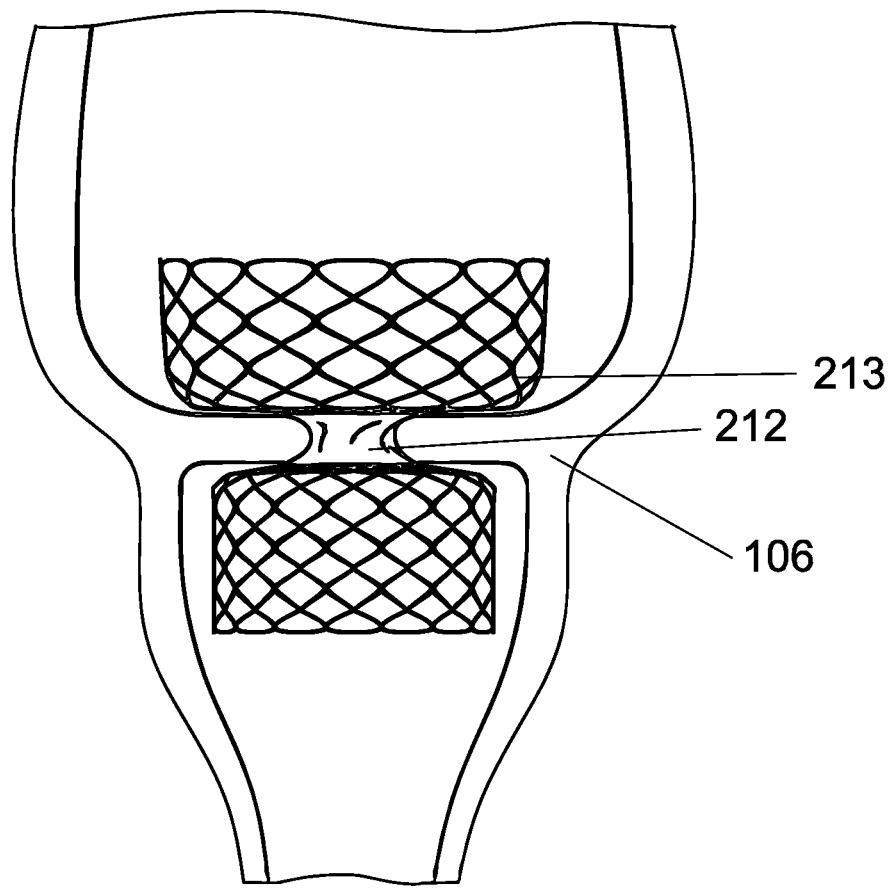
FIG. 58 shows a different design of the docking element placed within the pylorus, where two metallic elements (one on the stomach side and one on the duodenal side) are connected by a flexible sleeve element
Figure 59:
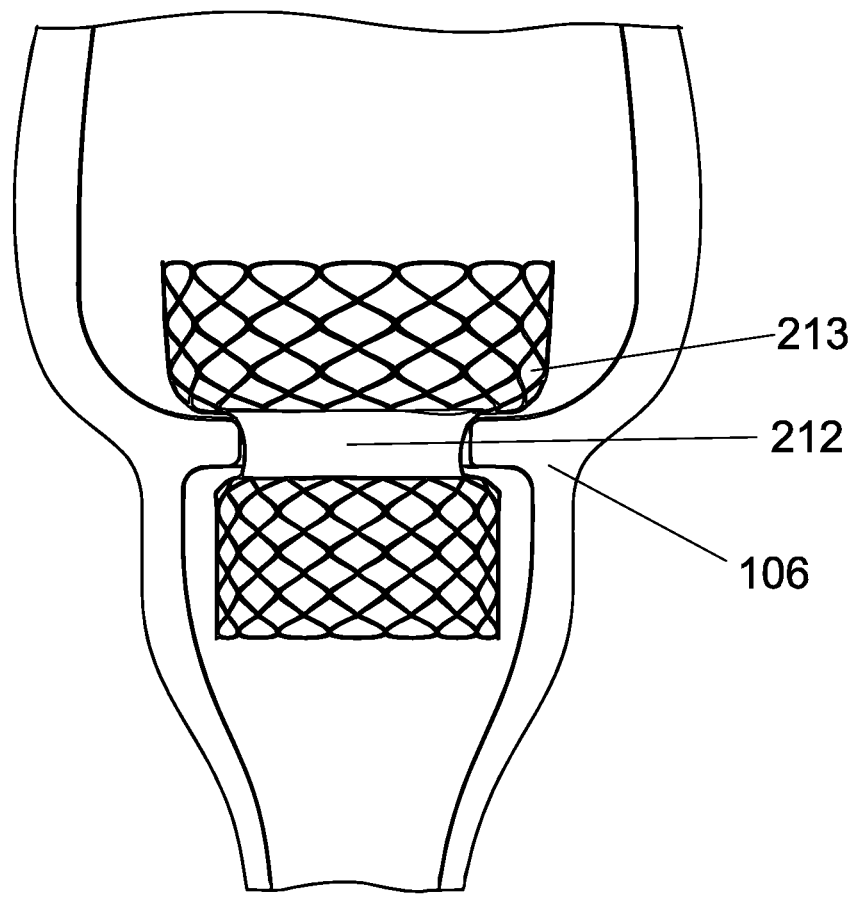
FIG. 59 depicts the docking element of FIG. 58 where the flexible sleeve element has expanded with the opening of the pyloric valve.
Figure 60:
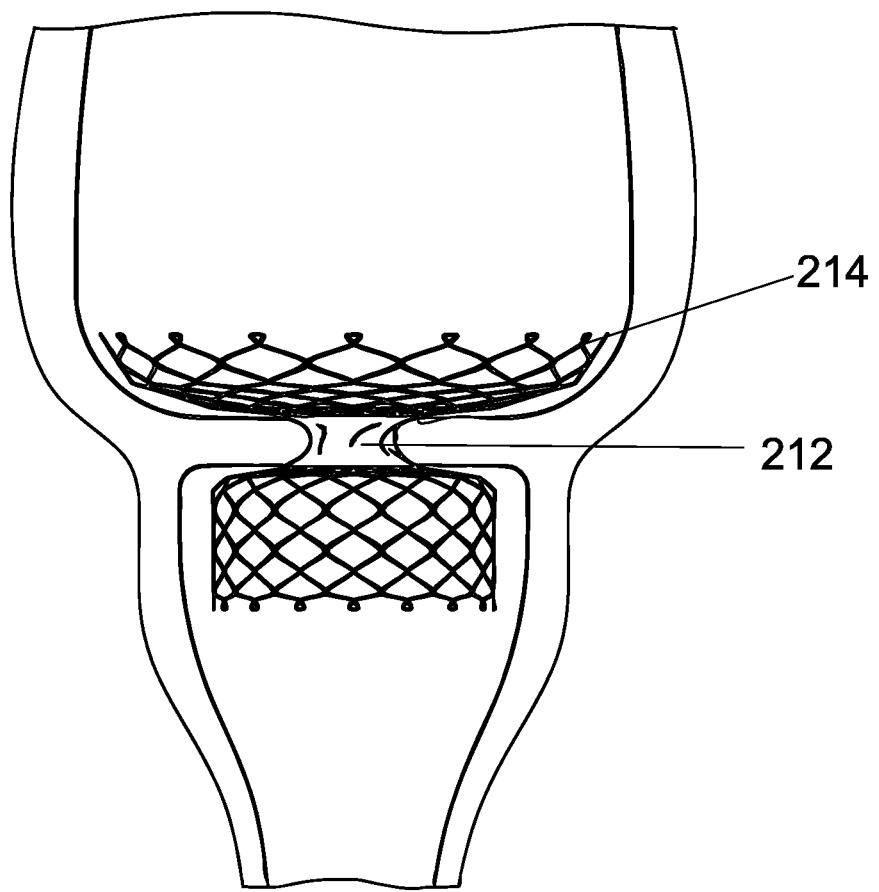
FIG. 60 depicts another docking element design incorporating a flexible sleeve element.

FIG. 58 shows a different design of the docking element, where the docking element 213 now consists of separate proximal (i.e., stomach side) and distal (i.e., duodenal side) metallic braided elements connected by a flexible sleeve (tubular) element 212. The flexible element 212 could be constructed of materials such as silicone, polyurethane, ePTFE, etc., which are resistant to stomach acid, enzymes and intestinal juices. The flexible element 212 is provides minimal interference to the opening and closing of the pyloric valve. FIG. 58 depicts the sleeve element in a somewhat compressed state (hence the drawing showing wrinkles to the sleeve 212. FIG. 59 depicts the same docking element 213 where the pylorus 106 is now fully open and the sleeve element 212 is an expanded state. FIG. 60 depicts another docking element 214 where the flexible sleeve element 212 is attached to other docking structures such as the docking element 210 shown in FIG. 55. According to various embodiments, the flexible element 212 has an outer diameter substantially similar to the maximum diameter of the native pylorus. The flexible element 212, for example, may have a diameter of between about 5 and about 15 millimeters. According to other embodiments, the diameter of the flexible element 212 is set somewhat smaller than the maximum diameter of the pylorus, such that the flexible element 212 acts to restrict flow from the stomach into the duodenum. According to various embodiments, the neck portion is attached to the proximal and distal stent portions by a sewing technique.

Figure 61:
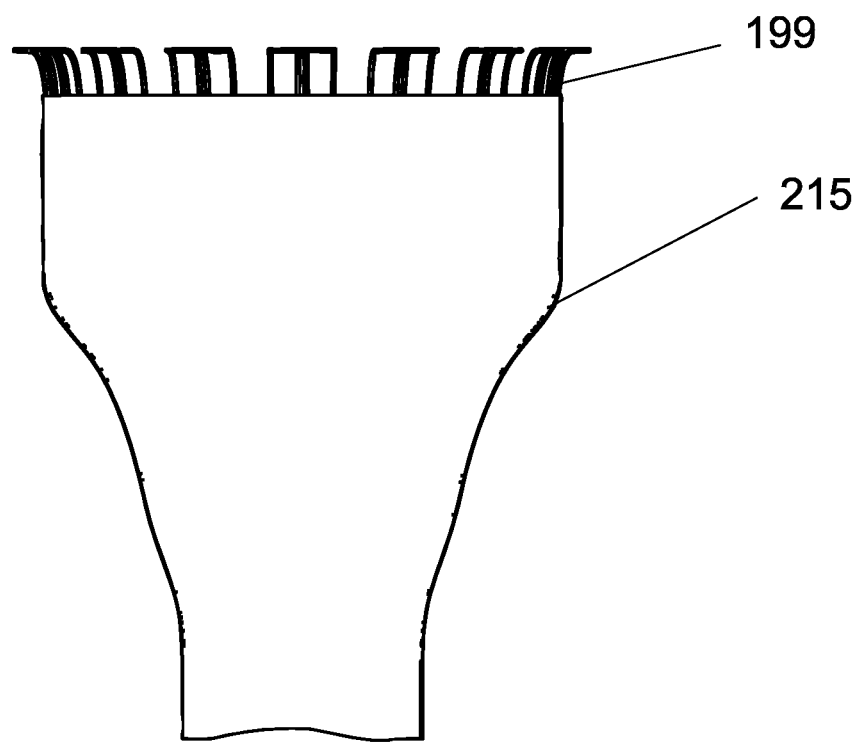
FIG. 61 depicts a tubular implant which can be reversibly attached to various compatible docking elements described elsewhere such as those shown in FIG. 54 through FIG. 58.

FIG. 61 depicts a tubular implant 215, which is a variant of the tubular implant of FIG. 41. Here, the flexible sleeve portion is more stepped in shape, such as is shown in the tubular implant in FIG. 51B. The stepped portion of the tubular implant can serve the purpose of acting like a restrictive element for food passage, depending on the choice of dimensions of the inlet and outlet. The tubular element also has ring-like anchoring or coupling features 199 attached to its proximal end similar to the tubular element of FIG. 41.

Figure 62:
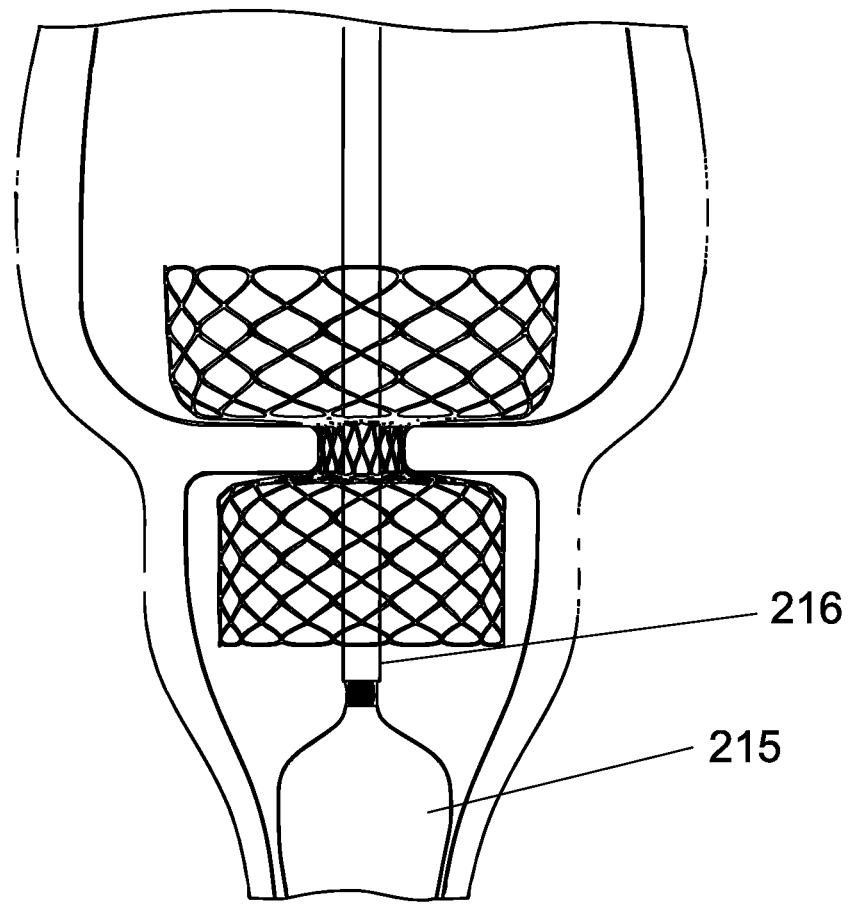
FIG. 62 shows delivery of the tubular implant of FIG. 61 close to the docking element of FIG. 54.
Figure 63:
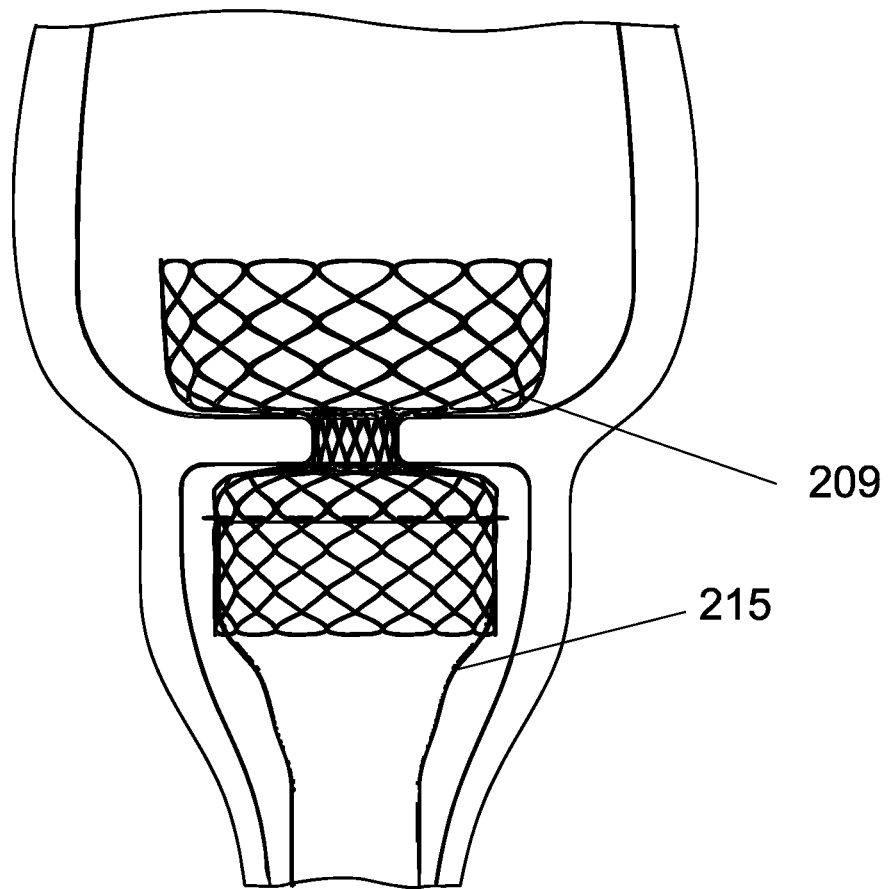
FIG. 63 depicts the docking element and the tubular element mated together upon release from the delivery catheter

FIG. 62 depicts the ring like anchoring elements 199 of the tubular implant 215 of FIG. 61 constrained in a delivery catheter 216 as it is being withdrawn close to the docking element. FIG. 63 depicts the docking element and the tubular implant 215 mated together upon release from the delivery catheter. By withdrawing the delivery catheter while the tubular element is anchored in place, the ring like anchoring elements are released from the delivery catheter and expand to their unconstrained set shape and diameter. Upon such expansion, the fingers or protrusions of the coupling feature 199 engage the distal portion of the docking element. In these embodiments, the distal portion of the docking element is sized and shaped such that the protrusion of the coupling feature may extend through the openings (i.e., docking features) in the proximal portion, such that the coupling feature 199 of the tubular implant engages the docking or anchoring element. In addition to providing an anchoring function by resisting forces directed toward the pylorus or stomach, the distal portion of the docking element 209 further provides some amount of structural support to the tubular implant 215, which help resist kinking, binding or twisting of the tubular implant.

Figure 64:
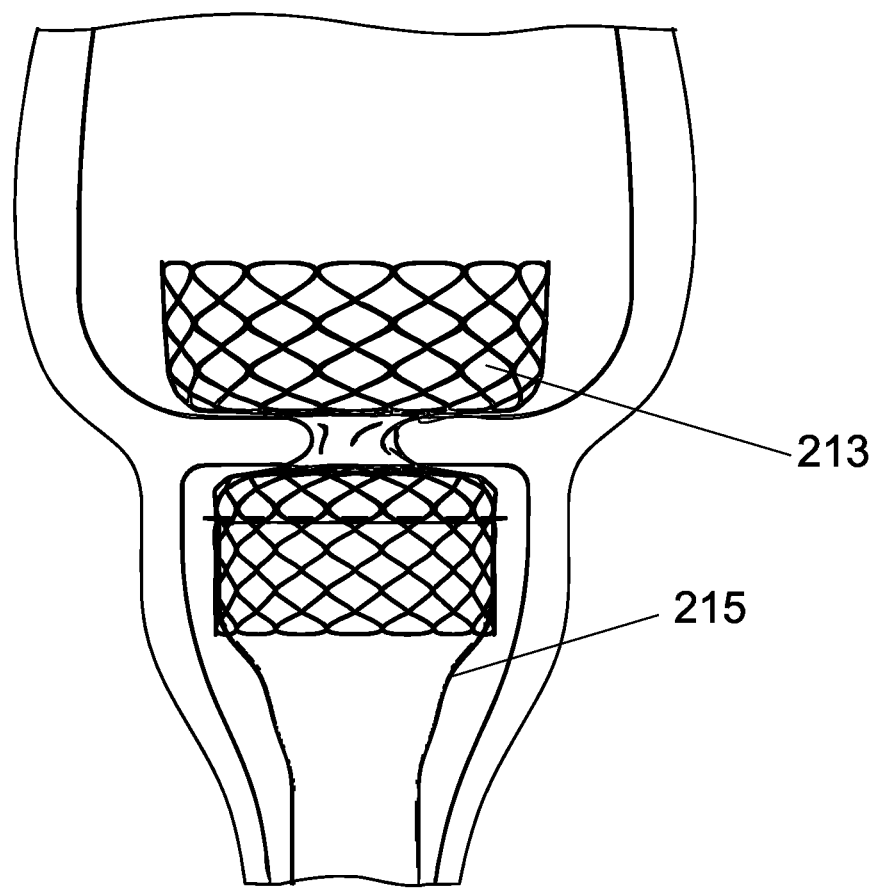
FIG. 64 shows where the tubular element is now attached to the docking element of FIG. 58
Figure 65:
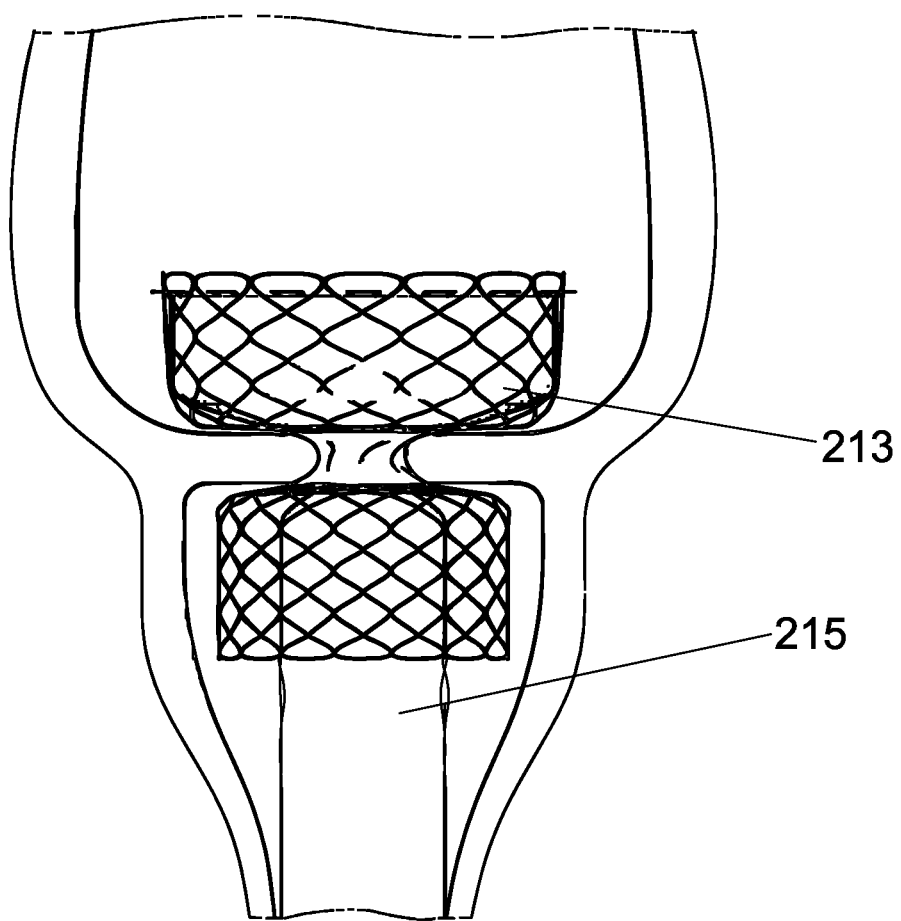
FIG. 65 shows a situation where the tubular element is attached to the docking element of FIG. 58 on the stomach portion of the docking element.

FIG. 64 shows the tubular implant 215 attached to the docking element 213 using the same steps as outlined in FIGS. 62 and 63. FIG. 65 shows a variant of the same concept where the tubular element 215 is now attached to the stomach side of the docking element 213. Here, the delivery catheter will have to withdrawn through the pylorus before activating the release of the ring element.

While each of FIGS. 63-65 show a modular system in which a tubular implant is removably or releasably coupled with a docking or anchoring element, according to other embodiments, the tubular implant is structurally integrated with the docking or anchoring element (e.g., such as is shown in FIGS. 19-20). The tubular implant and docking element may be integrated using a variety of techniques, including for example adhesive bonding, mechanical fastening, sewing, and overmolding. Likewise, according to some embodiments, portions of the system are modular while other portions are integrally formed. For example, according to exemplary embodiments, the anchoring element and tubular implant located within the duodenum are integrally formed and the docking element and tubular implant located at the gastro-esophageal junction and within the stomach are modular.

Figure 66:
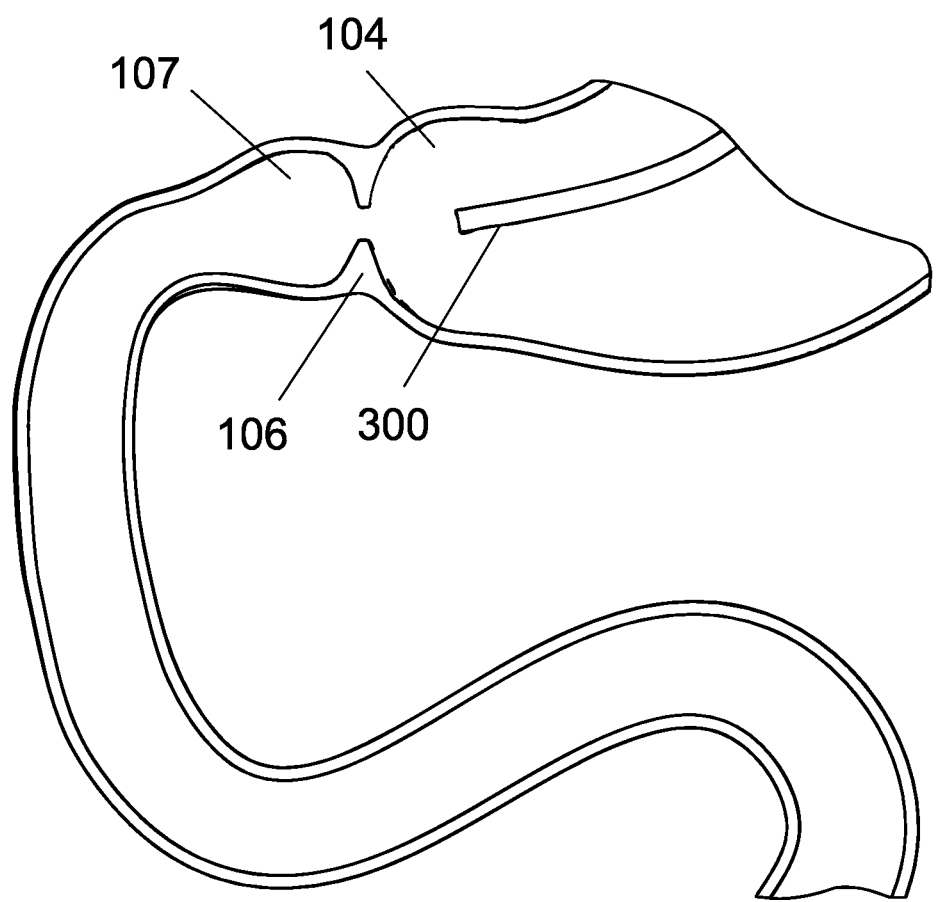
FIGS. 66-78 show schematic views of various stages of an implantation method according to embodiments of the invention.

FIGS. 66-78 show schematic views of various stages of an implantation method according to embodiments of the invention. FIG. 66 shows the initial stage of a minimally invasive method of implanting any of the various embodiments disclosed herein. As shown, the physician has advanced (e.g., endoscopically) a delivery system 300 to the pyloric antrum 104. The delivery system 300, according to some embodiments, includes an endoscope for visualization and a dual catheter system for securing the prostheses in a collapsed configuration. According to some embodiments, the delivery system 300 includes each of the components shown in and described with reference to FIG. 8.

Figure 67:
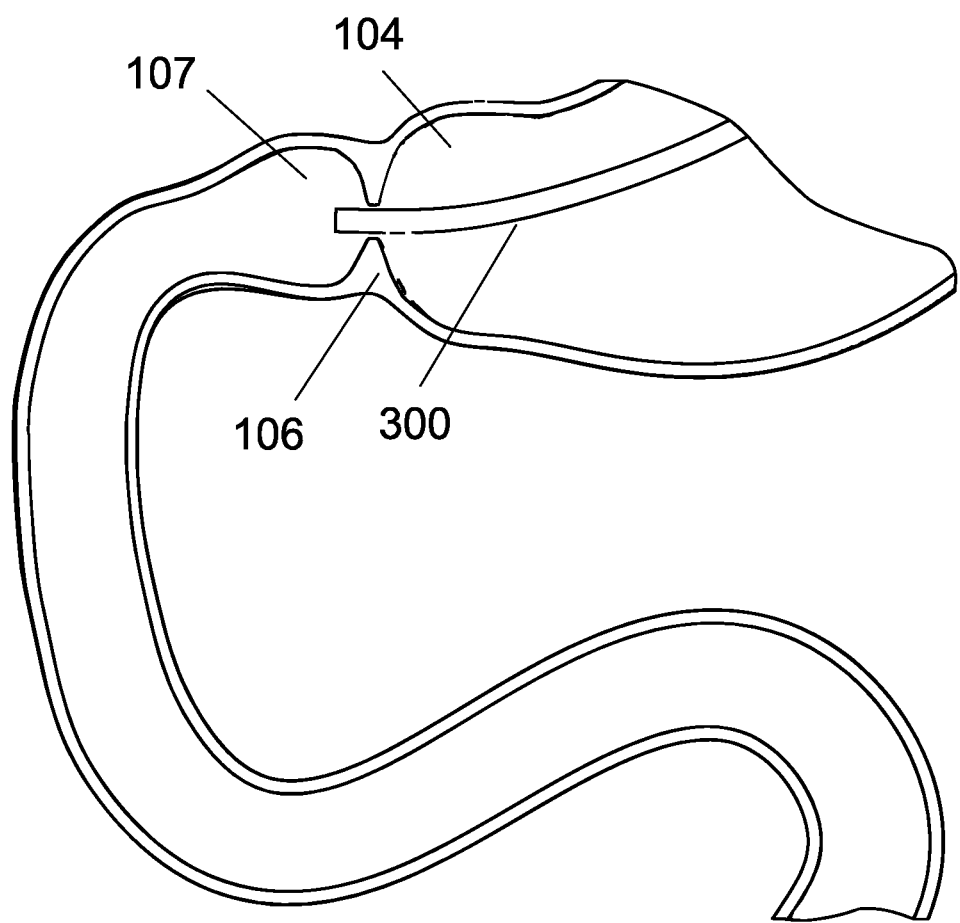
Figure 68:
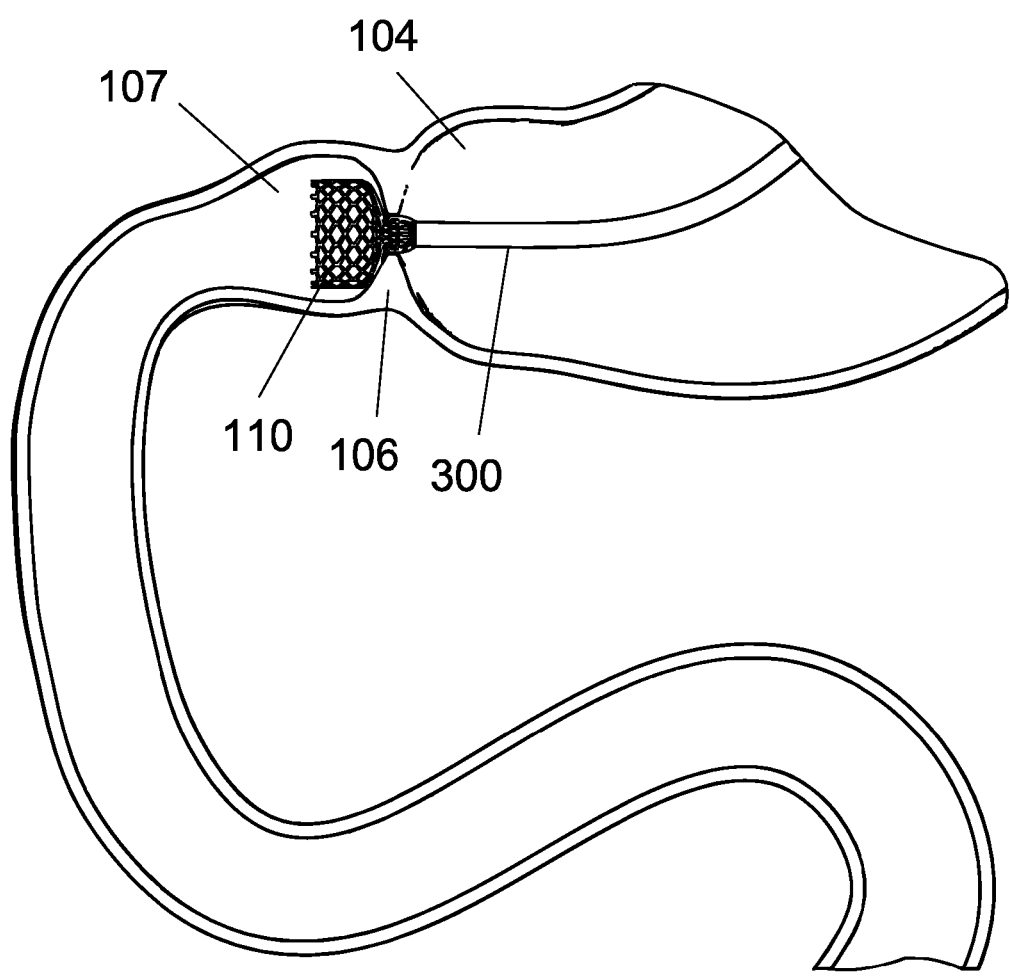
Figure 69:
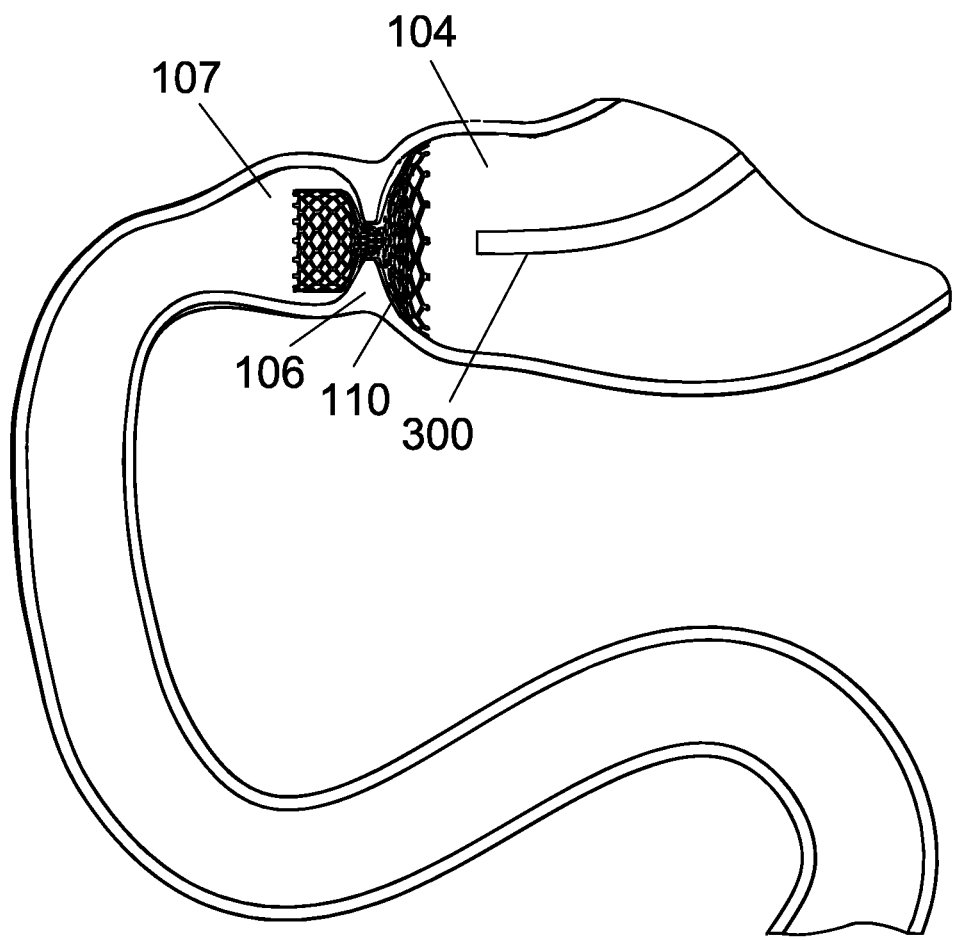
Figure 70:
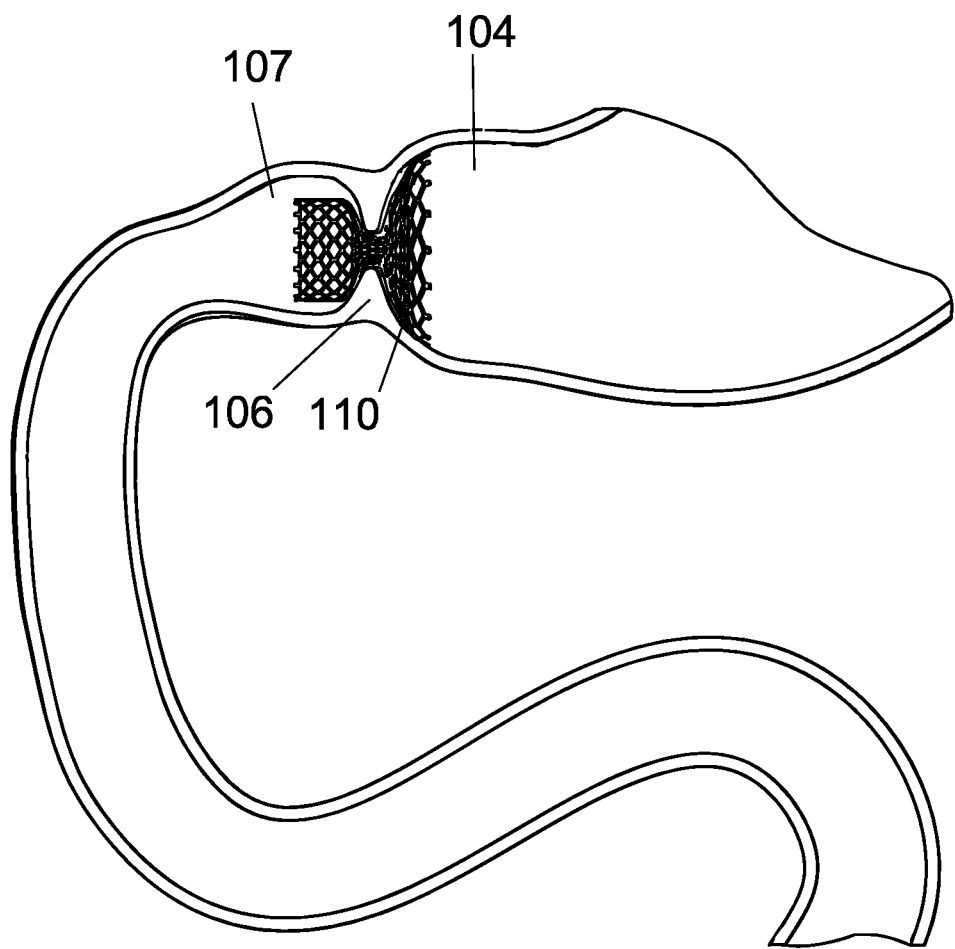

As shown in FIG. 67, the physician has successfully guided the delivery system 300 through the pylorus 106, such that a tip of the delivery system is located within the duodenal bulb 107. Next, as shown in FIG. 68, the physician has actuated the delivery system 300 (e.g, by retracting an outer sheath or catheter), so as to release a distal portion of the docking or anchoring element 110 in the duodenal bulb. As shown, the physician advances the delivery system 300 a sufficient distance to allow the distal portion to fully expand within the duodenal bulb 107 and a neck portion of the anchoring element 110 to expand within the opening of the pylorus 106. Then, as shown in FIG. 69, the delivery system 300 is further actuated to effect release of a proximal portion of the anchoring element 110 with the pyloric antrum 104. As shown, at this stage, the anchoring element 110 is fully disengaged from the delivery system. As shown in FIG. 70, the anchoring element is implanted across the pylorus 106, such that the proximal portion of the anchoring element engages the proximal surface of the pylorus and the distal portion engages the distal surface of the pylorus.

Figure 71:
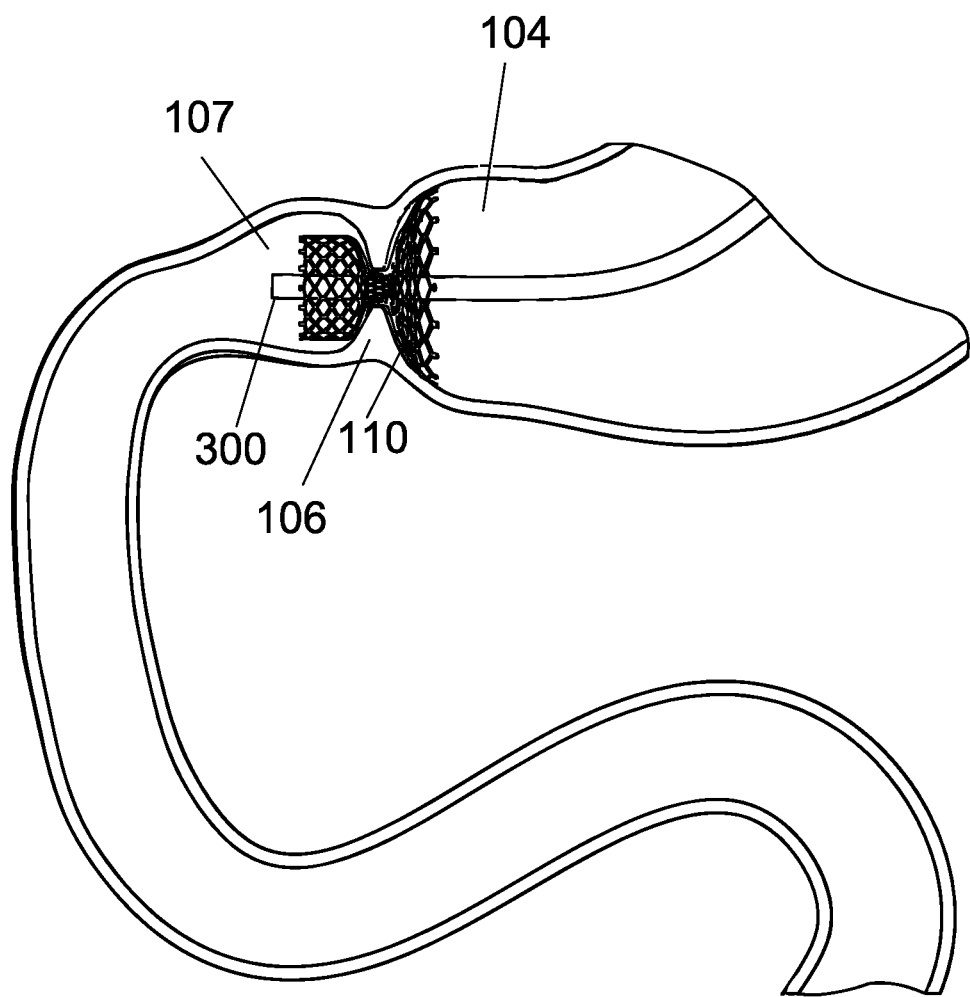
Figure 72:
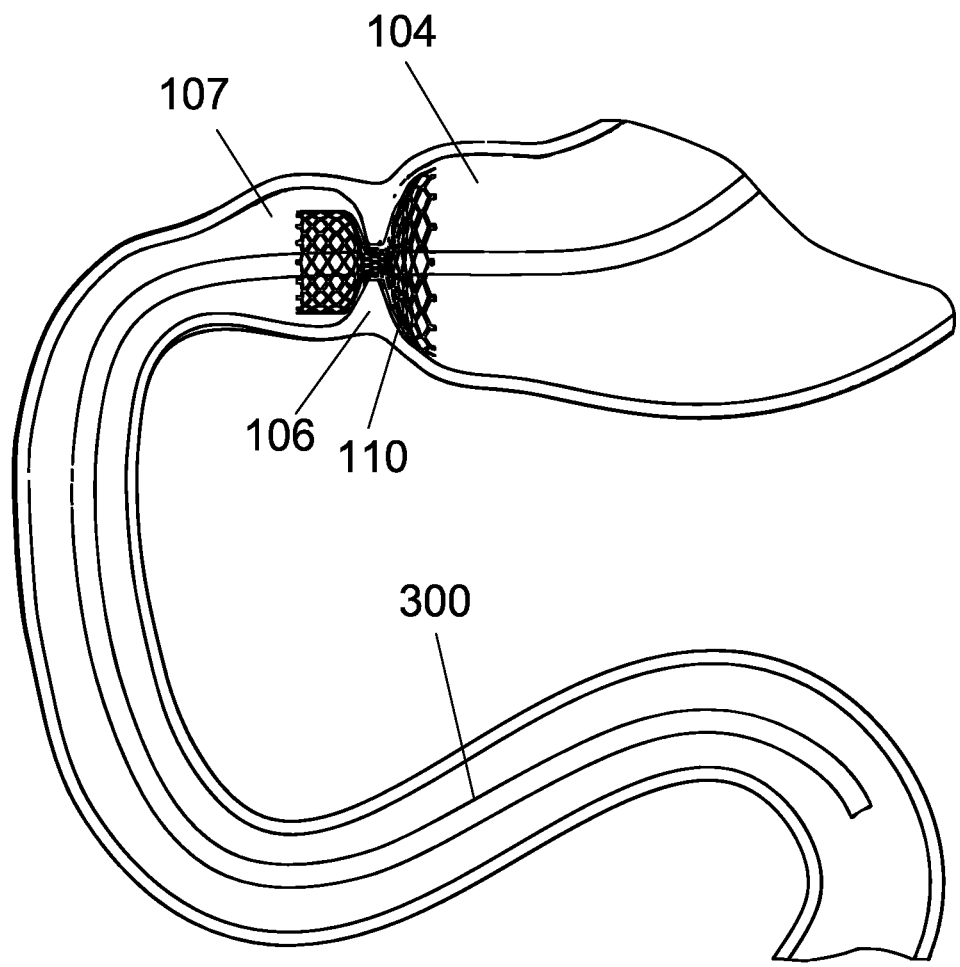
Figure 73:
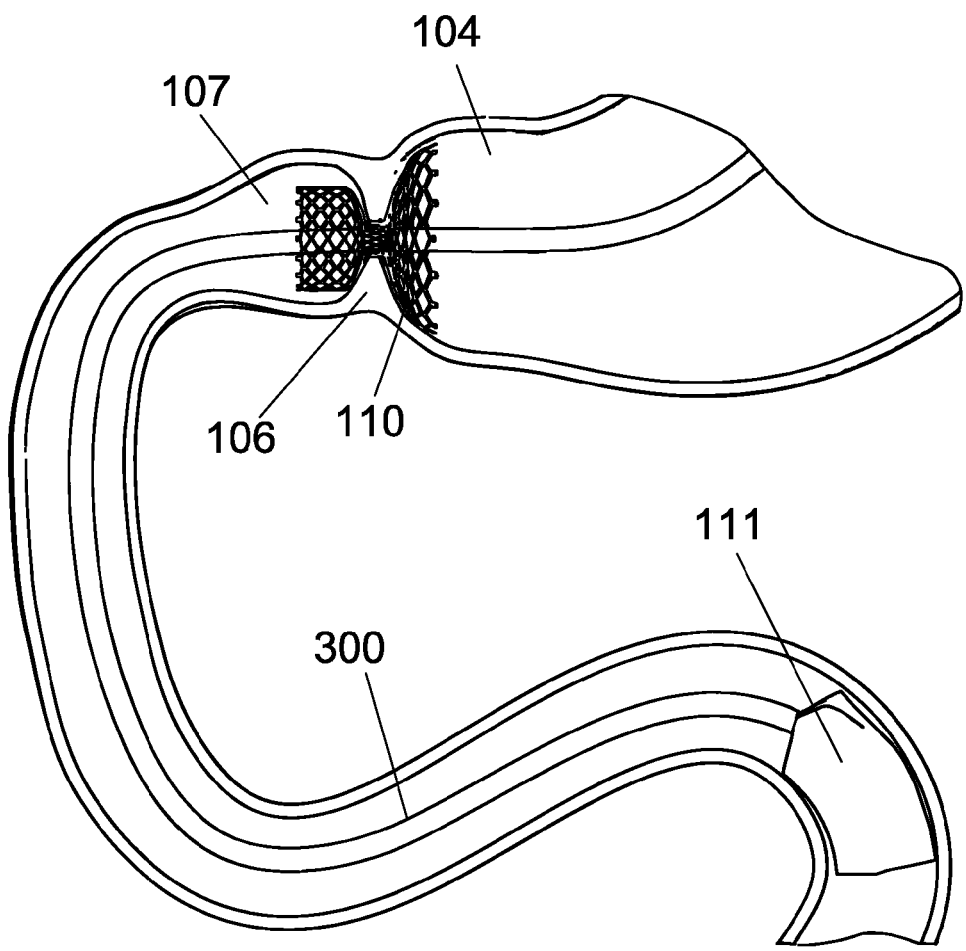
Figure 74:
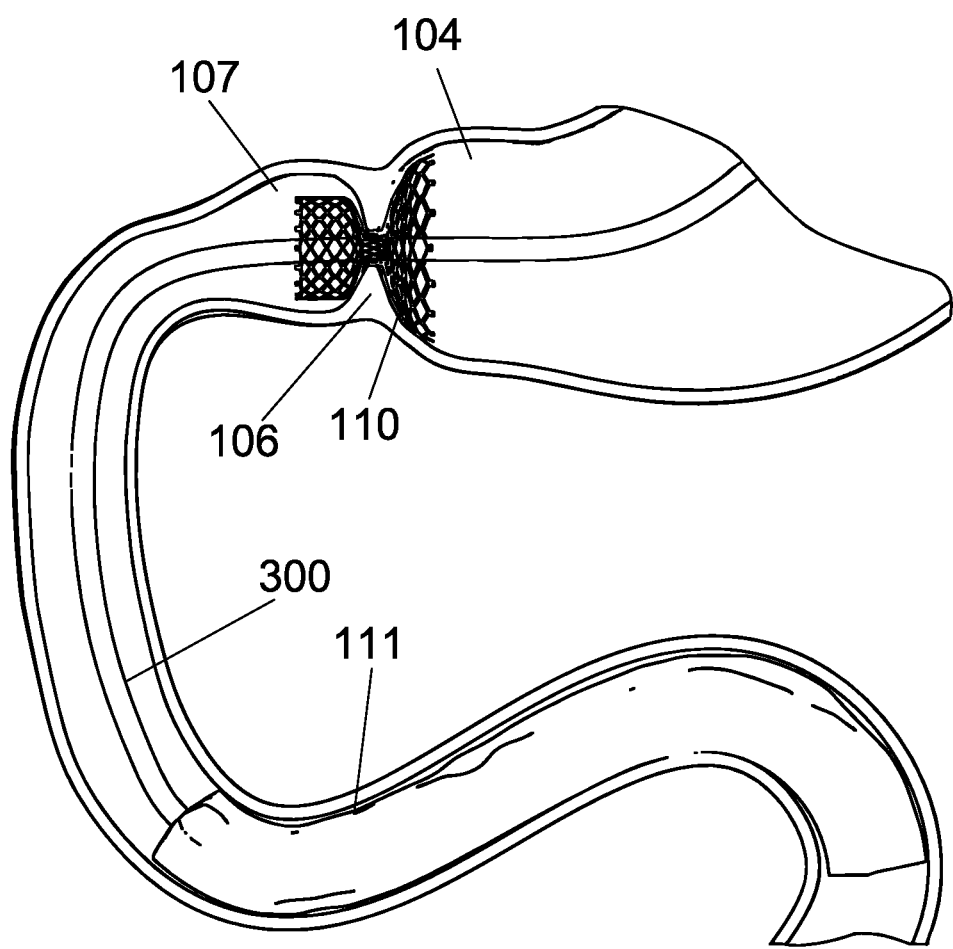
Figure 75:
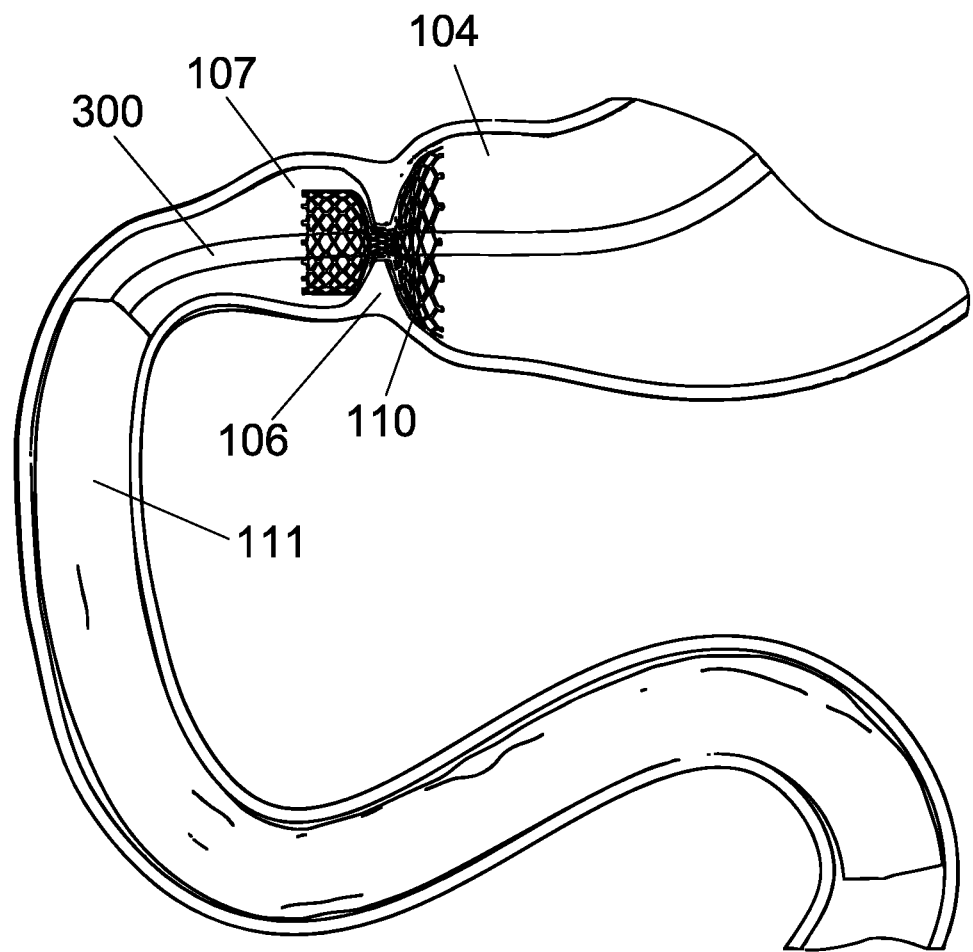
Figure 76:
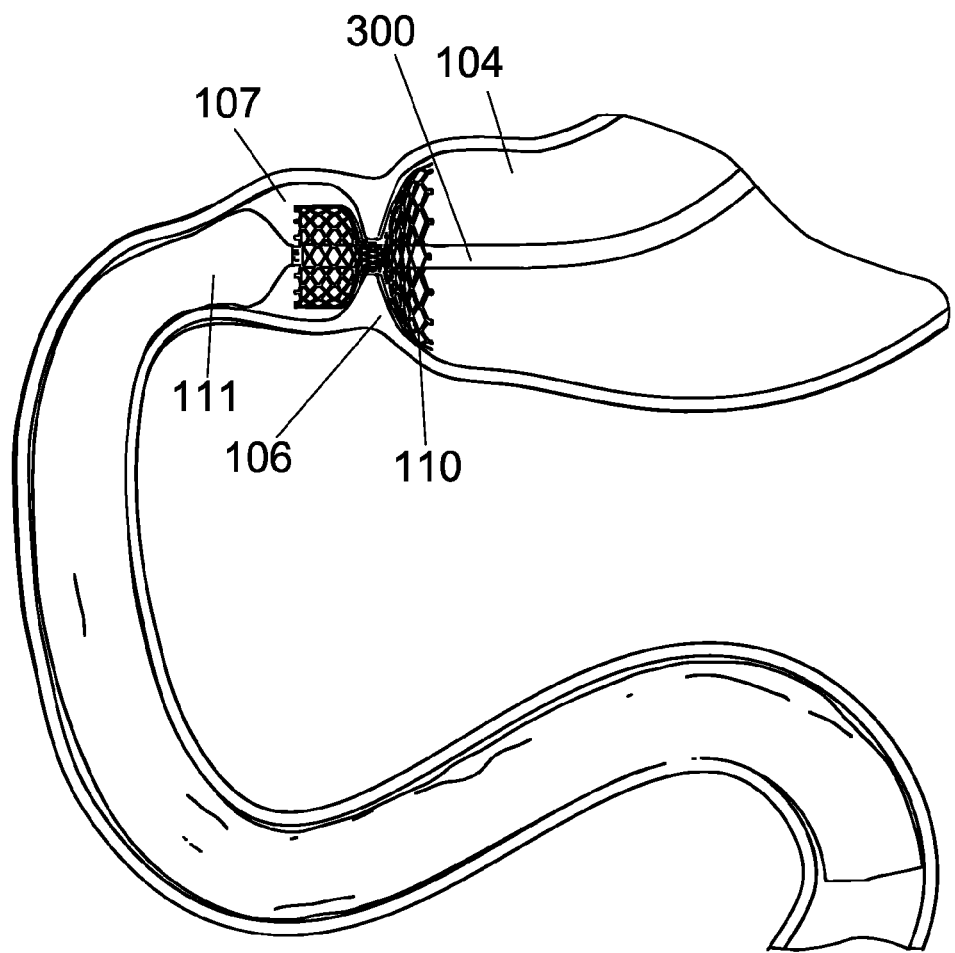
Figure 77:
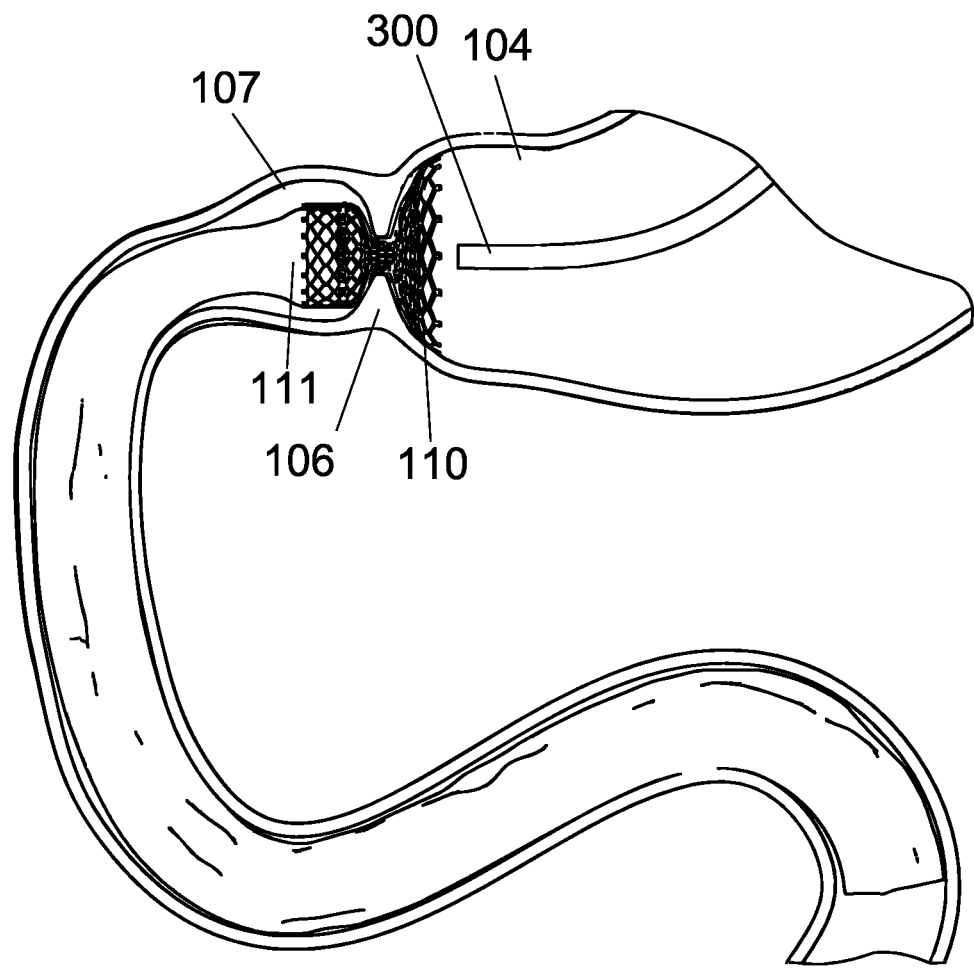
Figure 78:
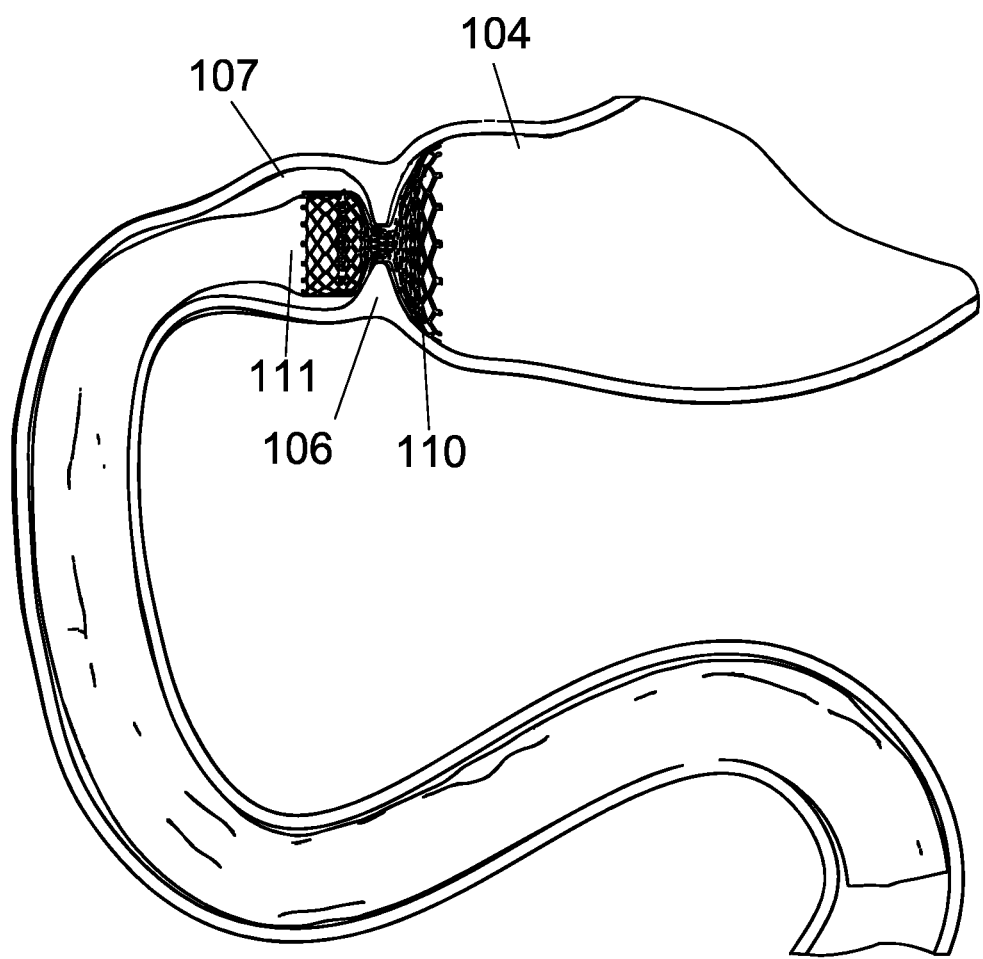

Next, as shown in FIG. 71, the delivery system 300, which holds the tubular or therapy element 111 in a collapsed configuration, is advanced across the pylorus 106 into the duodenal bulb 107. The delivery system 300, as shown in FIG. 72, is then advanced further down the duodenum (and, as desired, the jejunum), until the tip reaches the desired distal most implant location. Then, as shown in FIG. 73, the physician actuates the delivery system 300 (e.g., by retracting an outer catheter), to release a distal portion of the therapy element 111 with the duodenum (or jejunum). Next, as shown in FIGS. 74-76, the delivery system is further retracted such that the therapy element 111 is further released from the delivery system 300. As shown in FIGS. 77-78, the therapy element 111 is fully released from the delivery system 300 and has engaged the docking element 110.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A modular system for treating metabolic disorders, the modular system comprising:
   an anchoring element configured to be retained at a pyloric junction, the anchoring element including an expandable structure having a first reduced configuration configured for implantation of the anchoring element and a second expanded configuration configured for engaging a pylorus, the anchoring element including a first flange defining an outer diameter in the expanded configuration, a second flange defining an outer diameter in the expanded configuration, a neck portion having a first end attached to the first flange, a second end attached to the second flange, and a neck wall extending between the first end and second end and defining an outer diameter of the neck portion that is smaller than the outer diameter of the first flange and the second flange, the outer diameter of the first flange and the second flange larger than a maximum diameter of a pyloric orifice of a patient such that movement of the anchoring element toward the intestine is inhibited by contact of the first flange with the stomach side of the pylorus and movement of the anchoring element toward the stomach is inhibited by contact of the second flange with the intestinal side of the pylorus, and a docking feature,
wherein the anchoring element does not penetrate into or exert a radial force upon a duodenal bulb; and
a tubular implant adapted for placement within the gastrointestinal tract, the tubular implant having a coupling feature for engaging and coupling with the docking feature of the anchoring element;
wherein the docking feature and coupling feature are configured such that the tubular implant is releasably coupled to the anchoring element to facilitate removal of the tubular implant.

2. The modular system of claim 1 wherein the anchoring element further includes a sleeve element covering a part or an entire surface of a stent.

3. The modular system of claim 1 wherein the docking feature is a fabric or elastomeric cuff.

4. The modular system of claim 1 wherein the docking feature of the anchoring element comprises a plurality of magnetic elements.

5. The modular system of claim 1 wherein the docking feature of the anchoring element comprises a plurality of hook or a plurality of loop fastener elements.

6. The modular system of claim 1 wherein the docking feature of the anchoring element comprises at least one mechanical element adapted to interlock with a corresponding mechanical element of the coupling feature.

7. The modular system of claim 1 wherein the anchoring element comprises a double-braid stent with a space between an outer braid and an inner braid and further wherein the inner braid is configured as the docking feature.

8. The modular system of claim 1 wherein the tubular implant comprises at least one tubular element adapted to function as a conduit for food and organ secretions.

9. The modular system of claim 8 wherein the tubular element includes a restrictive feature for restricting the flow of food.

10. The modular system of claim 8 wherein the tubular element includes an anti-reflux valve.

11. The modular system of claim 4 wherein the magnetic elements provide attachment by either attraction, repulsion or magnetic levitation type mechanisms.

12. A modular system for treating metabolic disorders, the modular system comprising:
an anchoring element including an expandable structure, the anchoring element having a first reduced configuration configured for implantation of the anchoring element and a second expanded configuration configured to retain the anchoring element within a pylorus of a patient, the anchoring element including a proximal portion configured to be retained on a stomach side of a patient when implanted, a distal portion configured to be retained on an intestinal side of the patient when implanted, and a neck portion attached to the proximal portion and the distal portion, wherein in the second expanded configuration the proximal portion and the distal portion each have an outer diameter larger than a maximum outer diameter of a pyloric orifice of the patient such that the proximal portion contacts a stomach side and the distal portion contacts an intestinal side of the pyloric orifice of the patient after implantation in the patient, the anchoring element having a docking feature; and
a tubular implant adapted for placement within the gastrointestinal tract, the tubular implant having a coupling feature for releasably coupling with the docking feature of the anchoring element;
wherein the docking feature and coupling feature are configured such that the tubular implant is releasably coupled to the anchoring element to facilitate removal of the tubular implant; and
wherein the anchoring element is configured such that the proximal portion does not penetrate into or exert a radial force on the wall of a pyloric antrum, and the distal portion does not penetrate into or exert a radial force upon a duodenal bulb.

13. The modular system of claim 12 wherein the anchoring element further includes a sleeve element covering a part or an entire surface of a stent.

14. The modular system of claim 12 wherein the docking feature of the anchoring element comprises a plurality of magnetic elements.

15. The modular system of claim 12 wherein the docking feature of the anchoring element comprises at least one mechanical element adapted to interlock with a corresponding mechanical element of the coupling feature.

16. The modular system of claim 12 wherein the anchoring element comprises a double-braid with a space between an outer braid and an inner braid and further wherein the inner braid is configured as the docking feature.

17. The modular system of claim 12 wherein the tubular implant comprises a tubular element adapted to function as a conduit for food and organ secretions.

18. The modular system of claim 17 wherein the tubular element includes a restrictive feature for restricting the flow of food.

19. The modular system of claim 17 wherein the tubular element includes an anti-reflux valve.

20. A modular system for treating metabolic disorders, the modular system comprising:
an anchoring element having a reduced configuration configured for implantation and an expanded configuration configured to retain the anchoring element within a pylorus of a patient, the anchoring element including a proximal portion, a distal portion, and a neck portion extending between the proximal portion and the distal portion, wherein in the expanded configuration the proximal portion and the distal portion each have an unconstrained outer diameter larger than a maximum diameter of a pyloric orifice of the patient such that the proximal portion remains on the pyloric antrum side and the distal portion remains on the duodenal bulb side of the pylorus of the patient after implantation in the patient, and wherein the neck portion has an outer diameter that is less than the outer diameter of the proximal portion and the distal portion, each of the plurality of anchoring elements having a docking feature, wherein the plurality of anchoring elements do not penetrate into or exert a radial force upon a duodenal bulb;

a first tubular implant adapted for placement within the duodenum, the first tubular implant having a coupling feature for engaging and coupling with the docking feature of one of the plurality of anchoring elements; and a second tubular implant adapted for placement within the stomach, the second tubular implant having a length sufficient to extend from a distal end of the esophagus to a pylorus, the second tubular implant having a coupling feature for coupling with the docking feature of one of the plurality of anchoring elements;

wherein the docking feature and coupling feature are configured such that the first tubular implant is releasably coupled to the anchoring element to facilitate removal of the first tubular implant.

* * * * *